United States Patent
Austin et al.

(10) Patent No.: US 11,779,630 B2
(45) Date of Patent: Oct. 10, 2023

(54) PEPTIDES AND METHODS OF USING THE SAME

(71) Applicant: SERPIN PHARMA, LLC, Manassas, VA (US)

(72) Inventors: Dana Austin, Manassas, VA (US); Cohava Gelber, Manassas, VA (US)

(73) Assignee: SERPIN PHARMA, LLC, Manassas, VA (US)

( * ) Notice: Subject to any disclaimer, the term of this patent is extended or adjusted under 35 U.S.C. 154(b) by 0 days.

(21) Appl. No.: 17/753,013

(22) PCT Filed: Jul. 6, 2021

(86) PCT No.: PCT/US2021/040572
§ 371 (c)(1),
(2) Date: Feb. 15, 2022

(87) PCT Pub. No.: WO2022/010939
PCT Pub. Date: Jan. 13, 2022

(65) Prior Publication Data
US 2022/0265761 A1   Aug. 25, 2022

Related U.S. Application Data

(60) Provisional application No. 62/705,591, filed on Jul. 6, 2020.

(51) Int. Cl.
| | | |
|---|---|---|
| A61K 38/10 | (2006.01) | |
| A61P 25/04 | (2006.01) | |
| A61P 25/28 | (2006.01) | |
| A61P 11/06 | (2006.01) | |
| A61P 17/00 | (2006.01) | |
| A61P 31/14 | (2006.01) | |
| A61P 31/18 | (2006.01) | |
| A61P 37/08 | (2006.01) | |
| A61P 1/00 | (2006.01) | |
| A61P 11/00 | (2006.01) | |
| A61P 29/00 | (2006.01) | |

(52) U.S. Cl.
CPC ............ *A61K 38/10* (2013.01); *A61P 1/00* (2018.01); *A61P 11/00* (2018.01); *A61P 11/06* (2018.01); *A61P 17/00* (2018.01); *A61P 25/04* (2018.01); *A61P 25/28* (2018.01); *A61P 29/00* (2018.01); *A61P 31/14* (2018.01); *A61P 31/18* (2018.01); *A61P 37/08* (2018.01)

(58) Field of Classification Search
None
See application file for complete search history.

(56) References Cited

U.S. PATENT DOCUMENTS

2020/0017550 A1   1/2020 Mogelsvang et al.

FOREIGN PATENT DOCUMENTS

| EP | 4041262 A1 | 8/2022 |
|---|---|---|
| WO | 2011109768 A2 | 9/2011 |
| WO | 2011126882 A2 | 10/2011 |
| WO | 2013106273 A2 | 7/2013 |
| WO | 2013106589 A1 | 7/2013 |
| WO | 2014197524 A2 | 12/2014 |
| WO | 2017040287 A1 | 3/2017 |
| WO | 2019199634 A4 | 12/2019 |

OTHER PUBLICATIONS

Toldo et al, JACC: Basic to Translational Science; 2017; vol. 2, No. 5.*
Corren et al, Nature Immunology; Dec. 2019; vol. 20, pp. 1603-1609.*
International Search Report and Written Opinion for PCT/US2021/040572, dated Dec. 23, 2021.
Berta, et al., "Tissue plasminogen activator contributes to morphine tolerance and induces mechanical allodynia via astrocytic IL-1 beta and ERK signaling in the spinal cord of mice", Neuroscience 247: 376-385, May 2013.
Christia, P, et al., "Systematic characterization of myocardial inflammation, repair, and remodeling in a mouse model of reperfused myocardial infarction", J Histochem Cytochem 61(8): 555-570, Aug. 2013.
Cooke, J.P., "Inflammation and Its Role in Regeneration and Repair", Circ Res 124(8): 1166-1168, Apr. 2019.
EPO, "Office Action", Application No. 21838928.6, dated Feb. 1, 2023.
EPO, "Partial Supplementary European Search Report", Application No. 21838928.6, dated Oct. 12, 2022.
EPO, "Supplementary ESR", Application No. 21838928.6, dated Jan. 20, 2023.
Feng, Y., et al., "The protective role of autophagy in sepsis", Microb Pathog 131: 106-111, 2019.
Franchini, M, et al., "Low-density lipoprotein receptor-plated protein 1: new functions for an old molecule", Clin Chem Lab Med 49(6): 967-970, Jun. 2011.
Fregnan, F., et al., "Role of inflammatory cytokines in peripheral nerve injury", Neural regeneration research 7(29): 2259-2266, Oct. 2012.
Gali, C. C., et al., "Amyloid-beta impairs insulin signaling by accelerating autophagy-lysosomal degradation of LRP-1 and IR-β in blood-brain barrier endothelial cells in vitro and in 3XTg-AD mice", Molecular and Cellular Neuroscience 99: 103390, 2019.
Takenouchi, et al., "Beta-Amyloid Peptide, Substance P, and SEC Receptor Ligand Activate Cytoplasmic Ca2+ In Neutrophil-Like Hl-60 Cells: Effect of Chemotactic Peptide Antagonist BOCMLF", Peptides, Elsevier, Amsterdam, NL, vol. 16, No. 6, Jan. 1, 1995 (Jan. 1, 1995), pp. 1019-1024.
Gettins, P. G., et al., Aug. 1, 2017, "Inhibitory serpins. New insights into their folding, polymerization, regulation and clearance," The Biochemical journal 473(15): 2273-2293.
Griffin, D., et al., 1997, "The role of antibody in recovery from alphavirus encephalitis," Immunol Rev 159: 155-161.

(Continued)

*Primary Examiner* — Bridget E Bunner
*Assistant Examiner* — Fozia M Hamud
(74) *Attorney, Agent, or Firm* — Perkins Coie LLP

(57) ABSTRACT

Disclosed herein are SERPIN peptides, and analogues and derivatives thereof, and uses of the same for treating various conditions associated with LRP1 mediation.

6 Claims, 33 Drawing Sheets

Specification includes a Sequence Listing.

(56) References Cited

OTHER PUBLICATIONS

Grosso, R. A., et al., Jan. 3, 2019, "Hemin induces autophagy in a leukemic erythroblast cell line through the LRP1 receptor," Biosci Rep.

Gubler, D. J., Feb. 25, 2022, "The global emergence/resurgence of arboviral diseases as public health problems," Archives of Medical Research 33(4): 330-342.

Hashizume, H., et al., 2000, "Spinal glial activation and cytokine expression after lumbar root injury in the rat," Spine (Phila Pa 1976) 25(10): 1206-1217.

Hemonnot, A. L., et al., Aug. 30, 2019, "Microglia in Alzheimer Disease: Well-Known Targets and New Opportunities," Frontiers in Aging Neuroscience 11(233).

Herz, J., et al., Sep. 2001, "LRP: a multifunctional scavenger and signaling receptor," J Clin Invest 108(6): 779-784.

Hoffmann, M., et al., Apr. 16, 2020, "SARS-COV-2 Cell Entry Depends on ACE2 and TMPRSS2 and Is Blocked by a Clinically Proven Protease Inhibitor," Cell 181(2): 271-280.e278.

Huang, C., et al., Jan. 24, 2020, "Clinical features of patients infected with 2019 novel coronavirus in Wuhan, China," The Lancet 395(10223): 497-506.

Joslin, G., et al., Feb. 6, 1991, "The SEC receptor recognizes a pentapeptide neodomain of alpha 1-antitrypsin-protease complexes," J Biol Chem 266(17): 11282-11288.

Kawamura, A., et al., May 3, 2007, "Apolipoprotein E interrupts interleukin-1 beta signaling in vascular smooth muscle cells," Arterioscler Thromb Vasc Biol 27(7): 1610-1617.

Kehn-Hall, K., et al., Apr. 4, 2012, "Modulation of GSK-3beta activity in Venezuelan equine encephalitis virus infection," PLOS One 7(4): e34761.

Landowski, L. M., et al., Nov. 23, 2015, "Low-density Lipoprotein Receptor-related Proteins in a Novel Mechanism of Axon Guidance and Peripheral Nerve Regeneration," The Journal of biological chemistry 291(3): 1092-1102.

Lillis, A. P., et al., Feb. 14, 2023, "LDL receptor-related protein 1 : unique tissue-specific functions revealed by selective gene knockout studies," Physiol Rev 88(3): 887-918.

Mantuano, E., et al., 2015, "The NMDA receptor functions independently and as an LRP1 co-receptor to promote Schwann cell survival and migration," Journal of Cell Science 128(18): 3478-3488.

Matsuyama, S., et al., Mar. 31, 2020, "Enhanced isolation of SARS-COV-2 by TMPRSS2- expressing cells," Proceedings of the National Academy of Sciences 117(13): 7001.

May, P., et al., Aug. 21, 2013, "Low density receptor-related protein 1 (LRP1) promotes anti-inflammatory phenotype in murine macrophages," Cell Tissue Res 354(3): 887-889.

May, P., Apr. 2013, "The low-density lipoprotein receptor-related protein 1 in inflammation," Curr Opin Lipidol 24(2): 134-137.

Mehta, P., et al., Mar. 13, 2020, "COVID-19: consider cytokine storm syndromes and immunosuppression," The Lancet 395(10229): 1033-1034.

Meyer, M., et al., Apr. 17, 2015, "Respiratory protease/antiprotease balance determines susceptibility to viral infection and can be modified by nutritional antioxidants," American journal of physiology. Lunch cellular and molecular physiology 308(12): L1189-L1201.

Mishra, A., et al., Dec. 21, 2017, "Low-density lipoprotein receptor-related protein 1 attenuates house dust mite-induced eosinophilic airway inflammation by suppressing dendritic cell-mediated adaptive immune responses," Journal of Allergy and Clinical Immunology 142(4): 1066-1079.e1066.

Muehlenbein, M. P., et al., Mar. 29, 2006, "Testosterone correlates with Venezuelan equine encephalitis virus infection in macaques," Virol J 3: 19.

Oliva, K.J., et al., 2005, "The ecology of emerging neurotropic viruses," Journal of Neurovirology 11(5): 441-446.

Rauch, J. N., et al., Apr. 1, 2020, "LRP1 is a master regulator of tau uptake and spread," Nature 580(7803): 381-385.

Ronca, S. E., et al., Jun. 20, 2016, "Neurological Sequelae Resulting from Encephalitic Alphavirus Infection," Front Microbiol 7: 959.

Schoneboom, B. A., et al., 2000, "Early expression of IFN-alpha/beta and INOS in the brains of Venezuelan equine encephalitis virus-infected mice," J Interferon Cytokine Res 20(2): 205- 215.

Schoneboom, B. A., et al., 2000, "Inflammation is a component of neurodegeneration in response to Venezuelan equine encephalitis virus infection in mice," J Neuroimmunol 109(2): 132-146.

Sharma, A., et al., 2011, "Role of adhesion molecules and inflammation in Venezuelan equine encephalitis virus infected mouse brain," Virology Journal 8: 197-197.

Sharma, A. B., et al., Jun. 16, 2008, "Venezuelan equine encephalitis virus infection causes modulation of inflammatory and immune response genes in mouse brain," BMC Genomics 9: 289.

Shi, Y., et al., Apr. 28, 2009, "Ligand binding to LRP1 transactivates Trk receptors by a Src family kinase-dependent pathway," Sci Signal 2(68): ra18.

Shi, Y., et al., Apr. 2011, "Regulation of cytokine expression by Schwann cells in response to alpha2-macroglobulin binding to LRP1," J Neurosci Res 89(4): 544-551.

Shiga, Y., et al., 2019, "Tissue-type plasminogen activator-primed human iPSC-derived neural progenitor cells promote motor recovery after severe spinal cord injury," Scientific Reports 9(1): 19291.

Simon, D., et al., Jul. 16, 2017, "Evidence of an abnormal epithelial barrier in active, untreated and corticosteroid-treated eosinophilic esophagitis," Allergy 73(1): 239-247.

Steele, K. E., et al., 2010, "Review Paper: pathology of animal models of alphavirus encephalitis," Vet Pathol 47(5): 790-805.

Strickland, D. K., et al., 2011, "Serpin-Enzyme Receptors LDL Receptor-Related Protein 1," Methods Enzymol 499: 17-31.

Subramaniyam, D., et al., Nov. 18, 2005, "C-36 peptide, a degradation product of alpha1-antitrypsin, modulates human monocyte activation through LPS signaling pathways," Int J Biochem Cell Biol 38(4): 563-575.

Taylor, K. G., et al., 2013, "Pathogenesis of Venezuelan equine encephalitis," Vet Microbiol 167(1-2): 145-150.

Toldo, S., et al., 2017, "Low-Density Lipoprotein Receptor-Related Protein-1 Is a Therapeutic Target in Acute Myocardial Infarction," JACC Basic Transl Sci 2(5): 561-574.

Wang, Y., et al., Feb. 13, 2018, "Autophagy in Negative-Strand RNA Virus Infection," Frontiers in Microbiology 9(206).

Weaver, S. C., et al., 2004, "Venezuelan equine encephalitis," Annu Rev Entomol 49: 141- 174.

Wujak, L., et al., Aug. 1, 2018, "LRP1: A chameleon receptor of lung inflammation and repair," Matrix Biology 68-69: 366-381.

Wujak, L. P., et al., 2016, "The low density lipoprotein receptor-related protein (LRP) 1 and its function in lung diseases," Histol Histopathol 31(7): 733-745.

Yang, L., et al., 2016, "LRP1 modulates the microglial immune response via regulation of JNK and NF-KB signaling pathways," Journal of Neuroinflammation 13(1): 304.

Yang, X., et al., 2020, "Clinical course and outcomes of critically ill patients with SARS-COV-2 pneumonia in Wuhan, China: a single-centered, retrospective, observational study," The Lancet Respiratory Medicine, 8(5): 475-481.

Yoon, C., et al., Sep. 13, 2013, "Low-density Lipoprotein Receptor-related Protein 1 (LRP1)-dependent Cell Signaling Promotes Axonal Regeneration," Journal of Biological Chemistry 288(37): 26557-26568.

Zlokovic, B. V., et al., 2010, "Low-density lipoprotein receptor-related protein-1: a serial clearance homeostatic mechanism controlling Alzheimer's amyloid ß-peptide elimination from the brain," 115(5): 1077-1089.

Zurhove, K., et al., Nov. 25, 2008, "Gamma-secretase limits the inflammatory response through the processing of LRP1," Science signaling 1(47): ra15-ra15.

\* cited by examiner

Figure 6A
Figure 6B
Figure 6C
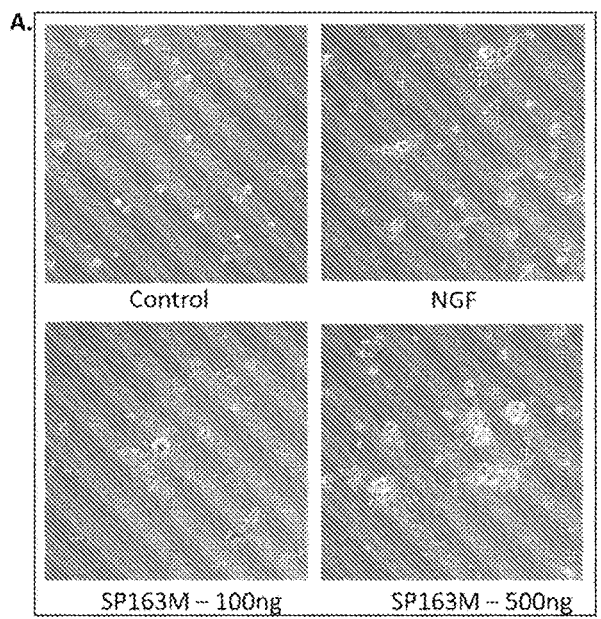
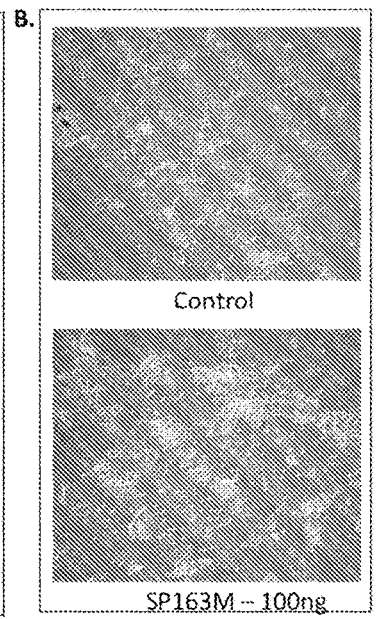
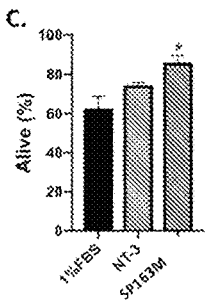

Figure 9A
Figure 9B
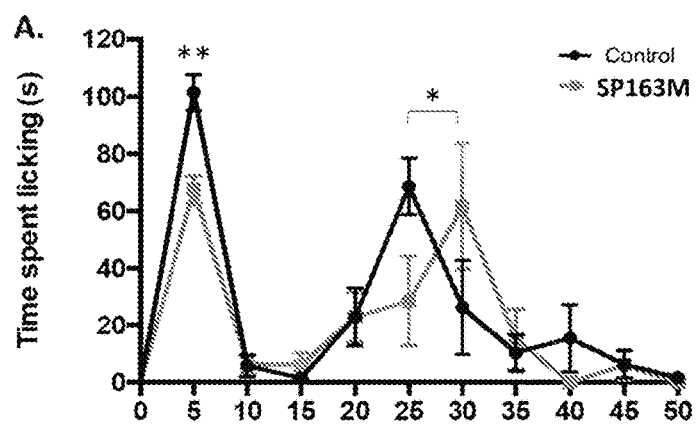
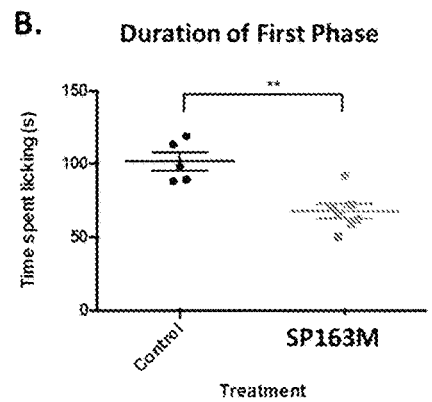
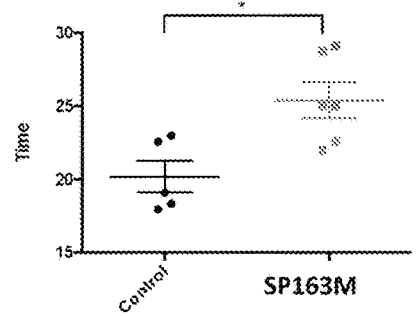
Figure 9C

Figure 16A
Figure 16B
Figure 16C
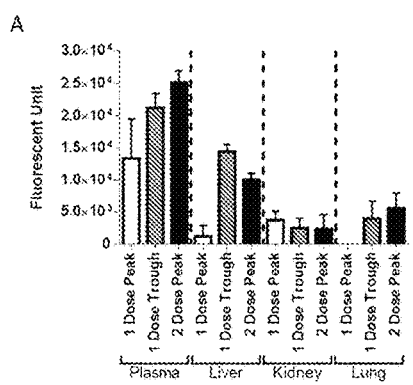
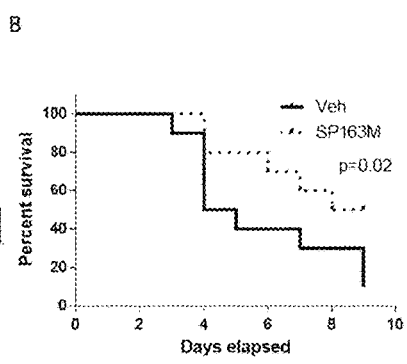
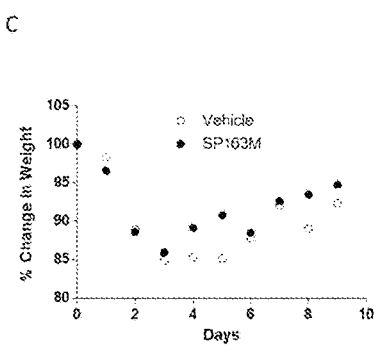

Figure 19A
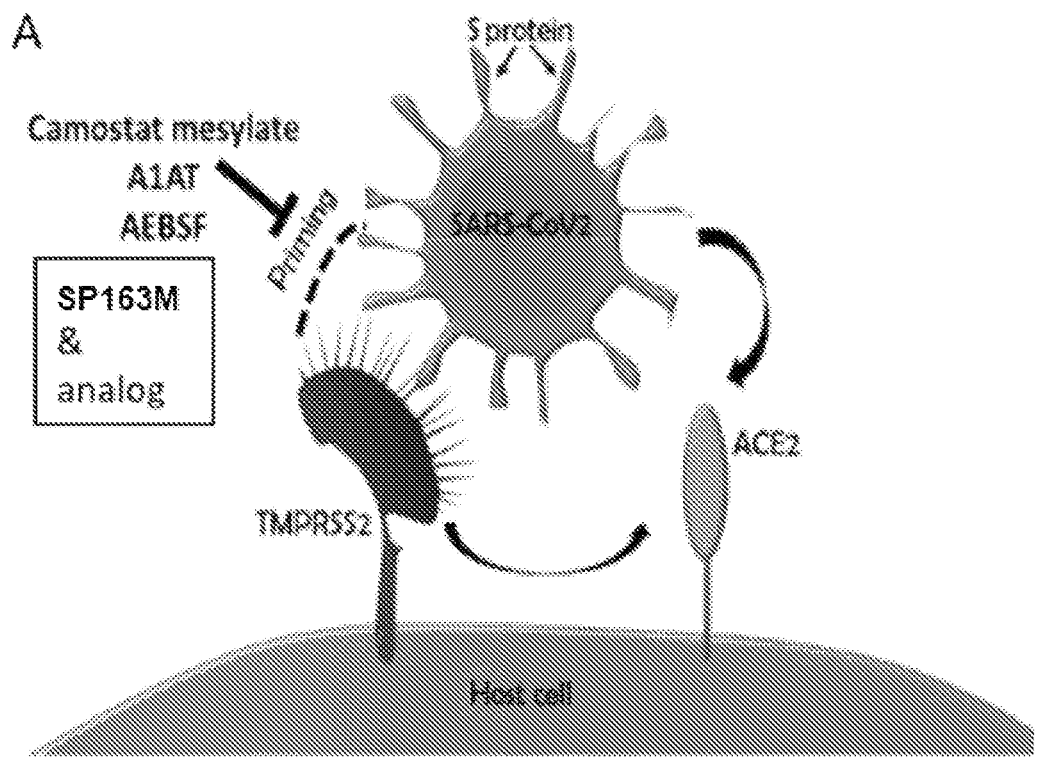
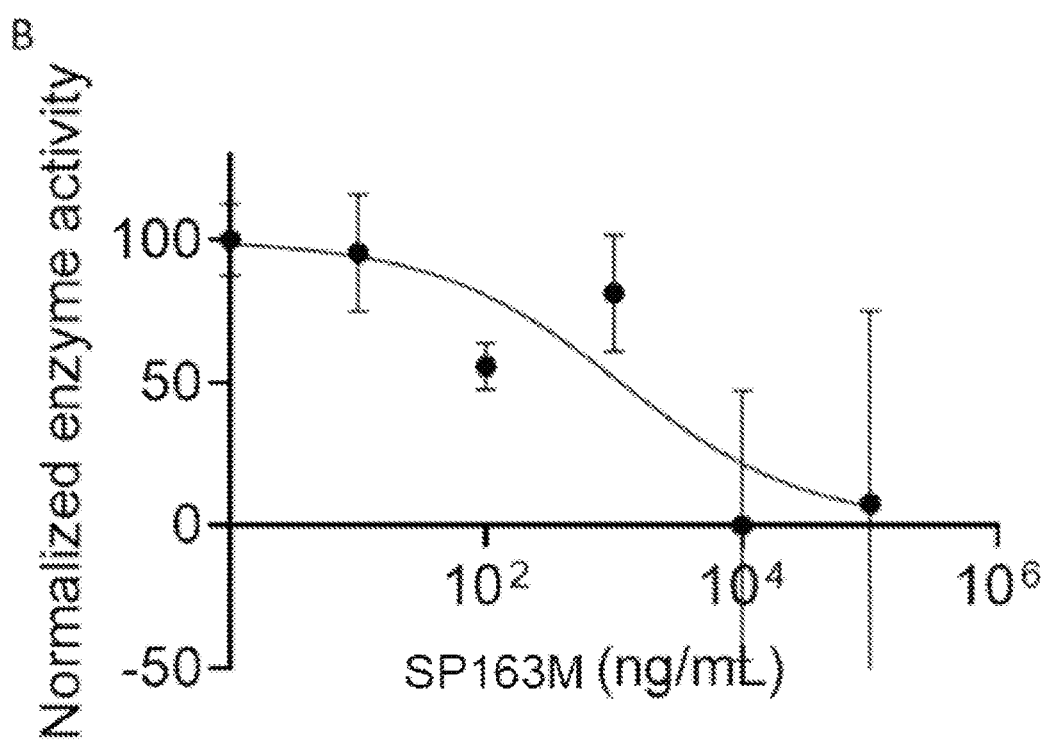
Figure 19B

Figure 20A
Figure 20B
Figure 20C
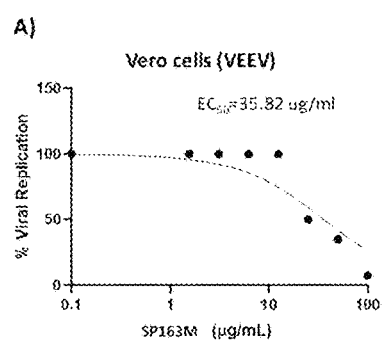
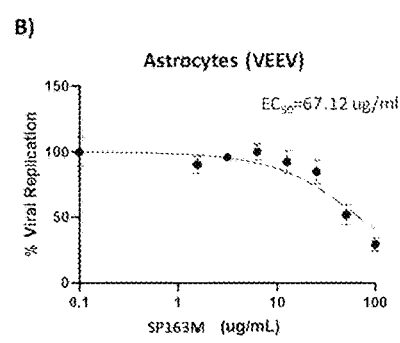
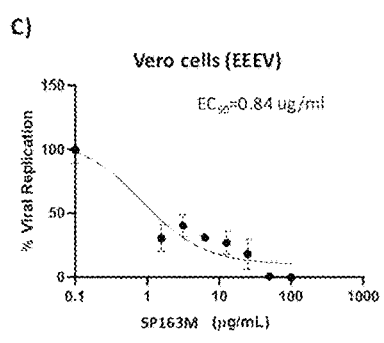

Figure 26A
Figure 26B
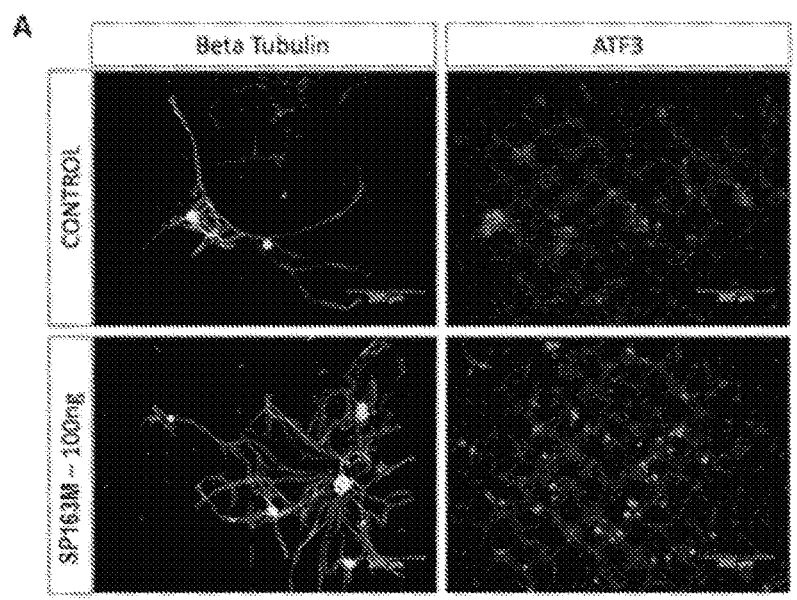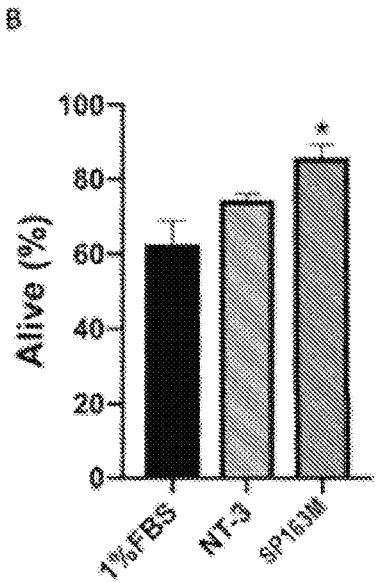

SEQUENCE LISTING

<160> NUMBER OF SEQ ID NOS: 46

<210> SEQ ID NO 1
<211> LENGTH: 9
<212> TYPE: PRT
<213> ORGANISM: Homo sapiens

<400> SEQUENCE: 1

Phe Asn Lys Pro Phe Val Phe Leu Met
1               5

<210> SEQ ID NO 2
<211> LENGTH: 17
<212> TYPE: PRT
<213> ORGANISM: Homo sapiens

<400> SEQUENCE: 2

Val Lys Phe Asn Lys Pro Phe Val Phe Leu Met Ile Glu Gln Asn Thr
1               5                   10                  15

Lys

<210> SEQ ID NO 3
<211> LENGTH: 5
<212> TYPE: PRT
<213> ORGANISM: Homo sapiens

<400> SEQUENCE: 3

Phe Val Phe Leu Met
1               5

<210> SEQ ID NO 4
<211> LENGTH: 9
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=R or F
<220> FEATURE:
<221> NAME/KEY: MISC_FEATURE
<222> LOCATION: (3)..(3)
<223> OTHER INFORMATION: X=K or R
<220> FEATURE:
<221> NAME/KEY: MISC_FEATURE
<222> LOCATION: (6)..(6)
<223> OTHER INFORMATION: X=V or L
<220> FEATURE:
<221> NAME/KEY: MISC_FEATURE
<222> LOCATION: (7)..(7)
<223> OTHER INFORMATION: X=F, V or I
<220> FEATURE:
<221> NAME/KEY: MISC_FEATURE
<222> LOCATION: (8)..(8)
<223> OTHER INFORMATION: X=L, V or I
<220> FEATURE:
<221> NAME/KEY: MISC_FEATURE
<222> LOCATION: (9)..(9)
<223> OTHER INFORMATION: X= M, I, or Nle

<400> SEQUENCE: 4

Xaa Asn Xaa Pro Phe Xaa Xaa Xaa Xaa
1               5

<210> SEQ ID NO 5
<211> LENGTH: 9
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (9)..(9)
<223> OTHER INFORMATION: Nle

```
<400> SEQUENCE: 5

Phe Asn Lys Pro Phe Val Phe Leu Xaa
1               5

<210> SEQ ID NO 6
<211> LENGTH: 9
<212> TYPE: PRT
<213> ORGANISM: Artificial Sequence
<220> FEATURE:
<223> OTHER INFORMATION: peptide derivative

<400> SEQUENCE: 6

Phe Asn Arg Pro Phe Leu Val Val Ile
1               5

<210> SEQ ID NO 7
<211> LENGTH: 9
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (9)..(9)
<223> OTHER INFORMATION: Nle

<400> SEQUENCE: 7

Phe Asn Arg Pro Phe Leu Val Val Xaa
1               5

<210> SEQ ID NO 8
<211> LENGTH: 9
<212> TYPE: PRT
<213> ORGANISM: Artificial Sequence
<220> FEATURE:
<223> OTHER INFORMATION: peptide derivative

<400> SEQUENCE: 8

Phe Asn Arg Pro Phe Leu Met Ile Ile
1               5

<210> SEQ ID NO 9
<211> LENGTH: 9
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (9)..(9)
<223> OTHER INFORMATION: Nle

<400> SEQUENCE: 9

Phe Asn Arg Pro Phe Leu Val Ile Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (5)..(5)
<223> OTHER INFORMATION: Nle

<400> SEQUENCE: 10
```

```
Phe Val Phe Leu Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: peptide derivative

<400> SEQUENCE: 11

Phe Leu Val Val Ile
1               5

<210> SEQ ID NO 12
<211> LENGTH: 5
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (5)..(5)
<223> OTHER INFORMATION: Nle

<400> SEQUENCE: 12

Phe Leu Val Val Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: peptide derivative

<400> SEQUENCE: 13

Phe Leu Met Ile Ile
1               5

<210> SEQ ID NO 14
<211> LENGTH: 5
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (5)..(5)
<223> OTHER INFORMATION: Nle

<400> SEQUENCE: 14

Phe Leu Met Ile Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (2)..(2)
<223> OTHER INFORMATION: X=V or L
<220> FEATURE:
<221> NAME/KEY: MISC_FEATURE
<222> LOCATION: (3)..(3)
<223> OTHER INFORMATION: X=F, V or M
<220> FEATURE:
```

<220> FEATURE:
<221> NAME/KEY: MISC_FEATURE
<222> LOCATION: (4)..(4)
<223> OTHER INFORMATION: X= L, V or I
<220> FEATURE:
<221> NAME/KEY: MISC_FEATURE
<222> LOCATION: (5)..(5)
<223> OTHER INFORMATION: X= M, I, or Nle

<400> SEQUENCE: 15

Phe Xaa Xaa Xaa Xaa
1               5

<210> SEQ ID NO 16
<211> LENGTH: 31
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=any basic amino acid or absent
<220> FEATURE:
<221> NAME/KEY: MISC_FEATURE
<222> LOCATION: (2)..(2)
<223> OTHER INFORMATION: X=any basic amino acid or absent
<220> FEATURE:
<221> NAME/KEY: MISC_FEATURE
<222> LOCATION: (3)..(3)
<223> OTHER INFORMATION: X=any basic amino acid or absent
<220> FEATURE:
<221> NAME/KEY: MISC_FEATURE
<222> LOCATION: (4)..(4)
<223> OTHER INFORMATION: X=any basic amino acid or absent
<220> FEATURE:
<221> NAME/KEY: MISC_FEATURE
<222> LOCATION: (5)..(5)
<223> OTHER INFORMATION: X=any basic amino acid or absent
<220> FEATURE:
<221> NAME/KEY: MISC_FEATURE
<222> LOCATION: (6)..(6)
<223> OTHER INFORMATION: X=any basic amino acid or absent
<220> FEATURE:
<221> NAME/KEY: MISC_FEATURE
<222> LOCATION: (7)..(7)
<223> OTHER INFORMATION: X=any basic amino acid or absent
<220> FEATURE:
<221> NAME/KEY: MISC_FEATURE
<222> LOCATION: (8)..(8)
<223> OTHER INFORMATION: X=any basic amino acid or absent
<220> FEATURE:
<221> NAME/KEY: MISC_FEATURE
<222> LOCATION: (9)..(9)
<223> OTHER INFORMATION: X=any basic amino acid or absent
<220> FEATURE:
<221> NAME/KEY: MISC_FEATURE
<222> LOCATION: (10)..(10)
<223> OTHER INFORMATION: X=any basic amino acid
<220> FEATURE:
<221> NAME/KEY: MISC_FEATURE
<222> LOCATION: (12)..(12)
<223> OTHER INFORMATION: X=R or F
<220> FEATURE:
<221> NAME/KEY: MISC_FEATURE
<222> LOCATION: (14)..(14)
<223> OTHER INFORMATION: X=K or R
<220> FEATURE:
<221> NAME/KEY: MISC_FEATURE
<222> LOCATION: (17)..(17)
<223> OTHER INFORMATION: X=V or L
<220> FEATURE:
<221> NAME/KEY: MISC_FEATURE
<222> LOCATION: (18)..(18)
<223> OTHER INFORMATION: X=F, V or M
<220> FEATURE:
<221> NAME/KEY: MISC_FEATURE
<222> LOCATION: (19)..(19)

```
<223> OTHER INFORMATION: X=L, V or I
<220> FEATURE:
<221> NAME/KEY: MISC_FEATURE
<222> LOCATION: (20)..(20)
<223> OTHER INFORMATION: X=M, I, or Nle
<220> FEATURE:
<221> NAME/KEY: MISC_FEATURE
<222> LOCATION: (22)..(22)
<223> OTHER INFORMATION: X=any basic amino acid
<220> FEATURE:
<221> NAME/KEY: MISC_FEATURE
<222> LOCATION: (23)..(23)
<223> OTHER INFORMATION: X=any basic amino acid or absent
<220> FEATURE:
<221> NAME/KEY: MISC_FEATURE
<222> LOCATION: (24)..(24)
<223> OTHER INFORMATION: X=any basic amino acid or absent
<220> FEATURE:
<221> NAME/KEY: MISC_FEATURE
<222> LOCATION: (25)..(25)
<223> OTHER INFORMATION: X=any basic amino acid or absent
<220> FEATURE:
<221> NAME/KEY: MISC_FEATURE
<222> LOCATION: (26)..(26)
<223> OTHER INFORMATION: X=any basic amino acid or absent
<220> FEATURE:
<221> NAME/KEY: MISC_FEATURE
<222> LOCATION: (27)..(27)
<223> OTHER INFORMATION: X=any basic amino acid or absent
<220> FEATURE:
<221> NAME/KEY: MISC_FEATURE
<222> LOCATION: (28)..(28)
<223> OTHER INFORMATION: X=any basic amino acid or absent
<220> FEATURE:
<221> NAME/KEY: MISC_FEATURE
<222> LOCATION: (29)..(29)
<223> OTHER INFORMATION: X=any basic amino acid or absent
<220> FEATURE:
<221> NAME/KEY: MISC_FEATURE
<222> LOCATION: (30)..(30)
<223> OTHER INFORMATION: X=any basic amino acid or absent
<220> FEATURE:
<221> NAME/KEY: MISC_FEATURE
<222> LOCATION: (31)..(31)
<223> OTHER INFORMATION: X=any basic amino acid or absent

<400> SEQUENCE: 16

Xaa Xaa Xaa Xaa Xaa Xaa Xaa Xaa Xaa Xaa Arg Xaa Asn Xaa Pro Phe
1               5                   10                  15

Xaa Xaa Xaa Xaa Arg Xaa Xaa Xaa Xaa Xaa Xaa Xaa Xaa Xaa Xaa
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=any basic amino acid or absent
<220> FEATURE:
<221> NAME/KEY: MISC_FEATURE
<222> LOCATION: (2)..(2)
<223> OTHER INFORMATION: X=any basic amino acid or absent
<220> FEATURE:
<221> NAME/KEY: MISC_FEATURE
<222> LOCATION: (3)..(3)
<223> OTHER INFORMATION: X=any basic amino acid or absent
<220> FEATURE:
<221> NAME/KEY: MISC_FEATURE
<222> LOCATION: (4)..(4)
<223> OTHER INFORMATION: X=any basic amino acid or absent
<220> FEATURE:
<221> NAME/KEY: MISC_FEATURE
```

```
<222> LOCATION: (5)..(5)
<223> OTHER INFORMATION: X=any basic amino acid or absent
<220> FEATURE:
<221> NAME/KEY: MISC_FEATURE
<222> LOCATION: (6)..(6)
<223> OTHER INFORMATION: X=any basic amino acid or absent
<220> FEATURE:
<221> NAME/KEY: MISC_FEATURE
<222> LOCATION: (7)..(7)
<223> OTHER INFORMATION: X=any basic amino acid or absent
<220> FEATURE:
<221> NAME/KEY: MISC_FEATURE
<222> LOCATION: (8)..(8)
<223> OTHER INFORMATION: X=any basic amino acid or absent
<220> FEATURE:
<221> NAME/KEY: MISC_FEATURE
<222> LOCATION: (9)..(9)
<223> OTHER INFORMATION: X=any basic amino acid or absent
<220> FEATURE:
<221> NAME/KEY: MISC_FEATURE
<222> LOCATION: (10)..(10)
<223> OTHER INFORMATION: X=any basic amino acid
<220> FEATURE:
<221> NAME/KEY: MISC_FEATURE
<222> LOCATION: (22)..(22)
<223> OTHER INFORMATION: X=any basic amino acid
<220> FEATURE:
<221> NAME/KEY: MISC_FEATURE
<222> LOCATION: (23)..(23)
<223> OTHER INFORMATION: X=any basic amino acid or absent
<220> FEATURE:
<221> NAME/KEY: MISC_FEATURE
<222> LOCATION: (24)..(24)
<223> OTHER INFORMATION: X=any basic amino acid or absent
<220> FEATURE:
<221> NAME/KEY: MISC_FEATURE
<222> LOCATION: (25)..(25)
<223> OTHER INFORMATION: X=any basic amino acid or absent
<220> FEATURE:
<221> NAME/KEY: MISC_FEATURE
<222> LOCATION: (26)..(26)
<223> OTHER INFORMATION: X=any basic amino acid or absent
<220> FEATURE:
<221> NAME/KEY: MISC_FEATURE
<222> LOCATION: (27)..(27)
<223> OTHER INFORMATION: X=any basic amino acid or absent
<220> FEATURE:
<221> NAME/KEY: MISC_FEATURE
<222> LOCATION: (28)..(28)
<223> OTHER INFORMATION: X=any basic amino acid or absent
<220> FEATURE:
<221> NAME/KEY: MISC_FEATURE
<222> LOCATION: (29)..(29)
<223> OTHER INFORMATION: X=any basic amino acid or absent
<220> FEATURE:
<221> NAME/KEY: MISC_FEATURE
<222> LOCATION: (30)..(30)
<223> OTHER INFORMATION: X=any basic amino acid or absent
<220> FEATURE:
<221> NAME/KEY: MISC_FEATURE
<222> LOCATION: (31)..(31)
<223> OTHER INFORMATION: X=any basic amino acid or absent

<400> SEQUENCE: 17

Xaa Xaa Xaa Xaa Xaa Xaa Xaa Xaa Xaa Xaa Arg Phe Asn Arg Pro Phe
1               5                   10                  15

Leu Val Val Ile Arg Xaa Xaa Xaa Xaa Xaa Xaa Xaa Xaa Xaa
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: peptide derivative
<220> FEATURE:
```

```
<221> NAME/KEY: MISC_FEATURE
<222> LOCATION: (1)..(1)
<223> OTHER INFORMATION: X=any basic amino acid or absent
<220> FEATURE:
<221> NAME/KEY: MISC_FEATURE
<222> LOCATION: (2)..(2)
<223> OTHER INFORMATION: X=any basic amino acid or absent
<220> FEATURE:
<221> NAME/KEY: MISC_FEATURE
<222> LOCATION: (3)..(3)
<223> OTHER INFORMATION: X=any basic amino acid or absent
<220> FEATURE:
<221> NAME/KEY: MISC_FEATURE
<222> LOCATION: (4)..(4)
<223> OTHER INFORMATION: X=any basic amino acid or absent
<220> FEATURE:
<221> NAME/KEY: MISC_FEATURE
<222> LOCATION: (5)..(5)
<223> OTHER INFORMATION: X=any basic amino acid or absent
<220> FEATURE:
<221> NAME/KEY: MISC_FEATURE
<222> LOCATION: (6)..(6)
<223> OTHER INFORMATION: X=any basic amino acid or absent
<220> FEATURE:
<221> NAME/KEY: MISC_FEATURE
<222> LOCATION: (7)..(7)
<223> OTHER INFORMATION: X=any basic amino acid or absent
<220> FEATURE:
<221> NAME/KEY: MISC_FEATURE
<222> LOCATION: (8)..(8)
<223> OTHER INFORMATION: X=any basic amino acid or absent
<220> FEATURE:
<221> NAME/KEY: MISC_FEATURE
<222> LOCATION: (9)..(9)
<223> OTHER INFORMATION: X=any basic amino acid or absent
<220> FEATURE:
<221> NAME/KEY: MISC_FEATURE
<222> LOCATION: (10)..(10)
<223> OTHER INFORMATION: X=any basic amino acid
<220> FEATURE:
<221> NAME/KEY: MISC_FEATURE
<222> LOCATION: (22)..(22)
<223> OTHER INFORMATION: X= any basic amino acid
<220> FEATURE:
<221> NAME/KEY: MISC_FEATURE
<222> LOCATION: (23)..(23)
<223> OTHER INFORMATION: X= any basic amino acid or absent
<220> FEATURE:
<221> NAME/KEY: MISC_FEATURE
<222> LOCATION: (24)..(24)
<223> OTHER INFORMATION: X= any basic amino acid or absent
<220> FEATURE:
<221> NAME/KEY: MISC_FEATURE
<222> LOCATION: (25)..(25)
<223> OTHER INFORMATION: X= any basic amino acid or absent
<220> FEATURE:
<221> NAME/KEY: MISC_FEATURE
<222> LOCATION: (26)..(26)
<223> OTHER INFORMATION: X= any basic amino acid or absent
<220> FEATURE:
<221> NAME/KEY: MISC_FEATURE
<222> LOCATION: (27)..(27)
<223> OTHER INFORMATION: X= any basic amino acid or absent
<220> FEATURE:
<221> NAME/KEY: MISC_FEATURE
<222> LOCATION: (28)..(28)
<223> OTHER INFORMATION: X= any basic amino acid or absent
<220> FEATURE:
<221> NAME/KEY: MISC_FEATURE
<222> LOCATION: (29)..(29)
<223> OTHER INFORMATION: X= any basic amino acid or absent
<220> FEATURE:
<221> NAME/KEY: MISC_FEATURE
<222> LOCATION: (30)..(30)
<223> OTHER INFORMATION: X= any basic amino acid or absent
<220> FEATURE:
<221> NAME/KEY: MISC_FEATURE
<222> LOCATION: (31)..(31)
<223> OTHER INFORMATION: X= any basic amino acid or absent
```

<400> SEQUENCE: 18

Xaa Xaa Xaa Xaa Xaa Xaa Xaa Xaa Xaa Xaa Arg Phe Asn Arg Pro Phe
1               5                   10                  15

Leu Met Ile Ile Arg Xaa Xaa Xaa Xaa Xaa Xaa Xaa Xaa Xaa
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=any basic amino acid or absent
<220> FEATURE:
<221> NAME/KEY: MISC_FEATURE
<222> LOCATION: (2)..(2)
<223> OTHER INFORMATION: X=any basic amino acid or absent
<220> FEATURE:
<221> NAME/KEY: MISC_FEATURE
<222> LOCATION: (3)..(3)
<223> OTHER INFORMATION: X=any basic amino acid or absent
<220> FEATURE:
<221> NAME/KEY: MISC_FEATURE
<222> LOCATION: (4)..(4)
<223> OTHER INFORMATION: X=any basic amino acid or absent
<220> FEATURE:
<221> NAME/KEY: MISC_FEATURE
<222> LOCATION: (5)..(5)
<223> OTHER INFORMATION: X=any basic amino acid or absent
<220> FEATURE:
<221> NAME/KEY: MISC_FEATURE
<222> LOCATION: (6)..(6)
<223> OTHER INFORMATION: X=any basic amino acid or absent
<220> FEATURE:
<221> NAME/KEY: MISC_FEATURE
<222> LOCATION: (7)..(7)
<223> OTHER INFORMATION: X=any basic amino acid or absent
<220> FEATURE:
<221> NAME/KEY: MISC_FEATURE
<222> LOCATION: (8)..(8)
<223> OTHER INFORMATION: X=any basic amino acid or absent
<220> FEATURE:
<221> NAME/KEY: MISC_FEATURE
<222> LOCATION: (9)..(9)
<223> OTHER INFORMATION: X=any basic amino acid or absent
<220> FEATURE:
<221> NAME/KEY: MISC_FEATURE
<222> LOCATION: (10)..(10)
<223> OTHER INFORMATION: X=any basic amino acid
<220> FEATURE:
<221> NAME/KEY: MOD_RES
<222> LOCATION: (20)..(20)
<223> OTHER INFORMATION: Nle
<220> FEATURE:
<221> NAME/KEY: MISC_FEATURE
<222> LOCATION: (22)..(22)
<223> OTHER INFORMATION: X=any basic amino acid
<220> FEATURE:
<221> NAME/KEY: MISC_FEATURE
<222> LOCATION: (23)..(23)
<223> OTHER INFORMATION: X=any basic amino acid or absent
<220> FEATURE:
<221> NAME/KEY: MISC_FEATURE
<222> LOCATION: (24)..(24)
<223> OTHER INFORMATION: X=any basic amino acid or absent
<220> FEATURE:
<221> NAME/KEY: MISC_FEATURE
<222> LOCATION: (25)..(25)
<223> OTHER INFORMATION: X=any basic amino acid or absent
<220> FEATURE:
<221> NAME/KEY: MISC_FEATURE
<222> LOCATION: (26)..(26)

<223> OTHER INFORMATION: X=any basic amino acid or absent
<220> FEATURE:
<221> NAME/KEY: MISC_FEATURE
<222> LOCATION: (27)..(27)
<223> OTHER INFORMATION: X=any basic amino acid or absent
<220> FEATURE:
<221> NAME/KEY: MISC_FEATURE
<222> LOCATION: (28)..(28)
<223> OTHER INFORMATION: X=any basic amino acid or absent
<220> FEATURE:
<221> NAME/KEY: MISC_FEATURE
<222> LOCATION: (29)..(29)
<223> OTHER INFORMATION: X=any basic amino acid or absent
<220> FEATURE:
<221> NAME/KEY: MISC_FEATURE
<222> LOCATION: (30)..(30)
<223> OTHER INFORMATION: X=any basic amino acid or absent
<220> FEATURE:
<221> NAME/KEY: MISC_FEATURE
<222> LOCATION: (31)..(31)
<223> OTHER INFORMATION: X=any basic amino acid or absent

<400> SEQUENCE: 19

Xaa Xaa Xaa Xaa Xaa Xaa Xaa Xaa Xaa Xaa Lys Phe Asn Lys Pro Phe
1               5                   10                  15

Val Phe Leu Xaa Arg Xaa Xaa Xaa Xaa Xaa Xaa Xaa Xaa Xaa
            20                  25                  30

<210> SEQ ID NO 20
<211> LENGTH: 16
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=V or L
<220> FEATURE:
<221> NAME/KEY: MISC_FEATURE
<222> LOCATION: (2)..(2)
<223> OTHER INFORMATION: X=any amino acid
<220> FEATURE:
<221> NAME/KEY: MISC_FEATURE
<222> LOCATION: (3)..(3)
<223> OTHER INFORMATION: X=R or F
<220> FEATURE:
<221> NAME/KEY: MISC_FEATURE
<222> LOCATION: (4)..(4)
<223> OTHER INFORMATION: X=any amino acid
<220> FEATURE:
<221> NAME/KEY: MISC_FEATURE
<222> LOCATION: (5)..(5)
<223> OTHER INFORMATION: X=R or K
<220> FEATURE:
<221> NAME/KEY: MISC_FEATURE
<222> LOCATION: (6)..(6)
<223> OTHER INFORMATION: X=any amino acid
<220> FEATURE:
<221> NAME/KEY: MISC_FEATURE
<222> LOCATION: (11)..(11)
<223> OTHER INFORMATION: X=M, Nle, or I
<220> FEATURE:
<221> NAME/KEY: MISC_FEATURE
<222> LOCATION: (12)..(12)
<223> OTHER INFORMATION: X=any amino acid
<220> FEATURE:
<221> NAME/KEY: MISC_FEATURE
<222> LOCATION: (13)..(13)
<223> OTHER INFORMATION: X=any amino acid
<220> FEATURE:
<221> NAME/KEY: MISC_FEATURE
<222> LOCATION: (14)..(14)
<223> OTHER INFORMATION: X=any amino acid
<220> FEATURE:
<221> NAME/KEY: MISC_FEATURE

```
<222> LOCATION: (15)..(15)
<223> OTHER INFORMATION: X=any amino acid
<220> FEATURE:
<221> NAME/KEY: MISC_FEATURE
<222> LOCATION: (16)..(16)
<223> OTHER INFORMATION: X=any amino acid

<400> SEQUENCE: 20

Xaa Xaa Xaa Xaa Xaa Xaa Phe Val Phe Leu Xaa Xaa Xaa Xaa Xaa Xaa
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=V or L
<220> FEATURE:
<221> NAME/KEY: MISC_FEATURE
<222> LOCATION: (2)..(2)
<223> OTHER INFORMATION: X=any amino acid
<220> FEATURE:
<221> NAME/KEY: MISC_FEATURE
<222> LOCATION: (3)..(3)
<223> OTHER INFORMATION: X=F or R
<220> FEATURE:
<221> NAME/KEY: MISC_FEATURE
<222> LOCATION: (4)..(4)
<223> OTHER INFORMATION: X=any amino acid
<220> FEATURE:
<221> NAME/KEY: MISC_FEATURE
<222> LOCATION: (5)..(5)
<223> OTHER INFORMATION: X=any amino acid
<220> FEATURE:
<221> NAME/KEY: MISC_FEATURE
<222> LOCATION: (6)..(6)
<223> OTHER INFORMATION: X=K or R
<220> FEATURE:
<221> NAME/KEY: MISC_FEATURE
<222> LOCATION: (7)..(7)
<223> OTHER INFORMATION: X=any amino acid
<220> FEATURE:
<221> NAME/KEY: MISC_FEATURE
<222> LOCATION: (9)..(9)
<223> OTHER INFORMATION: X=V, L, or M
<220> FEATURE:
<221> NAME/KEY: MISC_FEATURE
<222> LOCATION: (12)..(12)
<223> OTHER INFORMATION: X=M, Nle, or I
<220> FEATURE:
<221> NAME/KEY: MISC_FEATURE
<222> LOCATION: (13)..(13)
<223> OTHER INFORMATION: X=any amino acid
<220> FEATURE:
<221> NAME/KEY: MISC_FEATURE
<222> LOCATION: (14)..(14)
<223> OTHER INFORMATION: X=any amino acid
<220> FEATURE:
<221> NAME/KEY: MISC_FEATURE
<222> LOCATION: (15)..(15)
<223> OTHER INFORMATION: X=any amino acid
<220> FEATURE:
<221> NAME/KEY: MISC_FEATURE
<222> LOCATION: (16)..(16)
<223> OTHER INFORMATION: X=any amino acid
<220> FEATURE:
<221> NAME/KEY: MISC_FEATURE
<222> LOCATION: (17)..(17)
<223> OTHER INFORMATION: X=any amino acid

<400> SEQUENCE: 21

Xaa Xaa Xaa Xaa Xaa Xaa Xaa Phe Xaa Phe Leu Xaa Xaa Xaa Xaa Xaa
```

```
1               5                   10                  15

Xaa

<210> SEQ ID NO 22
<211> LENGTH: 21
<212> TYPE: PRT
<213> ORGANISM: Artificial Sequence
<220> FEATURE:
<223> OTHER INFORMATION: peptide derivative

<400> SEQUENCE: 22

Phe Pro Lys Met Val Pro Gln Phe Asn Thr Glu Leu Lys Ile Phe Pro
1               5                   10                  15

Glu Val Asn Ile Lys
            20

<210> SEQ ID NO 23
<211> LENGTH: 33
<212> TYPE: PRT
<213> ORGANISM: Homo sapiens

<400> SEQUENCE: 23

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro

<210> SEQ ID NO 24
<211> LENGTH: 17
<212> TYPE: PRT
<213> ORGANISM: Homo sapiens

<400> SEQUENCE: 24

Val Lys Phe Asn Lys Pro Phe Val Phe Leu Met Ile Glu Gln Asn Thr
1               5                   10                  15

Lys

<210> SEQ ID NO 25
<211> LENGTH: 11
<212> TYPE: PRT
<213> ORGANISM: Homo sapiens

<400> SEQUENCE: 25

Val Lys Phe Asn Lys Pro Phe Val Phe Leu Met
1               5                   10

<210> SEQ ID NO 26
<211> LENGTH: 23
<212> TYPE: PRT
<213> ORGANISM: Artificial Sequence
<220> FEATURE:
<223> OTHER INFORMATION: peptide derivative

<400> SEQUENCE: 26

Arg Arg Arg Val Lys Phe Asn Lys Pro Phe Val Phe Leu Met Ile Glu
1               5                   10                  15

Gln Asn Thr Lys Arg Arg Arg
            20

<210> SEQ ID NO 27
<211> LENGTH: 17
```

```
<212> TYPE: PRT
<213> ORGANISM: Artificial Sequence
<220> FEATURE:
<223> OTHER INFORMATION: peptide derivative

<400> SEQUENCE: 27

Arg Arg Arg Val Lys Phe Asn Lys Pro Phe Val Phe Leu Met Arg Arg
1               5                   10                  15

Arg

<210> SEQ ID NO 28
<211> LENGTH: 17
<212> TYPE: PRT
<213> ORGANISM: Artificial Sequence
<220> FEATURE:
<223> OTHER INFORMATION: peptide derivative

<400> SEQUENCE: 28

Leu Arg Phe Asn Arg Pro Phe Leu Val Val Ile Phe Ser Thr Ser Thr
1               5                   10                  15

Gln

<210> SEQ ID NO 29
<211> LENGTH: 11
<212> TYPE: PRT
<213> ORGANISM: Artificial Sequence
<220> FEATURE:
<223> OTHER INFORMATION: peptide derivative

<400> SEQUENCE: 29

Leu Arg Phe Asn Arg Pro Phe Leu Val Val Ile
1               5                   10

<210> SEQ ID NO 30
<211> LENGTH: 17
<212> TYPE: PRT
<213> ORGANISM: Artificial Sequence
<220> FEATURE:
<223> OTHER INFORMATION: peptide derivative

<400> SEQUENCE: 30

Arg Arg Arg Leu Arg Phe Asn Arg Pro Phe Leu Val Val Ile Arg Arg
1               5                   10                  15

Arg

<210> SEQ ID NO 31
<211> LENGTH: 11
<212> TYPE: PRT
<213> ORGANISM: Artificial Sequence
<220> FEATURE:
<223> OTHER INFORMATION: peptide derivative

<400> SEQUENCE: 31

Val Arg Phe Asn Arg Pro Phe Leu Met Ile Ile
1               5                   10

<210> SEQ ID NO 32
<211> LENGTH: 17
<212> TYPE: PRT
<213> ORGANISM: Artificial Sequence
<220> FEATURE:
<223> OTHER INFORMATION: peptide derivative

<400> SEQUENCE: 32

Arg Arg Arg Val Arg Phe Asn Arg Pro Phe Leu Met Ile Ile Arg Arg
```

```
1               5                   10                  15
Arg

<210> SEQ ID NO 33
<211> LENGTH: 8
<212> TYPE: PRT
<213> ORGANISM: Artificial Sequence
<220> FEATURE:
<223> OTHER INFORMATION: peptide derivative

<400> SEQUENCE: 33

Val Arg Phe Asn Arg Pro Phe Leu
1               5

<210> SEQ ID NO 34
<211> LENGTH: 14
<212> TYPE: PRT
<213> ORGANISM: Artificial Sequence
<220> FEATURE:
<223> OTHER INFORMATION: peptide derivative

<400> SEQUENCE: 34

Arg Arg Arg Val Arg Phe Asn Arg Pro Phe Leu Arg Arg Arg
1               5                   10

<210> SEQ ID NO 35
<211> LENGTH: 17
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (11)..(11)
<223> OTHER INFORMATION: Nle

<400> SEQUENCE: 35

Val Lys Phe Asn Lys Pro Phe Val Phe Leu Xaa Ile Glu Gln Asn Thr
1               5                   10                  15
Lys

<210> SEQ ID NO 36
<211> LENGTH: 17
<212> TYPE: PRT
<213> ORGANISM: Artificial Sequence
<220> FEATURE:
<223> OTHER INFORMATION: peptide derivative

<400> SEQUENCE: 36

Val Lys Phe Asn Lys Ala Ala Ala Ala Ala Ala Ile Glu Gln Asn Thr
1               5                   10                  15
Lys

<210> SEQ ID NO 37
<211> LENGTH: 31
<212> TYPE: PRT
<213> ORGANISM: Artificial Sequence
<220> FEATURE:
<223> OTHER INFORMATION: peptide derivative
<220> FEATURE:
<221> NAME/KEY: MISC_FEATURE
<222> LOCATION: (1)..(1)
<223> OTHER INFORMATION: X=any amino acid or absent
<220> FEATURE:
<221> NAME/KEY: MISC_FEATURE
<222> LOCATION: (2)..(2)
<223> OTHER INFORMATION: X=any amino acid or absent
```

```
<220> FEATURE:
<221> NAME/KEY: MISC_FEATURE
<222> LOCATION: (3)..(3)
<223> OTHER INFORMATION: X=any amino acid or absent
<220> FEATURE:
<221> NAME/KEY: MISC_FEATURE
<222> LOCATION: (4)..(4)
<223> OTHER INFORMATION: X=any amino acid or absent
<220> FEATURE:
<221> NAME/KEY: MISC_FEATURE
<222> LOCATION: (5)..(5)
<223> OTHER INFORMATION: X=any amino acid or absent
<220> FEATURE:
<221> NAME/KEY: MISC_FEATURE
<222> LOCATION: (6)..(6)
<223> OTHER INFORMATION: X=any amino acid or absent
<220> FEATURE:
<221> NAME/KEY: MISC_FEATURE
<222> LOCATION: (7)..(7)
<223> OTHER INFORMATION: X=any amino acid or absent
<220> FEATURE:
<221> NAME/KEY: MISC_FEATURE
<222> LOCATION: (8)..(8)
<223> OTHER INFORMATION: X=any amino acid or absent
<220> FEATURE:
<221> NAME/KEY: MISC_FEATURE
<222> LOCATION: (9)..(9)
<223> OTHER INFORMATION: X=any amino acid or absent
<220> FEATURE:
<221> NAME/KEY: MISC_FEATURE
<222> LOCATION: (10)..(10)
<223> OTHER INFORMATION: X=any amino acid
<220> FEATURE:
<221> NAME/KEY: MOD_RES
<222> LOCATION: (20)..(20)
<223> OTHER INFORMATION: Nle
<220> FEATURE:
<221> NAME/KEY: MISC_FEATURE
<222> LOCATION: (22)..(22)
<223> OTHER INFORMATION: X=any amino acid or absent
<220> FEATURE:
<221> NAME/KEY: MISC_FEATURE
<222> LOCATION: (23)..(23)
<223> OTHER INFORMATION: X=any amino acid or absent
<220> FEATURE:
<221> NAME/KEY: MISC_FEATURE
<222> LOCATION: (24)..(24)
<223> OTHER INFORMATION: X=any amino acid or absent
<220> FEATURE:
<221> NAME/KEY: MISC_FEATURE
<222> LOCATION: (25)..(25)
<223> OTHER INFORMATION: X=any amino acid or absent
<220> FEATURE:
<221> NAME/KEY: MISC_FEATURE
<222> LOCATION: (26)..(26)
<223> OTHER INFORMATION: X=any amino acid or absent
<220> FEATURE:
<221> NAME/KEY: MISC_FEATURE
<222> LOCATION: (27)..(27)
<223> OTHER INFORMATION: X=any amino acid or absent
<220> FEATURE:
<221> NAME/KEY: MISC_FEATURE
<222> LOCATION: (28)..(28)
<223> OTHER INFORMATION: X=any amino acid or absent
<220> FEATURE:
<221> NAME/KEY: MISC_FEATURE
<222> LOCATION: (29)..(29)
<223> OTHER INFORMATION: X=any amino acid or absent
<220> FEATURE:
<221> NAME/KEY: MISC_FEATURE
<222> LOCATION: (30)..(30)
<223> OTHER INFORMATION: X=any amino acid or absent
<220> FEATURE:
<221> NAME/KEY: MISC_FEATURE
<222> LOCATION: (31)..(31)
<223> OTHER INFORMATION: X=any amino acid or absent

<400> SEQUENCE: 37
```

Xaa Xaa Xaa Xaa Xaa Xaa Xaa Xaa Xaa Arg Phe Asn Lys Pro Phe
1               5                   10                  15

Val Phe Leu Xaa Arg Xaa Xaa Xaa Xaa Xaa Xaa Xaa Xaa Xaa
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: peptide derivative

<400> SEQUENCE: 38

Val Lys Phe Asn Lys Pro Phe Val Phe Leu Met
1               5                   10

<210> SEQ ID NO 39
<211> LENGTH: 11
<212> TYPE: PRT
<213> ORGANISM: Artificial Sequence
<220> FEATURE:
<223> OTHER INFORMATION: peptide derivative

<400> SEQUENCE: 39

Leu Arg Phe Asn Arg Pro Phe Leu Val Val Ile
1               5                   10

<210> SEQ ID NO 40
<211> LENGTH: 11
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (11)..(11)
<223> OTHER INFORMATION: Nle

<400> SEQUENCE: 40

Val Lys Phe Asn Lys Pro Phe Val Phe Leu Xaa
1               5                   10

<210> SEQ ID NO 41
<211> LENGTH: 11
<212> TYPE: PRT
<213> ORGANISM: Artificial Sequence
<220> FEATURE:
<223> OTHER INFORMATION: peptide derivative

<400> SEQUENCE: 41

Arg Phe Asn Arg Pro Phe Leu Val Val Ile Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: peptide derivative

<400> SEQUENCE: 42

Arg Phe Asn Arg Pro Phe Leu Met Ile Ile Arg
1               5                   10

<210> SEQ ID NO 43
<211> LENGTH: 11
<212> TYPE: PRT

-continued

```
<213> ORGANISM: Artificial Sequence
<220> FEATURE:
<223> OTHER INFORMATION: peptide derivative
<220> FEATURE:
<221> NAME/KEY: MOD_RES
<222> LOCATION: (10)..(10)
<223> OTHER INFORMATION: Nle

<400> SEQUENCE: 43

Arg Phe Asn Lys Pro Phe Val Phe Leu Xaa Arg
1               5                   10

<210> SEQ ID NO 44
<211> LENGTH: 11
<212> TYPE: PRT
<213> ORGANISM: Artificial Sequence
<220> FEATURE:
<223> OTHER INFORMATION: peptide derivative

<400> SEQUENCE: 44

Arg Arg Arg Phe Leu Val Val Ile Arg Arg Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: peptide derivative

<400> SEQUENCE: 45

Arg Arg Arg Phe Leu Met Ile Ile Arg Arg Arg
1               5                   10

<210> SEQ ID NO 46
<211> LENGTH: 11
<212> TYPE: PRT
<213> ORGANISM: Artificial Sequence
<220> FEATURE:
<223> OTHER INFORMATION: peptide derivative
<220> FEATURE:
<221> NAME/KEY: MOD_RES
<222> LOCATION: (8)..(8)
<223> OTHER INFORMATION: Nle

<400> SEQUENCE: 46

Arg Arg Arg Phe Val Phe Leu Xaa Arg Arg Arg
1               5                   10
```

PEPTIDES AND METHODS OF USING THE SAME

PRIORITY CLAIM

This application claims priority to U.S. Provisional Patent Application No. 62/705,591, filed Jul. 6, 2020, the content of which is hereby incorporated by reference in its entirety.

SEQUENCE LISTING

This application contains a Sequence Listing, which was submitted in ASCII format via EFS-Web and is hereby incorporated by reference in its entirety. The ASCII copy, created on Jul. 6, 2021, is named Serpin 8001.WO00 Sequence Listing_ST25 and is 23 KB in size.

BACKGROUND

Serine protease inhibitors (SERPINs) are a large family of proteins that are involved in diverse biological functions such as fibrinolysis, blood coagulation and inflammation. When SERPINs bind to their target serine proteases to inactivate the enzymatic activity, a conformational change occurs exposing a unique short peptide motif (5-11 amino acids).[8,43] The protease-inhibitor complex binds to low-density lipoprotein receptor related protein (LRP1) at the newly exposed short peptide motif, a process which is conserved across the entire spectrum of serine protease inhibitors (SERPINs) such as alpha-1 antitrypsin (AAT) and antithrombin III (ATIII) (May 2013).[22,25,43] Therefore, there is a need to develop novel SERPIN peptides and explore their prophylactic and therapeutic effects in various conditions and diseases.

SUMMARY

In one aspect, this disclosure relates to various SERPIN peptides. In some embodiments, the SERPIN peptide comprises, consists essentially of, or consists of an amino acid sequence of X1-Z1-X2-Z2-X3-Z3-F-V-F-L-X4-Z4 (SEQ ID NO. 20), wherein X1 is V or L; X2 is R or F; X3 is R or K; X4 is M, Nle, or I; Z1 is any amino acid; Z2 is any amino acid; Z3 is any amino acid, and Z4 is a sequence of any five amino acids. In some embodiments, the SERPIN peptide comprises, consists essentially of, or consists of an amino acid sequence of X1-Z1-X2-Z2-X3-Z3-F-X4-F-L-Z4-X5 (SEQ ID NO. 21), wherein X1 is V or L; X2 is F or R; X3 is K or R; X4 is V, L, or M; X5 is a sequence any five amino acids; Z1 is any amino acid; Z2 is a sequence of any two amino acids; Z3 is any amino acid; and Z4 is M Nle, or I. In some embodiments, the SERPIN peptide comprises, consists essentially of, or consists of an amino acid sequence of X1-N-X2-P-F-X3-X4-X5-X6 (SEQ ID NO. 4), wherein X1 is R or F, X2 is K or R, X3 is V or L, X4 is F, V or M, X5 is L, V or I, and X6 is M, I, or Nle. In some embodiments, the SERPIN peptide comprises, consists essentially of, or consists of an amino acid sequence of F-X3-X4-X5-X6 (SEQ ID NO. 15), wherein X3 is V or L, X4 is F, V or M, X5 is L, V or I, and X6 is M, I, or Nle. In some embodiments, the SERPIN peptide comprises, consists essentially of, or consists of an amino acid sequence of Z1-RFNRPFLVVIR-Z2 (SEQ ID NO. 17), Z1-RFNRPFL-MIIR-Z2 (SEQ ID NO. 18), or Z1-RFNKPFVFL(Nle)R-Z2 (SEQ ID NO. 37), wherein Z1 and Z2 are independently 1, 2, 3, 4, 5, 6, 7, 8, 9, 10, or between 1 and 3, between 1 and 5, between 1 and 6, between 1 and 7, between 1 and 8, between 1 and 9, or between 1 and 10 basic amino acids. In some embodiments, the SERPIN peptide comprises, consists essentially of, or consists of an amino acid sequence of VKFNKPFVFL(Nle)IEQNTK (SEQ ID NO. 35), VKFNKPFVFLM (SEQ ID NO. 38), LRFNRPFLVVI (SEQ ID NO. 39), VRFNRPFLMII (SEQ ID NO. 31), VKFNKPFVFL(Nle) (SEQ ID NO. 40), RFNRPFLVVIR (SEQ ID NO. 41), RFNRPFLMIIR (SEQ ID NO. 42), RFNKPFVFL(Nle)R (SEQ ID NO. 43), RRRFLVVIRRR (SEQ ID NO. 44), RRRFLMIIRRR (SEQ ID NO. 45), RRRFVFL(Nle)RRR (SEQ ID NO. 46), FVFLM (SEQ ID NO. 3), or FVFL(Nle) (SEQ ID NO. 10). In some embodiments, the SERPIN peptides disclosed herein has a size of between 5 and 30 amino acids, or less than 20 amino acids. In some embodiments, one or more amino acid residues of the SERPIN peptides disclosed herein are D-amino acids. In some embodiments, the SERPIN peptides disclosed herein is fused to an epitope tag, a half-life extender, or both.

In another aspect, disclosed herein is a pharmaceutical composition comprising an effective amount of a SERPIN peptide disclosed herein or a fusion thereof. In some embodiments, the pharmaceutical composition further comprises one or more additional therapeutic agents. In some embodiments, the pharmaceutical composition further comprises a pharmaceutically acceptable carrier, excipient, additive, preservative, or a combination thereof. In some embodiments, the pharmaceutical composition is formulated for oral administration, parenteral administration including subcutaneous administration, intramuscular administration, intravenous administration, and intrathecal administration, intradermal administration, transdermal administration, topical administration, intranasal administration, or inhalation.

In another aspect, disclosed herein is a method of treating a subject suffers from a disease or condition associated with TSLP. The method entails administering to the subject an effective amount of a SERPIN peptide, a fusion thereof, or a pharmaceutical composition disclosed herein. In some embodiments, the subject suffers from asthma, atopic dermatitis, allergic rhinoconjunctivitis, EoE, cancer, or rheumatoid arthritis. In some embodiment, the subject is a human. In some embodiments, the administration is by oral administration, parenteral administration including subcutaneous administration, intramuscular administration, intravenous administration, and intrathecal administration, intradermal administration, transdermal administration, topical administration, intranasal administration, or inhalation. In some embodiments, the SERPIN peptide is administered at a dose from about 0.001 mg/kg to about 4 mg/kg in human.

In another aspect, disclosed herein is a method of treating a subject suffers from a disease or condition associated with LRP1. The method entails administering to the subject an effective amount of a SERPIN peptide, a fusion thereof, or a pharmaceutical composition disclosed herein. In some embodiments, the subject suffers from peripheral neuropathy, neuropathic pain, neurodegenerative disease, sepsis, acute lung injury, acute respiratory distress, TH2 mediated allergic inflammation, or an infectious disease selected from the group consisting of COVID-19 infection, influenza, measles, alphavirus infection, rift-valley fever virus infection, dengue virus infection and Epstein Barr virus infection. In some embodiments, the subject suffers from Alzheimer's Disease or eosinophilic esophagitis. In some embodiments, the subject suffers from EoE, AMI, nerve injury, pain, gout, rheumatoid arthritis, or diabetes including type I and type II diabetes. In some embodiment, the subject is a human. In some embodiments, the administration is by oral administration, parenteral administration including subcutaneous administration, intramuscular administration, intravenous administration, and intrathecal administration, intradermal administration, transdermal administration, topical administration, intranasal administration, or inhalation. In some embodiments, the SERPIN peptide is administered at a dose from about 0.001 mg/kg to about 4 mg/kg in human.

BRIEF DESCRIPTION OF THE DRAWINGS

This application contains at least one drawing executed in color. Copies of this application with color drawing(s) will be provided by the Office upon request and payment of the necessary fees.

FIGS. 6A-6B are brightfield images taken at 48 and 96 hours showing that treatment with SP163M on adult dorsal root ganglia (DRG) neurons resulted in greater neurite outgrowth in these cells compared to both control cells and Nerve Growth Factor (NGF), a potent neurotrophic factor. FIG. 6C shows assessment of cell viability demonstrating that SP163M increased survivability of the neurons compared to vehicle control and even greater than neurotrophic factor-3 (NT-3).

FIGS. 9A-9C show that SP163M demonstrated reduced pain and delays in the onset of inflammation in a formalin pain model. Mice treated with SP163M two hours prior to injecting the mice hind paw with formalin showed a significant reduction in licking in phase 1 and a significantly delayed response to phase 2, suggesting anti-nociceptive properties and anti-inflammatory properties of systemic SP163M.

FIGS. 16A-16C show that SP163M was tested in an acute septic model of *Klebsiella pneumonia* (KP) infection to determine whether SP163M is a viable treatment option for patients with severe lung infection. Bioavailability of SP163M in the plasma, liver, kidney, and lung, was observed, indicating 1-23 hours post-*Klebsiella Pneumonia* (KP) exposure as an appropriate time frame for SP163M treatment (FIG. 16A). Assessment of survival and weight loss in mice administered a 100% lethal dose of KP followed by SP163M or vehicle control administered 1-14 hours later shows that daily SP163M treatment resulted in a significant benefit in survival versus vehicle control. Mice were administered KP (100% lethal dose) by intranasal exposure, followed by SP163M (12 mg/kg) or vehicle control administered 1-14 hours later via i.p. injection (therapeutic model). Daily SP163M treatment (13 doses total) resulted in a significant benefit in survival of 40% (p<0.02) vs. vehicle control. A decrease in weight loss was also observed with SP163M treatment (FIG. 16C).

FIG. 19A illustrates a model of SARS-CoV2 entry and the role of protease inhibitors. FIG. 19B shows the linear regression of TMPRSS2 activity and IC50s of SP163M.

FIGS. 20A-20C show that experiments were performed to analyze the impact of SP163M on alphavirus replication. SP163M treatment reduced replication in two related alphaviruses, Venezuelan Equine Encephalitis Virus (VEEV) and Eastern Equine Encephalitis (EEEV) in a variety of cell types, including Vero cells and primary human astrocytes.

FIG. 24A shows % activation of NFκB. The THP-1 NFκB reporter cells were treated with increasing concentrations of SP163M or scrambled control (SCR) and activated with LPS (0111:B4). FIG. 24B shows IL-1β release (pg/ml) from mouse macrophages (J774A.1) following inflammasome activation using GP96 (priming) and ATP. The cells were treated with SP163M or SCR control. (*$p<0.05$).

FIG. 25A: LPS (1 Ong/ml) was added to RAW264.7 macrophages after incubation for 1 hour with the indicated concentrations of peptide or vehicle. After 24 hours of incubation, the supernatant was assayed by ELISA for levels of TNFα or IL-6. FIG. 25B: IMG Microglial cells. SP16 (100 µg/ml), 24 hours LPS (100 ng/ml) in triplicates. Cytokines supernatant levels (pg/ml). * p-value<0.05, **, p-value<0.01.

FIGS. 26A-26B show the effects of SP163M on adult rat DRG primary cultures. FIG. 26A: representative images showing Beta Tubulin (green) and ATF3 (red) immunostaining in control and SP163M treated DRG neuron cultures. FIG. 26B: trypan blue survivability assay showing SP163M is neuroprotective. *$p<0.05$.

FIG. 27A: The mice were treated with SP16 or vehicle and challenged with a lethal dose of LPS (15 mg/kg) and assessed for survival over 72 hours. SP16 significantly improved survival by 60% ($p<0.001$) compared to vehicle treated animals.

FIG. 27B: SP16 reduced inflammatory cytokines in mouse LPS challenged model. Balb/c mice were treated with vehicle, SP16 or dexamethasone prior to LPS (5 mg/kg). The cytokines were measured in the plasma at 2 hours via ELISA and compared with those from vehicle treated group. (**$p<0.001$).

FIG. 29A: PolyI:C-induced TSLP production by SPINK7 knockout EPC2 cells (Human esophageal epithelial cells). SPINK7 KO cells and control cells were plated in high calcium and high density for 48 hours before being treated with SP163M (100 µg/ml) or A1AT (2 mg/ml) and Poly I:C (5 µg/ml, or untreated) for 8 hours. TSLP production in the supernatant was measured by ELISA. FIG. 29B: Primary esophageal epithelial cells (EPC2) were treated with SP163M and then stimulated with IL-13, a TH2 response mediated cytokine, to induce CCL26. SP163M significantly reduced CCL26 release dose dependently.

DETAILED DESCRIPTION

Figure 1:
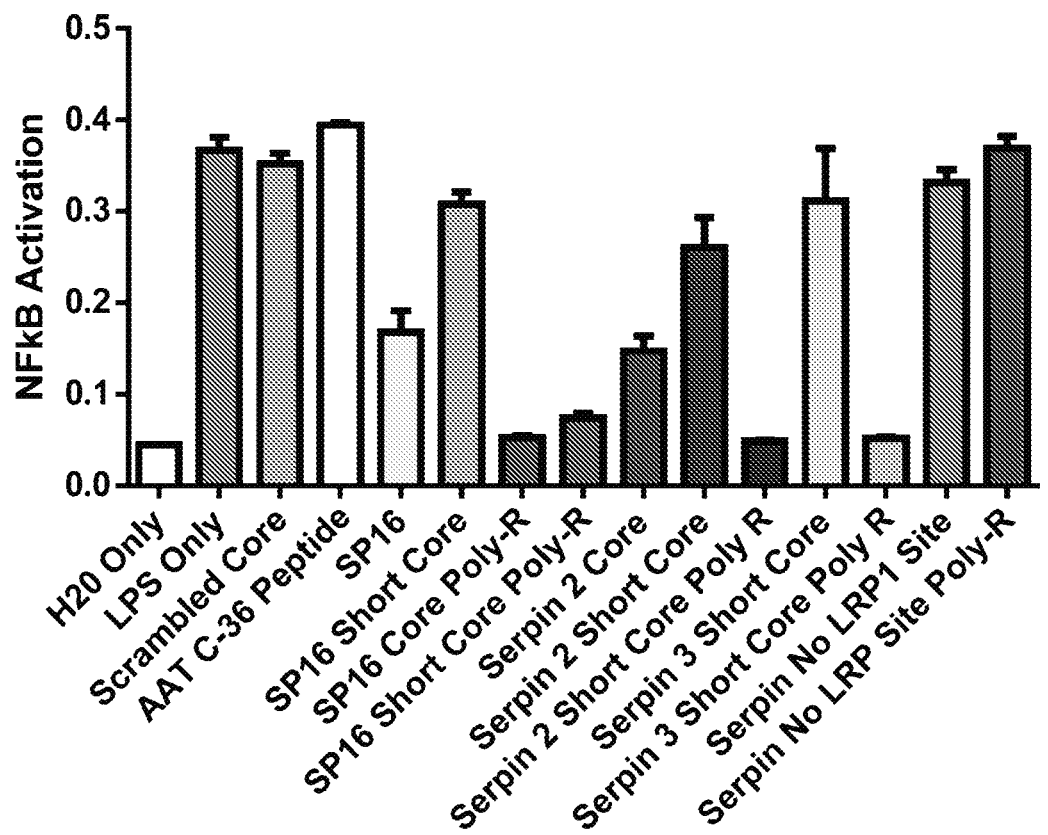
FIG. 1 demonstrates that SERPINs contain an anti-inflammatory core motif comprising the LRP1 binding sequence. In an NFκB reporter assay stimulated with LPS, the NFκB lowering activity of core SERPIN peptides was lost when truncated too short due to instability of the truncated peptides. The activity was restored upon poly arginine residues stabilizing the peptides. However, when the LRP1 binding site was truncated, the activity could not be rescued by poly arginine flanks.

Disclosed herein are C-terminal peptides derived from the SERPIN molecule and variants and derivatives thereof as well as their uses in prevention or treatment of various conditions by targeting LRP1. In certain embodiments, the SERPIN peptides are isolated peptides. In certain embodiments, the SERPIN peptides are synthetic peptides.

Precise coordination of the immune response is needed to promote inflammatory resolution and mitigate tissue damage, and targeting single cytokines or signaling pathways does not resolve all contributing factors in pathology of certain diseases such as those discussed here. A balanced inflammatory response plays a critical role in regeneration and repair and anti-inflammatory drugs have been associated with an opposing action on regeneration and tissue repair.[3]

Surprisingly, the peptides disclosed herein (1) exert neurotrophic effects, (2) have regenerative and healing properties, (3) show analgesic effects, (4) have anti-viral and anti-microbial properties, and/or (5) exert anti-allergic effects. This combination of activities provides a distinct mechanism in treating conditions associated with peripheral neuropathies such as diabetic peripheral neuropath, degenerative disorders, lung injury, allergic diseases and infectious disease. As disclosed in the examples herein, this surprising efficacy is contrasted with the merely anti-inflammatory activity of, e.g., an IL-1 antagonist. The peptides disclosed herein unexpectedly target a homeostatic and cell signaling receptor LRP1. The agonistic action of these peptides to LRP1 provides a unique mechanism beyond the anti-inflammatory effects previously described.

Accordingly, disclosed herein are SERPIN-derived peptides, pharmaceutical compositions comprising the SERPIN-derived peptides, and methods of using the same to treat a number of conditions where a dysregulated immune response or impaired endocytic function, or diseases in which LRP1 mediation could contribute to pathology, such as in conditions associated with peripheral nerve injury and resulting pain, lung injury, infectious disease and allergic inflammation. The unexpected regenerative and healing properties of these peptides allow use of the compositions comprising such peptides to new indications, and allow preventive intervention in conditions associated with, e.g., tissue injury.

Conditions Associated with LRP1

LRP1 functions as an endocytic and cell signal transduction receptor and has several ligands that induce specific cell signaling cascades that can contribute to cell survival and anti-inflammatory mechanisms.[5,18,22,25] LRP1 is ubiquitously expressed on many different organs, abundantly in brain, lung, heart and immune cells. Because of these unique capabilities and wide expression on both tissues and immune cells, it plays a critical role in regulating inflammation, cellular metabolism, and maintaining homeostasis. For instance, LRP1 regulates inflammatory signaling pathways such as NFκB and JNK pathways that induce the conversion of pro-inflammatory (M1) macrophages to the anti-inflammatory (M2) macrophage phenotype, regulates the cytokine output, and contributes to effective migration and phagocytosis.[22,26,51] In neutrophils, LRP1-dependent mechanisms lead to enhanced cell adhesion, chemotaxis, and antibacterial effects of these cells, thereby resisting immunosuppression[25]. During acute infection or injury, LRP1 also promotes inflammatory resolution through scavenging PAMPS and DAMPS from dying or injured tissue, to prevent the tissue injury cycle[25]. LRP1 was also shown to mediate autophagy during infection, an important metabolic process recently shown to play an important protective role in a variety of diseases.[4,19] Therefore, because of its multifunctional ability to regulate inflammation, targeting LRP1 has substantial potential to mitigate several aspects of the immune response that contributes to the pathology of several diseases including neurological disorders, infectious diseases, and allergic inflammatory disease.

Neurological Disease

In terms of nerve injury and associated pain, injury to the peripheral nervous system induces an increase in the expression of LRP1. Previously, it was demonstrated that LRP1 agonist are capable of promoting axonal growth in the CNS and are capable of inducing regeneration after spinal cord injury.[53] LRP1 is an endocytic receptor to a diverse number of ligands including tissue-type plasminogen activator (tPA), matrix metalloproteinase-9 (MMP-9), and activated α2-macroglobulin.[14] These ligands are capable of inducing anti-inflammatory activity,[39] activating the Schwann cell repair program[21] and transactivation of cell signaling pathways in neurons associated with axonal regeneration.[38] LRP1 requires ligand-binding to activate cell-signaling, however, different ligands elicit distinct and sometimes opposing cell-signaling responses reflecting the ability of different ligands to assemble unique co-receptor complexes. Furthermore, many LRP1 ligands are multi-domain proteins with numerous effects on cell physiology that do not involve LRP1-binding. For example, tissue-type plasminogen activator (tPA) binds to LRP1 to promotes Schwann Cell (SC) survival and migration.[23] Yet, by LRP1-independent activities, tPA elicits pain.[1] EI-tPA promotes survival of human iPSC-derived neural progenitor cells (iNPCs) and transplanted EI-tPA activated iNPCs into rodents with severe spinal cord injury demonstrate improved motor functional recovery.[40] Imbalances in the microenvironment following nerve injury may have severe consequences, including the development of chronic neuropathic pain states.[12] In peripheral nervous system (PNS) injury, both inflammatory cytokines such as TNFα, IL-6 and IL-1β and anti-inflammatory cytokines such as IL-10 have been shown to play a central role in axon regeneration and repair.[6]

As demonstrated herein, the disclosed peptides robustly promote neuronal survival, axonal growth, and expression of regeneration associated genes, such as ATF3, in adult rat primary dorsal root ganglia (DRG) cultures. The disclosed peptides also act as a potent anti-inflammatory agent, inhibiting NFκB signaling in response to lipopolysaccharide (LPS). As an LRP1 agonist, the disclosed peptides target both SC and neurons, the dysfunction of which contributes to abnormal regeneration, poor functional recovery, and chronic neuropathic pain. Thus, the peptides disclosed herein can be used for treating PNIs associated with the development of chronic pain.

In terms of neurodegenerative disease such as Alzheimer's Disease (AD), LRP1's role has been extensively studied. AD is characterized by a progressive loss of cognitive abilities and formation of senile plaques, which are composed largely of amyloid β (Aβ), and tau protein aggregates called neurofibrillary tangles (NFTs) in the hippocampus and cortex of afflicted humans. The spread of protein aggregates during disease progression is a common theme underlying neurodegenerative disease pathology. As an endocytic receptor, LRP1 was shown to regulate brain and systemic clearance, degradation and production of amyloid β-peptide.[54] As LRP1-mediated clearance of Aβ across the blood brain barrier (BBB) is the key event in the regulation of Aβ transcytosis from brain to periphery, targeting LRP1 with one or more peptides disclosed herein may serve as a novel treatment. Also, tau protein aggregates forming NTFs plays a central role in the pathogenesis of Alzheimer's disease. LRP1 functions to regulate tau protein endocytosis, accumulation and spread associated with worsened pathology.[32] Therefore, the peptides disclosed herein may serve as an intervention that remediates both plaque and tangle pathologies through mediation of LRP1 associated protein aggregation of tau and amyloid a β. The peptides disclosed herein also act on neuroinflammation, which plays a critical role in neurodegenerative disease. Microglial cells act as the resident immune cell of the brain, serving to maintain homeostasis in the environment. Reactive glia cells and associated neuroinflammation play a key role in both disease initiation and progression becoming activated through dysregulated clearance of beta amyloid and other damage associated molecular patterns (DAMPs).[13] AB deposition and tau hyper-phosphorylation contribute to microglial activation, NFκB inflammatory pathway activation and associated pro-inflammatory cytokines such as TNFα, IL-6 and IL-1β, which contribute to neuronal damage and loss. Impaired autophagy, a homeostatic process that degrades and recycles proteins such as beta amyloid, has been associated with AD.[7] LRP1 has been shown to mediate healthy lysosomal processing associated with autophagy. Therefore, through LRP1, the disclosed peptides can mediate several aspects of AD including healthy cell metabolism to reduce the spread of protein aggregation, alleviate neuroinflammation and improve neuronal dysfunction leading to survival and possibly regeneration of these cells.

Acute Lung Injury (Acute Respiratory Distress Syndrome)

Acute Lung Injury (ALI), leading to Acute Respiratory Distress Syndrome (ARDS), can be initiated by a variety of inflammatory insults such as pneumonia, traumatic injury, and/or infection. A key initiation step in ALI is the dysregulated innate immune response to damage associated or pathogen associated molecular patterns (DAMPs or PAMPs, respectively). Alveolar macrophages are activated by the infectious microbes in Toll-like and Nod-like Receptor signaling pathways that lead to further macrophage and circulating neutrophil recruitment. Neutrophils accumulate in the lungs and release proinflammatory cytokines and other cytotoxic substances causing exacerbation of the injury. The lung epithelium is damaged by these cells and their secreted products cause pulmonary edema and potential respiratory distress (ARDS). An increase in proinflammatory cytokines TNF-alpha, IL-1 beta, IL-6, IL-8, and IL-18 occurs resulting in a "cytokine storm" which is predictive of morbidity and mortality in sepsis. LRP1 was reported to be a critical player in sepsis and ARDS as it regulates lung inflammation and lung tissue repair.[49] The peptides disclosed herein target LRP1, leading to the precise coordination of the immune response in order to restore homeostasis. Therefore, the disclosed peptides can have a significant impact to mitigate lung damage and improve survival through multiple mechanisms initiated by inducing specific LRP1-mediated signaling pathways. These mechanisms include rebalancing the cytokine output to promote inflammatory resolution, mediating autophagy to restore proper cell metabolic processes, restoring immune cell function and receptor scavenging to regulate the tissue injury cycle. These mechanisms help in infection clearance and allow the host to better fight infection. Based on these mechanisms, the disclosed peptides can be used as immunomodulatory therapeutic agents to prevent or treat ARDS by mediating LRP1 signaling.

Infectious Disease

Acute respiratory distress syndrome (ARDS) is a major complication in patients with severe COVID-19 illness. Clinical evaluation and retrospective studies out of Wuhan China show that all of the patients admitted to hospital presented with pneumonia, of those 29% developed ARDS and among critically ill patients who were non-survivors, a vast majority (81%) had developed ARDS.[17,52] Therefore, patients who develop ARDS are at a substantially higher risk of death. Virally mediated activation of the innate immune response through the Toll-like Receptors (TLRs) initiates an inflammatory response that is necessary to eliminate the infection. In some cases, the initiating viral insults and triggers are highly amplified and uncontrolled, resulting in overstimulation of the immune cells and an aberrant cytokine release (known as a cytokine storm), resulting in tissue damage that can lead to organ failure and death. Cytokine regulation is a key factor in preventing the harmful effects of an overactive immune response and controlling the cytokine storm could have a significant impact on viral pneumonia progression to ARDS. In the case of SARS-CoV-2, emerging evidence suggests that for a subpopulation of patients with severe illness, the cytokine storm is a contributing factor to mortality.[27] Recently, clinical trials were launched for Kevzara (sarilumab), an interleukin-6 inhibitor (IL-6), for the treatment of coronavirus infected patients with lung complications. IL-6 is a biomarker associated with higher mortality rates in individuals with pneumonia. Those trials will provide critical insight into the effectiveness of single cytokine targeted therapeutics. However, historically, targeting a single cytokine or pathway in ARDS patients has not proved to be an effective approach.

LRP1 signaling mediated by the peptides disclosed herein may have therapeutic potential as an immunomodulatory strategy to improve COVID-19 patient outcomes through regulating several mechanisms of lung inflammation including curbing the cytokine storm, improving cell survival, regulating autophagy and cell metabolism to clear infection and controlling tissue repair signaling pathways to promote proper healing and prevent fibrosis. LRP1 is widely known to regulate protease/antiprotease activity and mediate viral entry.[43] The novel coronavirus utilizes proteases (TM-PRSS2) to regulate cell entry and infection and treatment with its corresponding protease inhibitor such as SERPIN blocked lung cell infection.[16,24,28] SARS-CoV-2 viral entry is dependent on a serine protease TMPRSS2 that primes the viral S protein involved in host cell entry, which is the first step in the viral replication cycle. Camostat mesylate is a natural SERPIN with protease inhibitor function of TMPRSS2 and was effective in reducing SARS-CoV-2 viral entry, which can limit both infection and spread of the disease.[16] An alpha-1 antitrypsin derivative disclosed herein such as SP163M is also capable of inhibiting TMPRSS2, potentially through LRP1 and may have effects in reducing SARS-CoV-2 viral replication. As demonstrated herein, the disclosed peptides can reduce SARS-CoV-2 replication in vitro, the mechanism of which may be LRP1 control of the host protease/viral protein interaction to inhibit viral entry. The disclosed peptides are also screened for viral activity against several other DNA and RNA viruses and found to inhibit replication of many, indicating a broad-spectrum mechanism through modifying host responses.

Arthropod-borne viruses are important causes of acute encephalitis and an emerging worldwide problem with an ever-growing risk for importation into new regions.[11,31] The mosquito-borne encephalitic alphaviruses including Venezuelan (VEEV), eastern (EEEV) and western equine encephalitis viruses (WEEV) are endemic in the Americas and cause outbreaks of encephalomyelitis, which can spread into the United States. In humans VEEV causes a febrile illness typified by fever, malaise, and vomiting. In some cases, infection progresses to the central nervous system (CNS). Neurological cases have a mortality rate as high as 35% in children and 10% in adults, with long-term neurological deficits often seen in survivors.[42] The overall estimate of VEEV survivors with neurological sequelae is 4-14% but may be even greater due to the misdiagnosis of arboviral encephalitis.[33]

VEEV infection is known to inhibit cellular transcription and translation in order to downregulate the innate immune response.[45,48] In contrast, in the central nervous system (CNS), VEEV infection results in the upregulation of numerous genes in the inflammatory response and apoptotic pathway.[45,48] Specifically, pro-inflammatory cytokines including interleukin-1β (IL-1β), IL-6, IL-12, and tumor necrosis factor-α (TNF-α) play a role in VEEV pathogenesis.[9,20,30,34,35] Gene expression changes were analyzed in the brain tissue of VEEV infected mice and alterations in immune pathways involved in antigen presentation, inflammation, apoptosis and the traditional antiviral response were discovered.[36] In addition, viral modulation of extracellular matrix and adhesion genes such as integrins, cadherin-1, cadherin-2, vascular cell adhesion molecule-1, and intracellular adhesion molecule-1 (ICAM-1) in the brains of VEEV infected mice was observed.[37] ICAM-1 knockout mice demonstrated reduced inflammation in the brain and a subsequent delay in the onset of clinical disease.[37] These studies suggest that alphavirus-induced inflammation contributes substantially to neurological damage and that control of inflammation is a viable therapeutic strategy.

The peptides disclosed herein can bind LRP1 and initiate the immune modulatory cascade. LRP1 expression increases during ischemia, tissue injury and viral infection.[2,22,25,43] The binding of one or more disclosed peptides to LRP1 can inhibit the inflammatory response and induce pro-survival signaling through phosphorylation of protein kinase Akt. Therefore, targeting LRP1 has potential as a broad-spectrum therapeutic strategy for infectious disease.

Through LRP1 directed host mediated mechanisms, the SERPIN peptides can curb the harmful cytokine storm associated with severe COVID-19 disease, activate protective pathways to prevent lung damage, and/or clear infection faster and has direct impact on suppressing viral infection. Therefore, the dual anti-inflammatory and antiviral mechanism of the SERPIN peptides can have effects in improving survival in patients with SARS-COV2 induced ARDS.

Eosinophilic Esophagitis

The peptides disclosed herein can serve as an adjunct treatment to mitigate the acute inflammatory response in patients with ST segment elevation myocardial infarction (STEMI). Additionally, SP163M has been shown to be safe and well tolerated in both Phase I and the ongoing Phase IIa clinical trials. The peptide therapy is unique in that it rebalances dysregulated immune responses and protects tissues from injury without any major immunosuppressive effects. Therefore, it is a safe anti-inflammatory drug that has broad-spectrum utility across a wide variety of immune-mediated diseases.

Eosinophilic Esophagitis (EoE) is a chronic, largely type-2 immune mediated allergic inflammatory response associated with esophageal dysfunction and disturbed epithelial barrier function. This food-allergen driven disease is characterized by eosinophil dominated inflammation and type-2 mediated immune responses that lead to esophageal damage. In the US, an estimated 150,000 patients (largely children) are currently suffering from this disorder that commonly causes esophageal pain, difficulty swallowing, food impaction, persistent heartburn, chest and abdominal pain, weight loss, nausea, vomiting and failure to thrive. Currently, there are no FDA approved therapeutics for the treatment of EoE, and management of the disease consists of diet restrictions, proton pump inhibitors, and corticosteroids. The current standard-of-care therapies do not adequately address the immune dysregulation that occurs in EoE and other allergic inflammatory diseases such as asthma or atopic dermatitis.

EoE is characterized by a high number of eosinophils, proteases, cathelicidin, serine proteases including the kallikreins (KLKS), as well thymic stromal lymphopoietin (TSLP)—a cytokine and master regulator of allergic type-2 inflammatory responses in the local environment.[41] In esophageal epithelial cells, a loss of the function of a serine peptidase inhibitor, Kazal type 7-SPINK7, results in uncontrolled protease activity, release of pro-inflammatory cytokines such as TNFα, CCL2, GM-CSF, IL-8, and CXCL10 and inflammation. Recently, it was found that the serine protease KLK-5, which is an important mediator of epithelial barrier function, is a direct target of SPINK7 and loss of SPINK7 mediates EoE pathogenesis largely through uncontrolled KLK-5 protease activity. Interestingly, the SERPIN Alpha-1 antitrypsin, is capable of inhibiting KLKS activity in vitro and allergen-induced esophageal eosinophilia in vivo. However, the mechanism of the activity is not yet clear and may involve LRP1, instead of or in addition to direct proteolytic inhibition.

Patients with eosinophilic asthma have lower levels of LRP1. In addition, LRP1 deletion specifically of CD11b and CD11c dendritic cells in mice results in heightened allergic inflammatory response in an allergic airway disease model.[29] Mice with LRP1 deletion had increased antigen uptake and suffered increased eosinophilic inflammation, allergic sensitization, Th2 mediated cytokine production and a reduction in T-regulatory cells.[29] Therefore, LRP1 could aid in maintaining homeostasis of proteases/inhibitors in the esophageal environment, mediating the TH2 responses and inhibiting inflammatory signaling pathways (NFκB, JNK) resulting in repair of esophageal dysfunction.

The anti-inflammatory and homeostatic effects of SP16 are mediated through targeting LRP1. Treatment by the peptides disclosed herein such as SP16 and SP163M effectively shuts down major inflammatory signaling pathways such as NFκB. During allergic inflammation, there is a crucial interplay of the innate and adaptive immune responses, and NFκB signaling can be described as a master transcriptional regulator of both responses. The peptides disclosed herein such as SP16 and SP163M effectively dampen pro-inflammatory cytokines IL-113, IL-6 and TNFα, while increasing anti-inflammatory cytokine levels, such as IL-10 and TGFβ. Signaling pathway analysis of SP16 also show inhibition of JAK/STAT signaling cascade, an important mediator of TH2 responses. Skewing of the hyper Th2 immune milieu through LRP1 dependent signaling and subsequent inhibition of Th2 cell mediated cytokines (IL-5, IL-4, IL-13) works to resolve allergic inflammation. Furthermore, SP16 has been shown to inhibit thymic stromal lymphopoietin (TSLP) in epithelial cells, and other important mediators (CCL11, CCL26) of eosinophilic inflammation. Another mechanism that SP16 controls inflammation is through LRP1 dependent endocytosis to clear dead cells/debris, proteases and other allergic triggers that lead to epithelial barrier damage. SP16 also works through LRP1 dependent PI3K/Akt pro-survival pathways to promote a favorable environment for epithelial barrier healing and repair. Therefore, a major benefit of SP16 and derivatives thereof is that although the peptides have strong anti-inflammatory properties, they are not a general immunosuppressive drug. Instead, the peptide works through LRP1 dependent pathways to alter the immune response and restore homeostasis. FIG. 1 summarizes the mechanisms by which SP16 exerts anti-inflammatory and healing functions.

The disclosed peptides such as SP 16 and SP163M demonstrated anti-inflammatory and pro-survival effects in a wide variety of inflammatory and auto-immune disease models. The peptides function as a potent LRP1 agonist with no protease inhibitor function and can reduce the cytokine TSLP release in SPINK7 knock out cells. In addition, the disclosed peptides can reduce TH2 mediated cytokines in human esophageal epithelial cells. The disclosed peptides can have significant implications in alleviating eosinophilic esophagitis by mediating control over LRP1.

SERPIN Peptides and Pharmaceutical Compositions Comprising the Same

Disclosed herein are SERPIN peptides including isolated, synthetic peptides and derivatives thereof that specifically bind to LRP1. LRP1 is an endocytic scavenger receptor for numerous ligands which exert biologically distinct functions. The LRP1 protein consists of a smaller (85 kD, 13 chain) intracellular fragment which spans the cell membrane, non-covalently attached to an extracellular fragment (515 kD, α Chain) which consists of ligand-binding-type repeats, responsible for the majority of ligand binding. In addition to its ability to mediate the endocytosis for various lipoproteins, protease/inhibitor complexes, viruses, matrix proteins and growth factors via its extracellular domain, LRP1 interacts with various scaffolding and signaling proteins via its intracellular domain to mediate cell signaling. Due to the multifunctional capability (both endocytic and cell signaling control) of LRP1, it is implicated in a variety of biological functions, including cell growth/survival, homeostasis, cell metabolism, cytokine regulation, and trafficking foreign antigens. Therefore, LRP1 is implicated to play a role in a variety of diseases.

In certain embodiments, the SERPIN peptide disclosed herein comprises, consists essentially of, or consists of a core sequence FNKPFVFLM (SEQ ID NO. 1) of the SP16 peptide which has a sequence of VKFNKPFVFLMIEQNTK (SEQ ID NO. 2). In certain embodiments, the SERPIN peptide disclosed herein is an analog or derivative of SP16 peptide, sharing at least 50%, at least 55%, at least 60%, at least 65%, at least 70%, at least 75%, at least 80%, at least 85%, at least 90%, or at least 95% identity to SP16. The core sequence includes the LRP1 binding site having a sequence of FVFLM. Surprisingly, when Met of the core sequence is replaced by Nle, the activities of the SERPIN peptides increased significantly. Accordingly, in certain embodiments, the SERPIN peptide disclosed herein comprises, consists essentially of, or consists of a core binding motif having a sequence of X1-N-X2-P-F-X3-X4-X5-X6, wherein X1 is R or F, X2 is K or R, X3 is V or L, X4 is F, V or M, X5 is L, V or I, and X6 is M, I, or Nle. In certain embodiments, the binding motif has a sequence of FNKPFVFLM (SEQ ID NO. 1), FNKPFVFL[Nle] (SEQ ID NO. 5), FNRPFLVVI (SEQ ID NO. 6), FNRPFLVV[Nle] (SEQ ID NO. 7), FNRPFLMII (SEQ ID NO. 8), or FNRPFLVI[Nle] (SEQ ID NO. 9). In certain embodiments, the SERPIN peptide disclosed herein comprises, consists essentially of, or consists of a LRP1 binding site having a sequence of F-X3-X4-X5-X6, wherein X3 is V or L, X4 is F, V or M, X5 is L, V or I, and X6 is M, I, or Nle. In certain embodiments, the LRP1 binding site has a sequence of FVFLM (SEQ. ID NO. 3), FVFL[Nle] (SEQ ID NO. 10), FLVVI (SEQ ID NO. 11), FLVV[Nle] (SEQ ID NO. 12), FLMII (SEQ ID NO. 13), or FLMI[Nle] (SEQ ID NO. 14).

In certain embodiments, the SERPIN peptides disclosed herein comprise, consist essentially of, or consist of a modified core binding motif by adding a flanking sequence comprising one or more basic amino acids, an arginine, or both of one or more basic amino acids and an arginine to either or both sides of the core binding motif. For example, the SERPIN peptide disclosed herein comprises, consists essentially of, or consists of an amino acid sequence of Z1-R-X1-N-X2-P-F-X3-X4-X5-X6-R-Z2, wherein X1 is R or F, X2 is K or R, X3 is V or L, X4 is F, V or M, X5 is L, V or I, X6 is M, I, or Nle, and Z1 and Z2 are independently 1, 2, 3, 4, 5, 6, 7, 8, 9, 10, or between 1 and 3, between 1 and 5, between 1 and 6, between 1 and 7, between 1 and 8, between 1 and 9, or between 1 and 10 basic amino acids. In certain embodiments, the SERPIN peptide disclosed herein comprises, consists essentially of, or consists of an amino acid sequence of Z1-RFNRPFLVVIR-Z2 (SEQ ID NO. 17), Z1-RFNRPFLMIIR-Z2 (SEQ ID NO. 18), or Z1-KFNKPFVFL(Nle)R-Z2 (SEQ ID NO. 19), wherein Z1 and Z2 are independently 1, 2, 3, 4, 5, 6, 7, 8, 9, 10, or between 1 and 3, between 1 and 5, between 1 and 6, between 1 and 7, between 1 and 8, between 1 and 9, or between 1 and 10 basic amino acids.

In certain embodiments, the SERPIN peptide disclosed herein comprises, consists essentially of, or consists of an amino acid sequence of X1-Z1-X2-Z2-X3-Z3-F-V-F-L-X4-Z4 (SEQ ID NO. 20), wherein:
X1 is V or L;
X2 is R or F;
X3 is R or K;
X4 is M, Nle, or I;
Z1 is any amino acid;
Z2 is any amino acids;
Z3 is any amino acid, and
Z4 is a sequence any five amino acids.

In some embodiments, this peptide comprises, consists essentially of, or consists of 20 or fewer amino acids.

In certain embodiments, the SERPIN peptide disclosed herein comprises, consists essentially of, or consists of an amino acid sequence of X1-Z1-X2-Z2-X3-Z3-F-X4-F-L-Z4-X5 (SEQ ID NO. 21), wherein:
X1 is V or L;
X2 is F or R;
X3 is K or R;
X4 is V, L, or M;
X5 is a sequence any five amino acids;
Z1 is any amino acid;
Z2 is a sequence of any two amino acids;
Z3 is any amino acid; and
Z4 is M, Nle, or I.

In some embodiments, this peptide comprises, consists essentially of, or consists of 20 or fewer amino acids.

In certain embodiments, the SERPIN peptide disclosed herein comprises, consists essentially of, or consists of the sequence of VKFNKPFVFL(Nle)IEQNTK (SEQ ID NO. 35), VKFNKPFVFLM (SEQ ID NO. 25), LRFNRPFLWI (SEQ ID NO.29), VRFNRPFLMII (SEQ ID NO.31), VKFNKPFVFL(Nle) (SEQ ID NO. 40), RFNRPFLVVIR (SEQ ID NO. 41), RFNRPFLMIIR (SEQ ID NO. 42), RFNKPFVFL(Nle)R (SEQ ID NO. 43), RRRFLWIRRR (SEQ ID NO. 44), RRRFLMIIRRR (SEQ ID NO. 45), or RRRFVFL(Nle)RRR (SEQ ID NO. 46).

In certain embodiments, the SERPIN peptide disclosed herein has a size of between 5 and 30 amino acids, for example, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the SERPIN peptide disclosed herein has a size of 20 amino acids or less. A longer peptide may have a decreased solubility, whereas a shorter peptide may have decreased stability. As disclosed herein, various modifications can be made to improve stability such as adding poly R sequences or other flanking sequences and forming a fusion protein.

The SERPIN peptides include analogues or derivatives thereof. For example, the native sequence of the SERPIN peptides can be modified to enhance plasma stability and result in an increased binding affinity to the peptide's cognate receptor. In certain embodiments, the SERPIN peptides disclosed herein can be further modified to extend the shelf life and/or bioavailability using one or more non-natural peptide bonds or amino acids or by attaching to the peptide functional groups such as polyethylene glycol (PEG). In certain embodiments, the SERPIN peptides disclosed herein are modified by adding one or more amino acid residues such as arginine at either or both ends. In certain embodiments, the SERPIN peptides are modified by adding two, three, or four amino acid residues at both ends.

In certain embodiments, the SERPIN peptides disclosed herein are fused to one or more other peptides to form a fusion peptide or fusion protein. For example, one or more other peptides include an epitope tag such as ALFA-tag, V5-tag, Myc-tag, HA-tag, Spot-tag, T7-tag, NE-tag, a half-life extender such as poly(ethylene glycol) (PEG), Lipidation, FC fusion, or Albumin fusion, or both of an epitope tag and a half-life extender. In certain embodiments, the peptide comprises one or more D-amino acids, that is, one or more amino acids of the peptide have a D-configuration.

In another aspect, this disclosure relates to a pharmaceutical composition comprising, consisting essentially of, or consisting of an effective amount of one or more SERPIN peptides or fusion peptides disclosed herein. In some embodiments, the pharmaceutical composition further comprises one or more additional therapeutic agents, which are not the SERPIN peptides disclosed herein. In some embodiments, the pharmaceutical composition further comprises a pharmaceutically acceptable carrier, excipient, additive, preservative, or a combination thereof. Examples of acceptable carriers include physiologically acceptable solutions, such as sterile saline and sterile buffered saline.

The term "an effective amount" as used herein refers to an amount of a composition that produces a desired effect. An effective amount of a composition may be used to produce a prophylactic or therapeutic effect in a subject, such as preventing or treating a target condition, alleviating symptoms associated with the condition, or producing a desired physiological effect. In such a case, the effective amount of a composition is a "therapeutically effective amount," "therapeutically effective concentration" or "therapeutically effective dose." The precise effective amount or therapeutically effective amount is an amount of the composition that will yield the most effective results in terms of efficacy of treatment in a given subject or population of cells. This amount will vary depending upon a variety of factors, including but not limited to the characteristics of the composition (including activity, pharmacokinetics, pharmacodynamics, and bioavailability), the physiological condition of the subject (including age, sex, disease type and stage, general physical condition, responsiveness to a given dosage, and type of medication) or cells, the nature of the pharmaceutically acceptable carrier or carriers in the formulation, and the route of administration. Further an effective or therapeutically effective amount may vary depending on whether the composition is administered alone or in combination with another composition, drug, therapy or other therapeutic method or modality. One skilled in the clinical and pharmacological arts will be able to determine an effective amount or therapeutically effective amount through routine experimentation, namely by monitoring a cell's or subject's response to administration of a composition and adjusting the dosage accordingly. For additional guidance, see Remington: The Science and Practice of Pharmacy, $21^{st}$ Edition, Univ. of Sciences in Philadelphia (USIP), Lippincott Williams & Wilkins, Philadelphia, Pa., 2005.

In certain embodiments, the peptides or the pharmaceutical compositions disclosed herein may be formulated for oral administration, parenteral administration such as intravenous administration, intramuscular administration, subcutaneous administration (bolus injection or through a device such as an infusion pump), intradermal administration, transdermal administration, topical administration, and intranasal administration. In certain embodiments, a subcutaneous infusion pump can be used for delivery of the peptides or the pharmaceutical compositions disclosed herein. The peptides or the pharmaceutical compositions may be administered more than once. More specifically, after the initial administration, one or more additional doses may be given as a booster.

The SERPIN peptides or the pharmaceutical compositions disclosed herein have various functions. In certain embodiments, disclosed herein is a method of treating a subject in need thereof an effective amount of one or more SERPIN peptides, fusion peptides, or the pharmaceutical compositions disclose herein. In some embodiments, the subject suffers from a disease or condition in which LRP1 mediation contributes to pathology, such as in conditions associated with peripheral nerve injury and resulting pain, lung injury, infectious disease and allergic inflammation such as eosinophilic esophagitis. In some embodiments, the subject suffers from a disease associated with dysregulated immune response selected from the group consisting of peripheral neuropathies, neuropathic pain, COVID-19 infection, acute respiratory distress syndrome (ARDS), sepsis, SARS-CoV-2, Influenza, alphavirus infection, and cytokine storm.

As used herein, "treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. Treatment may also mean a prophylactic or preventative treatment of a condition.

As used herein, the term "subject" is a mammal. In some embodiments, the subject is human. In some embodiments, the subject has not received any prior treatment with serine protease inhibitors, such as alpha-1-antitrypsin treatment before the treatment with the peptides disclosed herein.

In some embodiments, the peptides can be used to reduce the serum TNF-α levels in human individuals who have pathologically increased TNF-α levels. The peptide causes a 75% decrease in serum TNF-α levels when administered in an effective amount to a human subject. In certain embodiments, the peptide results in a 50% or 75% decrease in serum TNF-α levels when administered in an effective amount to a human subject compared to the levels before administration of the peptide.

In some embodiments, the SERPIN peptides and fusions thereof or pharmaceutical compositions comprising the peptides or fusions can be used to treat a disease or condition associated with LRP1 such as EoE, AMI, nerve injury, pain, gout, rheumatoid arthritis, and diabetes including type I and type II diabetes. In some embodiments, the SERPIN peptides and fusions thereof or pharmaceutical compositions comprising the peptides or fusions can be used to treat a disease or condition associated with thymicomal lymphopoietin (TSLP), in particular, TSLP-associated allergic diseases such as allergic asthma, atopic dermatitis, allergic rhinoconjunctivitis, EoE, cancer, and rheumatoid arthritis.

In some embodiments, the SERPIN peptides and fusions thereof or pharmaceutical compositions comprising the peptides or fusions can be administered at a dose from about 0.001 mg/kg to about 4 mg/kg in human. In general, 3 µg in a mouse corresponds to 0.012 mg/kg in humans. Depending on the indication, severity, and administration route, a suitable dose can be selected accordingly. For example, for acute indications, fewer treatments with a higher dose in each treatment are administered; while for chronic indications requiring frequent and long-term treatment, a lower dose in each treatment is administered. In some indications where the inflamed tissue expresses high density of LRP1, a very low dose of the SERPIN peptides such as SP16 and SP163M is required. When a subject suffers from a nerve injury, neurons express very high density of LRP1. In vivo and in vitro studies demonstrated a significant effect with a low dose of 0.05 ug.

In some embodiments, the SERPIN peptides and fusions thereof or pharmaceutical compositions comprising the peptides or fusions is administered subcutaneously. In some embodiments, a SERPIN peptide such as SP16 or SP163M is administered subcutaneously to a human subject at a dose of between 0.05 mg/kg and 0.5 mg/kg, for example, at a dose of 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, or 0.5 mg/kg. In some embodiments, a SERPIN peptide such as SP16 or SP163M is administered subcutaneously to a human subject at a dose of 0.2 mg/kg or 0.4 mg/kg. In some embodiments, a SERPIN peptide such as SP16 or SP163M is administered orally to a human subject at a dose between 1 mg and 150 mg, for example, at a dose of 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, or 150 mg. In some embodiments, a SERPIN peptide such as SP16 or SP163M is administered orally to a human subject at a dose of 5 mg, 25 mg or 100 mg. In some embodiments, a SERPIN peptide such as SP16 or SP163M is administered locally, e.g., by a transdermal patch, optionally with pulsatile delivery, at a dose between 0.05 mg/kg and 0.5 mg/kg, for example, at a dose of 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, or 0.5 mg/kg.

In some embodiments, a single dose of the SERPIN peptides and fusions thereof or pharmaceutical compositions comprising the peptides or fusions is administered. In some embodiments, the SERPIN peptides and fusions thereof or pharmaceutical compositions comprising the peptides or fusions is administered as the sole therapeutic agent. In some embodiments, the SERPIN peptides and fusions thereof or pharmaceutical compositions comprising the peptides or fusions is administered in combination with a secondary therapeutic agent.

In some embodiments, the SERPIN peptides and fusions thereof or pharmaceutical compositions comprising the peptides or fusions is administered in a pulsatile mode or a continuous mode. In some embodiments, the SERPIN peptides and fusions thereof or pharmaceutical compositions comprising the peptides or fusions is administered via a transdermal patch, an inhaler, or an intranasal device.

The following examples are intended to illustrate various embodiments of the invention. As such, the specific embodiments discussed are not to be constructed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Identification of Anti-Inflammatory Motif

As demonstrated herein, a small peptide fragment of the C-terminal end of alpha-1 antitrypsin (the prototypical SERPIN) is capable of binding to LRP1, exerting potent cell regenerative, tissue protective and immune-modulatory functions. Interestingly, the naturally occurring degradative C-terminal product of Alpha-1 Anti-trypsin (termed C-36) exhibits pro-inflammatory activity similar to lipopolysaccharide in both macrophages and neutrophils.[44] By excising a short fragment of the C-terminal end of Alpha-1 antitrypsin, the anti-inflammatory sequences were identified. The amino acid sequences of the peptides tested are shown in Table 1 below. The core sequences containing the LRP1 binding site for each peptide are shown in bold and underlined.

TABLE 1

Peptides Tested for Anti-Inflammatory Activity

| Peptides | SEQ ID NO. | Sequences |
| --- | --- | --- |
| SP34 (Scrambled Core) | 22 | F P K M V P Q F N T E L K I F P E V N I K |
| SP8 (AAT C-36 Peptide) | 23 | S I P P E V K F N K P F V F L M I E Q N T K S P L F M G K V V N P |
| SP16 (AAT Core) | 24 | V K F N K P F V F L M I E Q N T K |
| SP20 (SP16 Short Core) | 25 | V K F N K P F V F L M |
| 5P21 (SP16 Core Poly-R) | 26 | R R R V K F N K P F V F L M I E Q N T K R R R |
| SP22 (SP16 Short Core Poly-R) | 27 | R R R V K F N K P F V F L M R R R |
| SP23 (SERPIN 2 Core) | 28 | L R F N R P F L V V I F S T S T Q |
| SP24 (SERPIN 2 Short Core) | 29 | L R F N R P F L V V I |
| SP26 (SERPIN 2 Short Core Poly-R) | 30 | R R R L R F N R P F L V V I R R R |
| SP28 (SERPIN 3 Short Core) | 31 | V R F N R P F L M I I |

TABLE 1-continued

Peptides Tested for Anti-Inflammatory Activity

| Peptides | SEQ ID NO. | Sequences |
|---|---|---|
| SP29 (SERPIN 3 Short Core Poly-R) | 32 | R R R V R F N R P F L M I I R R R |
| SP31 (SERPIN No LRP1 Site, which has the LRP1 binding site truncated) | 33 | V R F N R P F L |
| SP32 (SERPIN No LRP1 Site Poly-R) | 34 | R R R V R F N R P F L R R R |

The reporter cells (THP1-XBlue-MD2-CD14 cells) were treated with each peptide (50 µg/ml) before being insulted with LPS (5 ng/ml) and incubated overnight. The NFκB inducible (Secreted Embryonic Alkaline Phosphatase) SEAP was measured in the supernatant and read for absorbance. As shown in FIG. 1, various SERPIN peptides share a common core motif demonstrated anti-inflammatory activity in NFκB reporter cells when insulted with LPS. LPS insult lead to an increase in NFκB activity, and neither the scrambled core control peptide nor the AAT C-36 fragment decreased the NFκB activity. In fact, the AAT C-36 fragment showed NFκB inducible properties without the need for LPS.

In contrast, SP16 is capable of reducing NFκB activity, however, the short core peptide SP20 did not have an inhibitory effect. Although this truncated AAT derived peptide contains the core sequence and LRP1 binding site, it is unstable and therefore, exhibited no activity. When SP16 was flanked with triple arginine amino acids on both sides (termed "Poly-R") to obtain SP21, the SP21 peptide's stability increased and NFkB inhibition increased as well relative to SP16. When the SP16 short core, SP20 peptide, was stabilized using triple arginine flanks to obtain SP22, the NFκB activity was significantly reduced. Similar effects were observed for the other two pairs of SERPIN peptides, SERPIN 2 short core (SP24) vs. SERPIN 2 short core poly-R (SP26), and SERPIN 3 short core (SP28) vs. SERPIN 3 short core Poly-R (SP29). Accordingly, this example demonstrates that shortening the peptide resulted in instability and lack of function, while stabilizing with the poly-R flanks resulted in heightened activity.

Moreover, these peptides all contain a LRP1 binding site, however, when the LRP1 binding site was truncated to obtain SP31, the anti-inflammatory activity of the peptide was lost and could not be restored with the Poly arginine flanks (SP32 peptide). This indicates that SERPINs contain an anti-inflammatory core motif that is dependent on LRP1.

Example 2: Modification of SERPIN Peptides and Effects on LRP1 Binding

Figure 2:
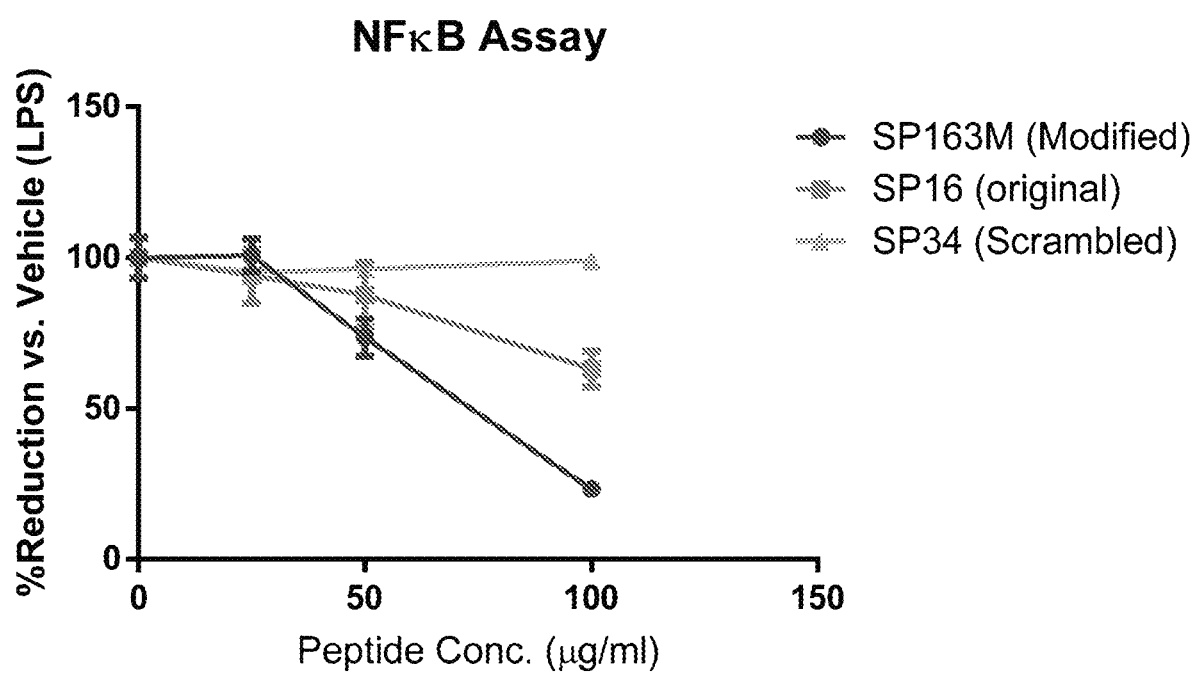
FIG. 2 demonstrates that SP163M peptide, which was obtained by modifying SP16 peptide to replace the rapidly oxidized methionine with Norleucine (Nle), as well as acetylation and amidation of the N and C-termini respectively, improved activity in the NFκB reporter assay following LPS stimulation.

To improve the bioavailability and stability of SP16, the peptide was modified by replacing the methionine with Norleucine (Nle) and acetylating and amidating the N and C terminus, respectively. The modified peptide is termed SP163M having the following sequence: VKFNKPFVFL [Nle]IEQNTK (SEQ ID NO. 35). Surprisingly, although one of the amino acids in the LRP1 binding site was mutated (M→Nle), SP163M significantly improved NFkB reduction in the reporter assay in comparison to the unmodified SP16 peptide, as shown in FIG. 2.

Figure 3:
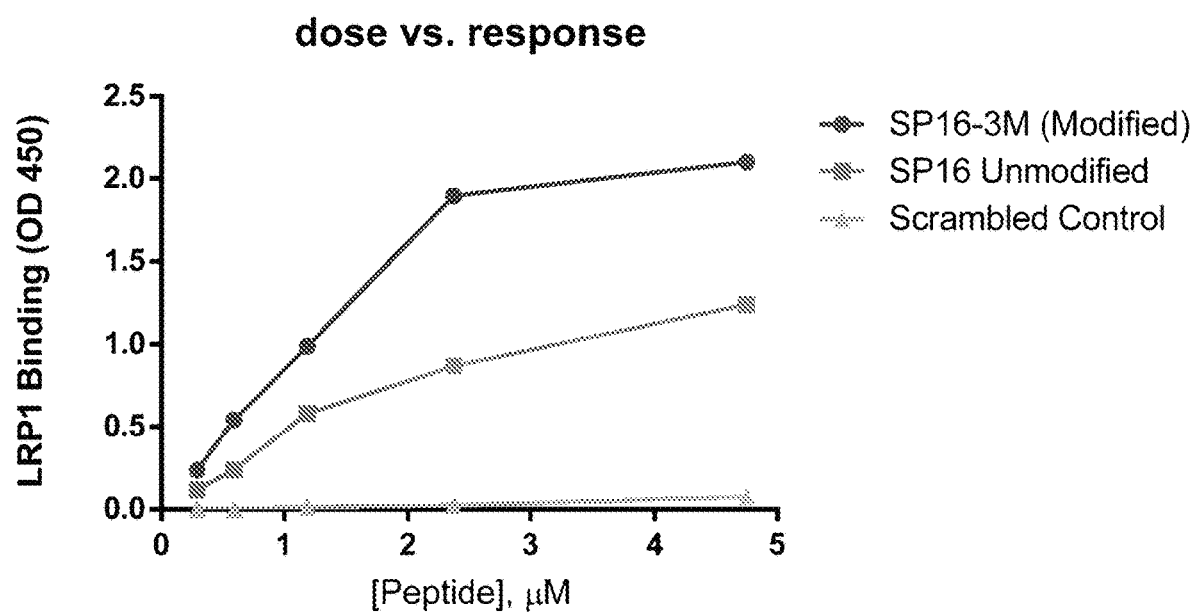
FIG. 3 demonstrates that SP163M peptide improved the affinity to LRP1 in a binding assay compared to SP16 peptide. However, no binding to LRP1 was observed with scrambled control SP34 peptide.

The two peptides were compared for their ability to bind to LRP1. Binding assays confirmed SP163M's improved binding capacity to LRP1 compared to unmodified SP16 peptide (FIG. 3). Recombinant LRP1 (Cluster II) bound to ELISA plate was exposed to increasing concentrations of biotinylated SP16 (unmodified), SP163M (modified) or scrambled control (SP34) before visualization using streptavidin HRP and substrate. SP16 and SP163M were capable of binding to LRP1 Cluster II, while SP34 containing the amino acids found in SP16 in scrambled orientation did not bind to LRP1 Cluster II.

Figure 4:
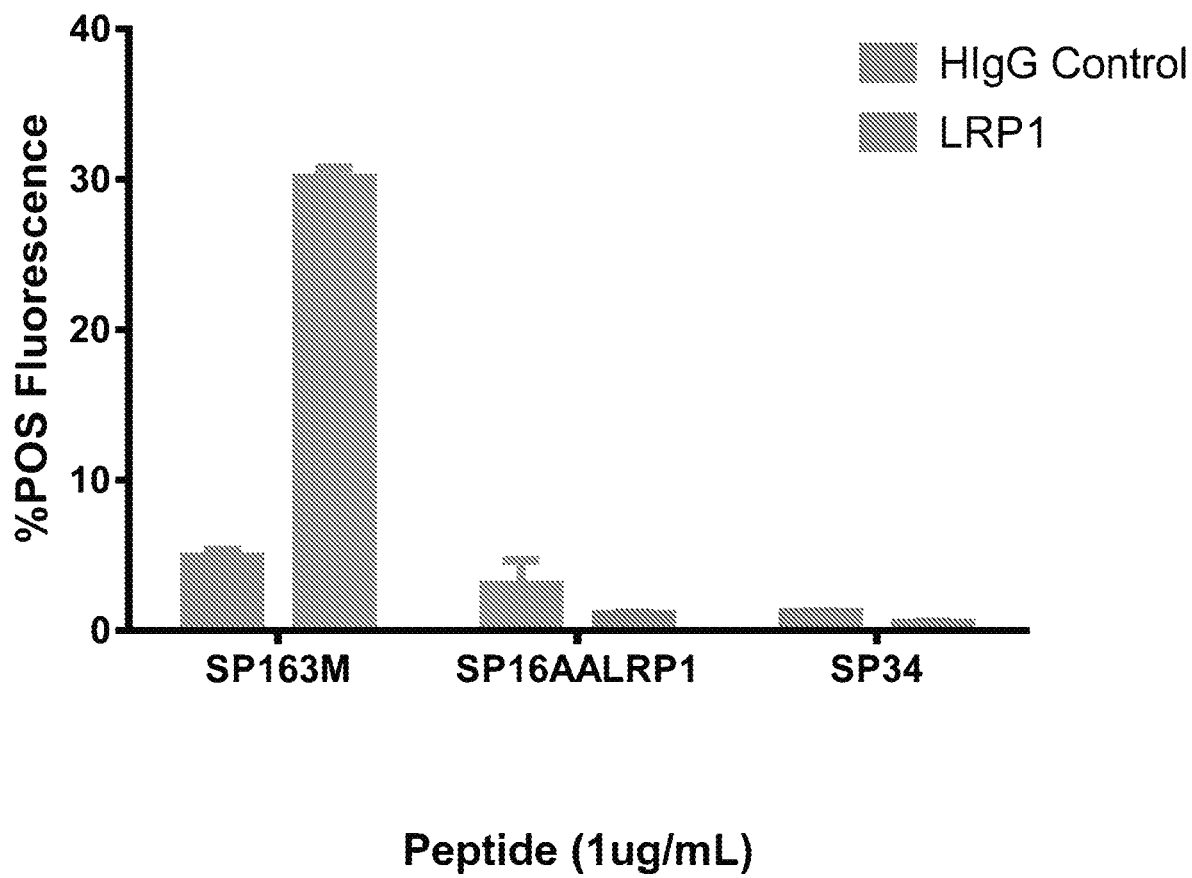
FIG. 4 demonstrates that the core motif containing the LRP1 binding site is necessary for SP163M binding to LRP1. When selected amino acids in the core motif were substituted with alanine, SP16AALRP1 did not bind to LRP1.

To confirm whether the proposed binding sequence FVFLM is where LRP1 interacts with the SERPIN peptides, SP16AALRP1 peptide having a sequence of VKFN-KAAAAAAIEQNTK (SEQ ID NO. 36) was used. Compared to SP16 or SP163M, this peptide does not contain the LRP1 binding site and two other amino acids are replaced with alanine. In this assay, direct binding was assessed, as recombinant LRP1-FC fusion protein (Cluster II), was bound to protein G beads (dynabeads protein G). SP163M, SP16AALRP1, and scrambled control (SP34) were labeled with a fluorescent dye (Cy5.5) and added to the LRP1 bound beads (each peptide at 1 µg/ml), before excess or non-bound peptide was washed thoroughly away. Human IgG was used as a random protein control bound to the beads. The fluorescence of the beads was measured by flow cytometry to show the level of peptide binding to LRP1. As shown in FIG. 4, SP16AALRP1 did not bind to LRP1 while the specific binding of SP163M to LRP1 was confirmed. SP163M did not bind to the IgG control. The scrambled control SP34 did not bind to LRP1 either. SP163M, which contains the LRP1 binding site in the correct sequence, was the only peptide demonstrated significant fluorescent signal in this experiment.

Figure 5:
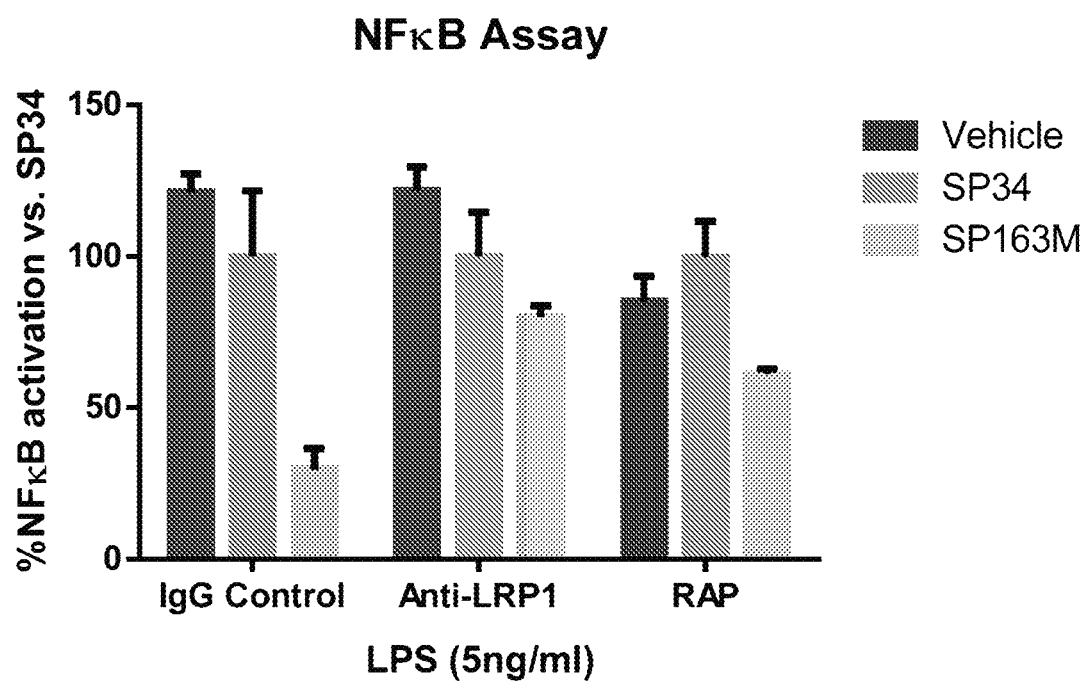
FIG. 5 shows that LRP1 mediated the in-vitro anti-inflammatory effects of SP163M and that blocking LRP1 with anti-LRP1 antibody (blocks LRP1 signaling) or RAP (receptor associated protein), a universal LRP1 ligand antagonist, abrogated this effect.

Next, whether blocking LRP1 signaling would have a negating effect on the peptides' ability to reduce NFkB activation was evaluated. The NFkB reporter assay was used and the cells were stimulated with LPS (5 ng/ml) to induce NFkB activity. SP163M (100 µg/ml) was added directly prior to each treatment. The cells were treated with an anti-LRP1 antibody that blocks LRP1 signaling (125 µg/ml), RAP (1 µM) (an LRP1 antagonist that blocks ligand binding), or an IgG antibody as a control 30 minutes prior to stimulation with LPS. FIG. 5 shows that SP163M mediated reduction in NFκB activation was negated when LRP1 was blocked, further indicating that the peptide's mechanism is through LRP1 binding.

Example 3: Effects of SERPIN Peptides on Neuropathic Pain

LRP1 has been shown to play a role in neuropathic pain. For instance, LRP1 agonists promote axonal regeneration (sprouting) and activates Schwann cell repair programs. In this example, adult dorsal root ganglion (DRG) were isolated from rats to assess the effects of SP163M on sprouting. FIG. 6A shows high-power representative phase contrast images of cultured primary adult DRG neurons at 48 hours. The DRG cultures were untreated (control), treated with Nerve Growth Factor (a powerful neurotrophic agent) (positive control), or treated with SP163M (100 or 500 ng/mL). SP163M at both concentrations robustly promoted sprouting. FIG. 6B shows low-power representative phase contrast images of cultured primary adult DRG neurons at 96 hours. The DRG cultures were untreated (control), or treated with SP163M (100 ng/mL). This figure suggests that not only did SP163M promote sprouting, but also promoted survivability of neurons. To test this, a quantitative Trypan blue assay was performed, in which survivability was assessed at 96 hours. The DRG neurons were treated with SP163M (100 ng/ml) or Neurotrophin Factor-3 (NT-3) as a positive control, 1% FBS acted as untreated controls. FIG. 6C shows that SP163M significantly ($p<0.05$) improved survivability of these neurons.

Figure 7A:
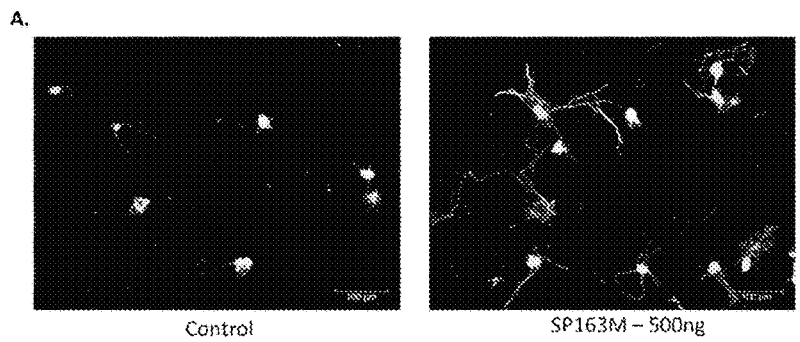
FIGS. 7A-7B show quantitative assessment through immunolabeling of beta-tubulin measuring the length of each neurite in the neuron cultures. SP163M treatment resulted in greater outgrowth of adult DRG neurons compared to control cells.
Figure 7B:
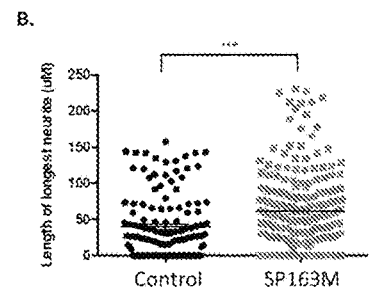

Sprouting in the DRG neuron cultures was further quantitatively assessed. Neuro-specific beta tubulin immunofluorescence was performed to measure the length of longest neurite in 300-400 cells per group. FIG. 7A shows representative images of cultured primary adult DRG neurons immunolabeled with beta tubulin. DRG cultures were treated with SP163M (500 ng/mL) at 0, 24, and 48 hours and fixed at 54 hours, and the untreated culture was used as control. In FIG. 7B the length of longest neurite after 54 hours was compared between SP163M and control. SP163M promoted neurite outgrowth of adult DRG neurons and significantly increased the length of longest neurites compared to controls ($p<0.005$).

Figure 8:
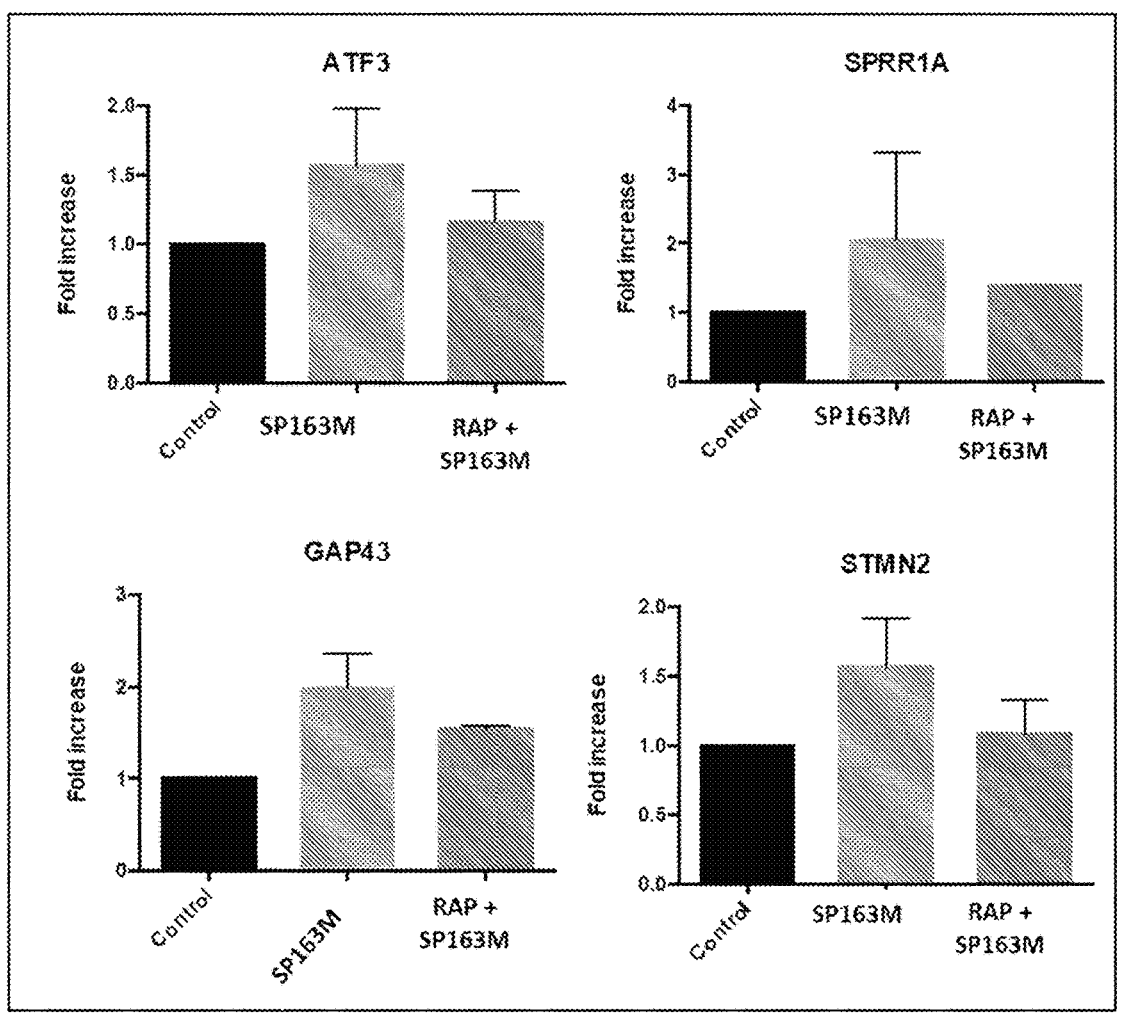
FIG. 8 shows that SP163M induced expression of Regenerative Associated Genes (RAGs) in cultured adult DRG neurons in an LRP1-dependent manner. When neurons were pre-treated with Receptor Associated Protein (RAP) to inhibit LRP1 binding, the expression of the RAGs were also inhibited.

In an effort to understand the molecular mechanisms underlying SP163M-induced neuronal sprouting, regenerative associated gene expression (ATF3, SPRRR1A, GAP43, and STMN2) changes at 72 hours were examined using qPCR. This test was to confirm that the observed sprouting effects were due to SP163M signaling via LRP1. RAP, which prevents binding to LRP1 and inhibits LRP1-dependent signaling, was used to pre-treat the cultures 1 hour prior to SP163M treatment (500 ng). Increased expression of regeneration associated genes (RAGs) by SP163M appeared to be blocked by RAP, suggesting that SP163M induced these changes via LRP1 (FIG. 8).

Next, a pain study was performed using the formalin pain test. This test is a tissue injury model that is widely used to screen potential pain therapeutics. In the model, formalin was injected subcutaneously into the hind paw, which induced a very reliable response consisting of a first phase and second phase. In the first phase, analgesic affects were tested as c-fiber activation due to peripheral stimulus (Substance P and Bradykinin) caused pain. During the second phase, there was an inflammatory reaction in peripheral tissue and central sensitization in spinal dorsal horn (histamine, serotonin, prostaglandin and bradykinin). SP163M was administered subcutaneously (50 µg) 1 hour prior to intraplantar formalin injection and then licking behavior was observed for 50 minutes. SP163M significantly reduced the first phase, and thus appeared to act as an analgesic via modulation of C fiber activity. Moreover, SP163M significantly delayed the start of the second phase, suggesting SP163M may act as an analgesic and may also modulate inflammation and/or central sensitization (FIG. 9).

Figure 10A:
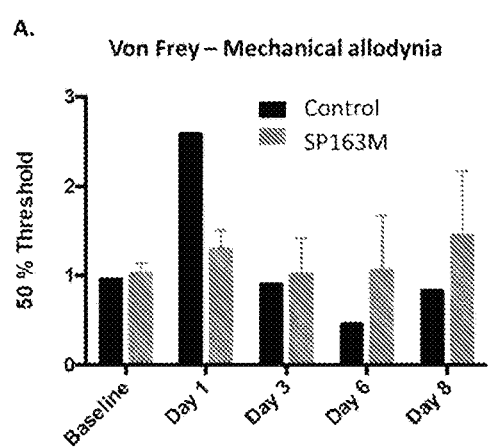
FIGS. 10A-10B show that in the partial Nerve Ligation (PNL) model, a well described neuropathic pain model, PNL induced significant tactile allodynia and thermal hyperalgesia in control mice after 3 days (black bars). In contrast, mice systemically treated with SP163M (red bars) showed reduced allodynia and hyperalgesia after PNL that was sustained throughout the study after injury (8 days).
Figure 10B:
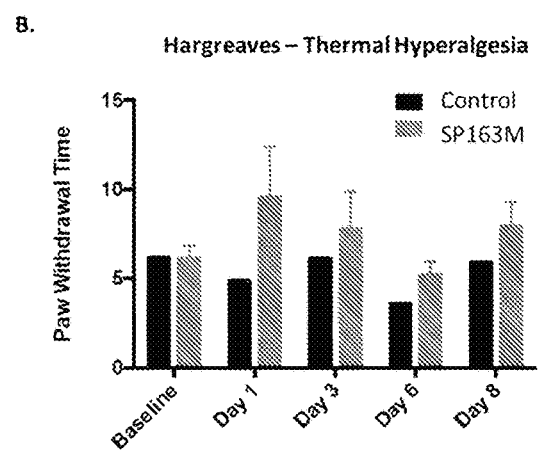

The efficacy of SP163M was tested in a partial nerve ligation model by testing evoked pain measurements, both thermal and mechanical. SP163M was administered 1 hour prior to surgery (50 µg). Mice were then surgically ligated around part of the sciatic nerve. Mice were measured for evoked pain behaviors following both mechanical (Von Frey) and thermal (Hargreaves) on days 1, 3, 6, and 8. SP163M increased the pain threshold of mechanical allodynia and increases the tolerance to heat (FIG. 10). Therefore, SP163M may have potential to serve an alternative to opioid analgesics for the treatment of chronic neuropathic pain.

Example 4: SERPIN Peptides Crossing BBB

Figure 11:
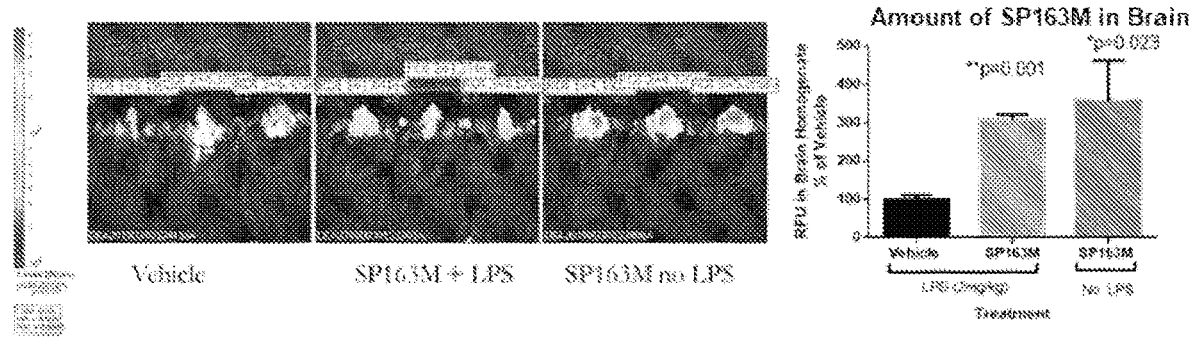
FIG. 11 shows in-vivo imaging of labeled SP163M (cy5.5). An hour after administration of 50 μg/mouse of the peptide, SP163M was present in the brain region. Fluorescent measurement of the brain homogenate 24 hours after administration of cy5.5SP163M, shows that SP163M was detectable.

Given the effects of SP163M on improving both survivability and regeneration of neurons, SP163M could have potential as a treatment for certain CNS related neurodegenerative diseases such as Alzheimer's disease. Experiments were carried out to determine whether SP163M could cross the blood brain barrier (BBB), as LRP1 has been used to deliver drugs across the BBB via LRP-1 receptor mediated transcytosis. To assess the bioavailability of SP163M in the brain, mice were injected with LPS (2 mg/kg), and then 1 hour later injected with labeled SP163M (cy5.5) (50 µg) or vehicle. At 1 hour, 24 hours and 1 hour after the second dose of SP163M (25 hours), the mice were imaged for fluorescence in-vivo and then brain homogenate and serum were collected around 24 hours for measurement of fluorescence. FIG. 11 shows in-vivo fluorescence signal (indicating presence of SP163M) in the region of interest (brain) as soon as 1 hour after the first dose. Furthermore, collection of the whole brain and measuring the fluorescence in the homogenate showed a 3-4-fold increase in fluorescent intensity in mice treated with SP163M*Cy5.5 over vehicle after 2 doses (I.V.). The permeability Index (which was calculated based on the tissue fluorescence/weight and serum fluorescence/mL) showed no difference between SP163M in mice treated with LPS vs. non-treated mice. Therefore, SP163M reached the brain regardless of whether inflammation was present.

Example 5: Anti-Viral Effects of SERPIN Peptides

Figure 12:
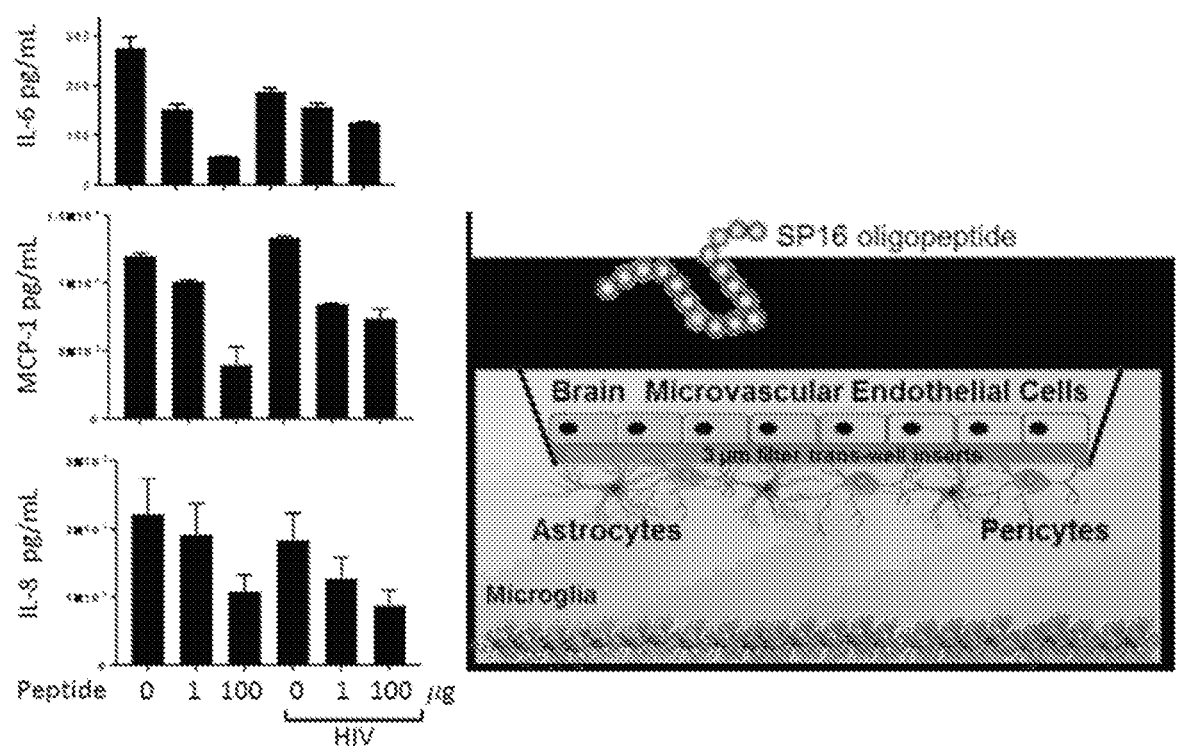
FIG. 12 shows that a 3D-blood brain barrier (BBB) was constructed on a 3 μM trans-well insert. When microglia were treated with SP163M, and then infected with HIV causing cytokine secretion, SP163M treatment resulted in reduced cytokine concentration (pg/ml) following HIV infection.

SERPINs have been found to have broad-spectrum antiviral activity, for instance, in HIV. However, SERPINs have also been shown to play both positive and negative roles in the progression of chronic viral illnesses. Abnormally low alpha-1 anti-trypsin (AAT) levels have been observed in both HIV-1 and HCV infection and have been shown to correlate with progressive disease or the development of liver fibrosis, respectively. Conversely, there is mounting clinical evidence suggesting an association between increased levels of SERPIN expression and reduced incidence of HIV acquisition, or protracted disease progression. LRP1 plays an essential role in mediating anti-inflammatory cell signaling and modulation of several cytokines. Ligands to LRP1 have a similar anti-inflammatory activity. After ligand binding, the cytoplasmic fragment of LRP1 undergoes proteolysis by γ-secretases and migrates to the nucleus, where it binds to the interferon regulatory factor-3 (IRF-3) and promotes its nuclear export and proteasomal degradation, thus limiting the expression of the pro-inflammatory genes in cultured fibroblasts and macrophages.[55] The LRP1-agonist complex was also found to inhibit the interleukin-1 receptor associated kinase-1 (IRAK-1), leading to the down-regulation of the NF-kB pro-inflammatory signaling pathway in vascular smooth muscle cells.[19] Therefore, SP163M's ability to inhibit HIV mediated pro-inflammatory cytokines and the transcytosis of SP163M in an in-vitro BBB model were tested. A 3D-BBB was constructed on a 3 µM trans-well insert. Microglia with or without HIV on a BBB insert were treated with increasing concentrations of SP163M (up to 100 µg/ml). Cytokines IL-6, MCP-1 and IL-8 were assessed after 24 hours. FIG. 12 shows HIV induced IL-6, MCP-1 and IL-8 were significantly decreased in microglia treated with increasing concentrations of SP163M.

Example 6: Effects of SERPIN Peptides on Neuroinflammation

Figure 13:
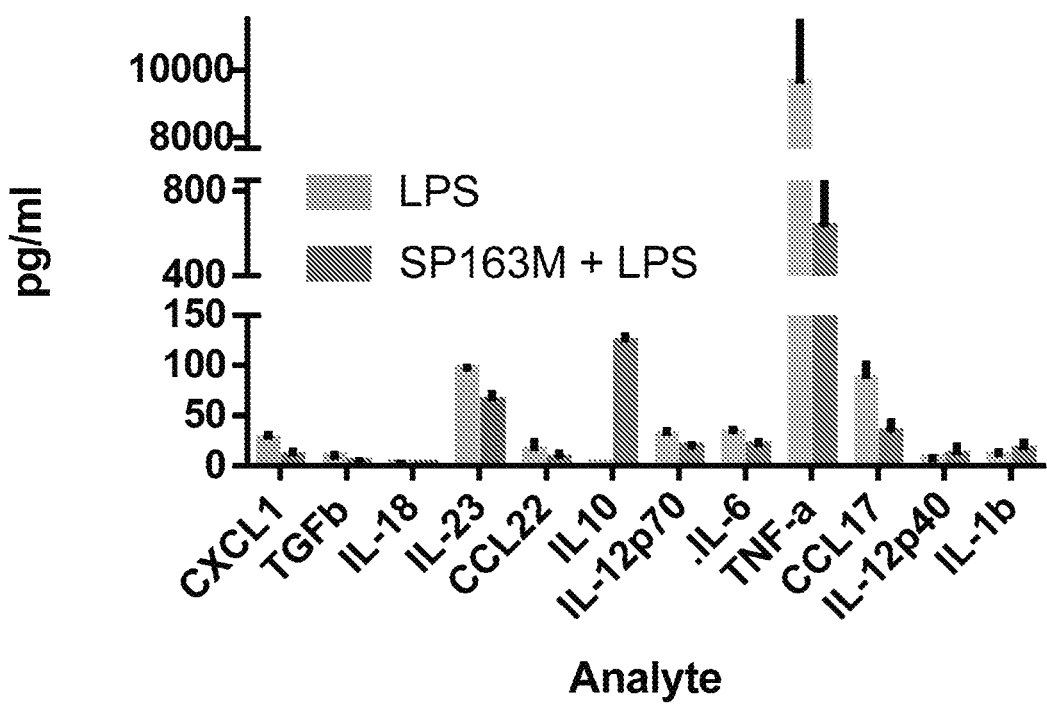
FIG. 13 shows that SP163M reduced neuroinflammation in-vitro. Treatment of microglial cells with SP163M reduced LPS induced cytokine production, particularly TNFα. However, IL-10, an anti-inflammatory cytokine, was increased with SP163M treatment compared to vehicle.

LRP1 has been shown to be involved in the development of neurodegenerative diseases and in the regulation of the metabolism of amyloid-β peptides (Aβs) in the brain and periphery. Neuroinflammation plays a critical role in neurodegenerative disease, such as Alzheimer's Disease (AD). Reactive glia cells (such as microglial cells) play a key role in both disease initiation and progression becoming activated through dysregulated clearance of beta amyloid and other damage associated molecular patterns (DAMPs).[13] AB deposition and tau hyper-phosphorylation contribute to microglial activation, NFκB inflammatory pathway activation and release of pro-inflammatory cytokines such as TNFα, IL-6 and IL-1β, which contribute to neuronal damage and loss. Therefore, the cytokine profile was explored in LPS induced microglial cells treated with SP163M. In microglial cells, SP163M reduced LPS mediated cytokines (largely TNF-alpha, p<0.02), while highly upregulating IL-10 (anti-inflammatory cytokine) in LPS treated cells (FIG. 13). The IMG microglial cells were treated with SP163M (100 μg/ml), 24 hours with and without LPS (100 ng/ml). Cytokines levels (pg/ml) in the supernatant were measured by multiplex assay.

Example 7: Effects of SERPIN Peptides on Autophagy

Figure 14A:
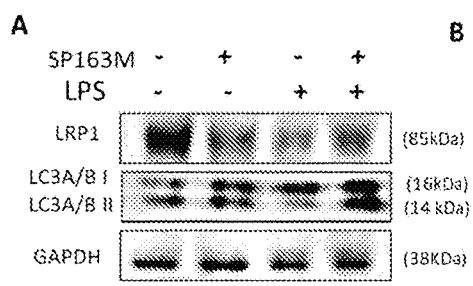
FIGS. 14A-14C show that SP163M regulated autophagy during inflammation. Microglial cells were treated with SP163M and then exposed to LPS. Western blot analysis of the LC3 II to LC3 1 ratio (initiation of formation of autophagosomes—a biomarkers widely used to detect autophagy) shows that SP163M increased autophagy and LRP1.
Figure 14B:
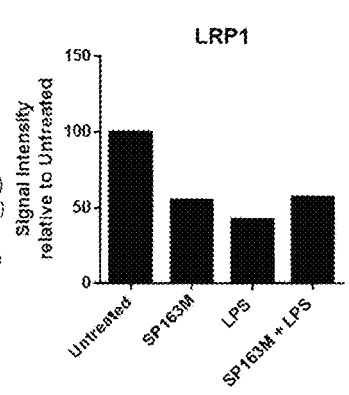
Figure 14C:
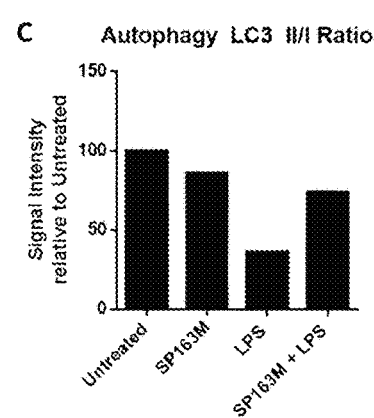

In addition to neuroinflammation, impaired autophagy, a homeostatic process that degrades and recycles proteins such as beta amyloid, has been associated with AD.[7] LRP1 has been shown to mediate healthy lysosomal processing associated with autophagy. Therefore, through LRP1, SP163M has potential to mediate several aspects of AD including healthy cell metabolism to reduce the spread of protein aggregation, alleviate neuroinflammation and improve neuronal dysfunction leading to survival and possibly regeneration of these cells. The effects of SP163M on autophagy markers were tested in microglial cells. IMG microglial cells were treated with SP163M (100 μg/ml) before addition of LPS (100 ng/ml) for 24 hours. Lysates were collected and western blot analysis of both LRP1 and microtubule-associated protein light chain 3 (LC3 I and II) was performed. The LC3II/I ratio, a commonly used marker for autophagy indicating autophagic flux, was determined. FIG. 14 shows that in LPS activated microglial cells, the level of LRP1 in the lysate was decreased (perhaps an indication of increased LRP1 shedding). SP163M increased LRP1 protein expression in LPS activated microglial cells. LPS also significantly reduced autophagy induction, in which SP163M was capable of restoring to near basal levels. These results indicate another mechanism by which SP163M regulation of LRP1 contributes to homeostatic balance of dysregulated cell processes.

Example 8: Effects of SERPIN Peptides on Inflammation and Tissue Injury

Figure 15:
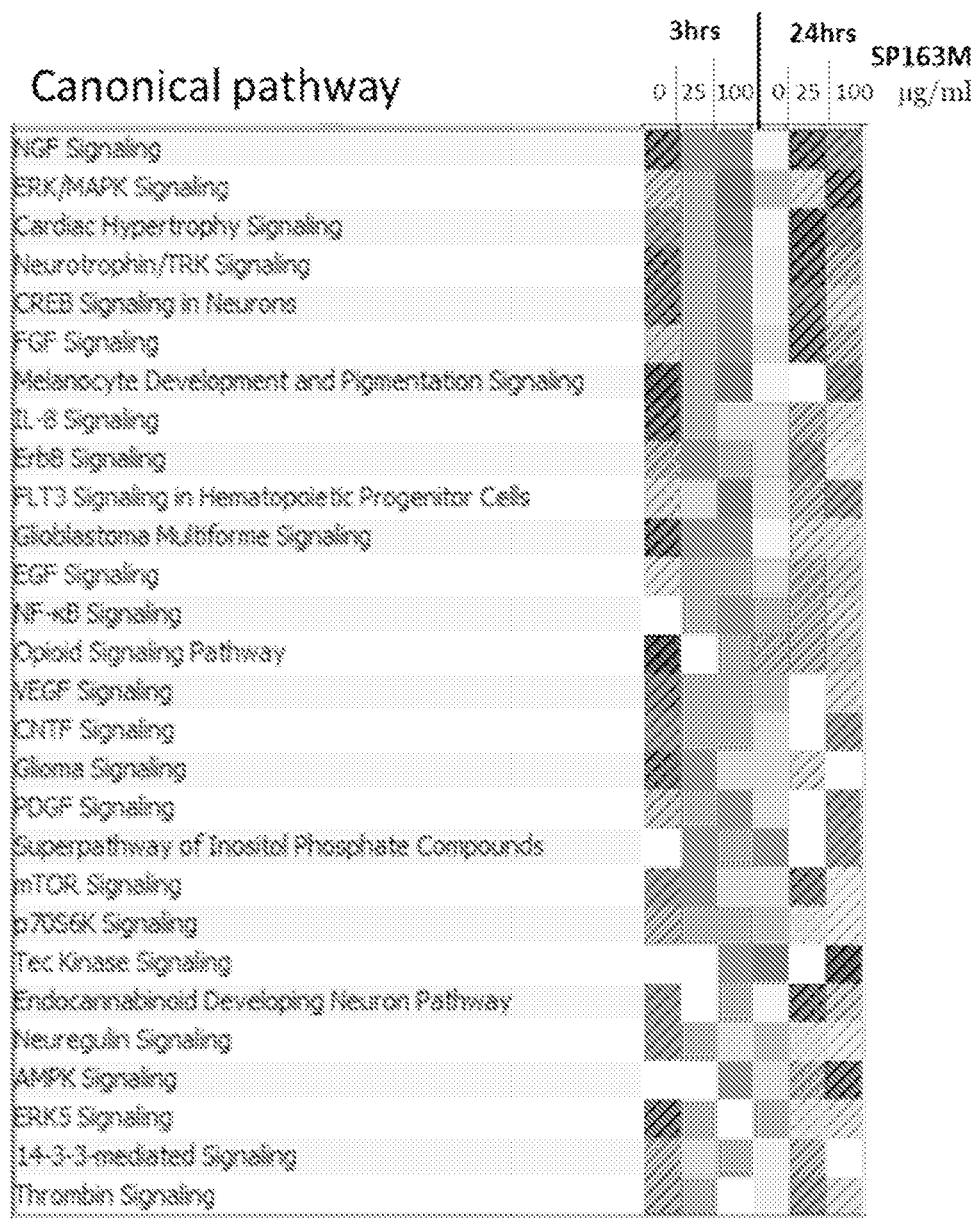
FIG. 15 shows that SP163M treatment uniquely targeted LRP1 to regain homeostasis during inflammation. Using proteomic signaling pathway analysis in an inflammatory model of LPS stimulated human immune cells (THP1 monocytes), SP163M treatment distinctly counteracted LPS induced suppression (early time-points) or activation (later time-points) of many canonical pathways involved in inflammation, cell death/survival and metabolic regulation. These results, and subsequent proteomic signaling analysis obtained from other cell lines/treatments treated with SP163M (not shown) indicate that SP163M works through LRP1 controlled signaling pathways such as apoptotic pathways (TLR, NFκB and caspase), cell metabolism/autophagy (mTOR), and cell injury and survival (Akt, ERK/MAPK).
Figure 17:
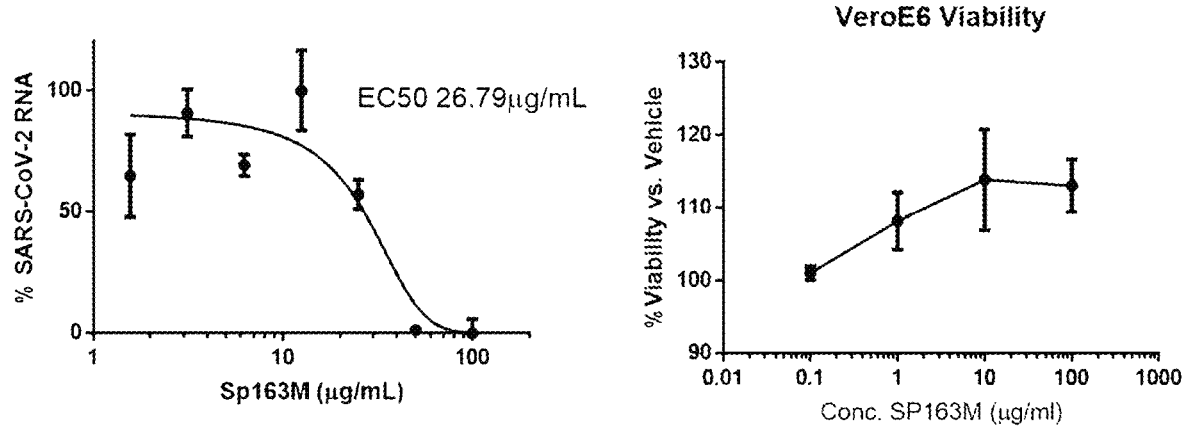
FIG. 17 shows that SP163M significantly reduced SARS-CoV-2 replication in infected Vero-E6 cells and did not cause toxicity to these cells at effective concentrations up to the highest concentration tested. Treatment with SP163M (100 µg/ml) suppressed viral replication in SARS-CoV-2 (USA-WA1/2020) (MOI 0.1) infected Vero cells SP163M suppressed SARS-COV-2 replication.
Figure 18:
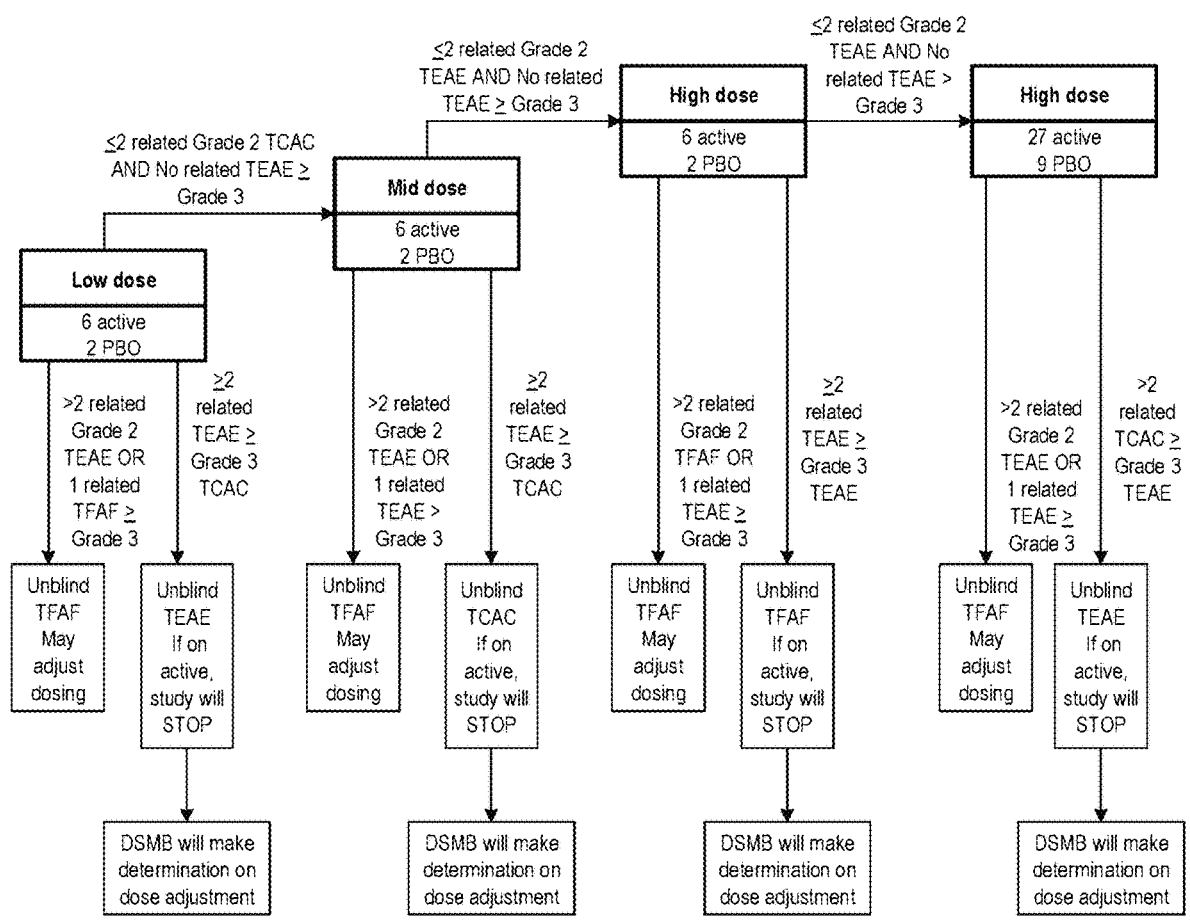
FIG. 18 illustrates a study design for testing SP163M in SARS-COV2 infected subjects.

SP163M works through the innate immune system to mitigate damaging inflammation and tissue injury to subsequently regulate the immune response and promote healing. A novel proteomic signaling pathway analysis was used to assess the impact of SP163M on the host dynamics following infection and treatment. SP163M was tested at various doses and time-points challenged with three distinct agents: an endotoxin (LPS) (bacterial agent), a highly inflammatory virus (Venezuelan Equine Encephalitic Virus), and a febrile virus known to cause mortality, particularly when host immune responses are dysregulated (Rift Valley Fever Virus). The heatmap of the top canonical pathways that were significantly changed in response to each insult shows that, regardless of the agent used, SP163M counteracted these changes, restoring the profile back to a normal state (canonical pathway heatmap for LPS shown in FIG. 15). The cell signaling profile of SP163M that emerged from these studies indicates mediation of several key pathways that contribute to sepsis progression and severity such as inflammatory and apoptotic pathways (TLR, NFκB and caspase), cell metabolism/autophagy (mTOR), and cell injury and survival (Akt, ERK/MAPK). This study elucidates the homeostatic nature of SP163M that could aid in correcting the dysregulated immune responses that leads to progression of many neuroinflammatory and infectious diseases.

Example 9: Effects of SERPIN Peptides on Acute Lung Injury

Given the role of LRP1 in regulating the host responses, SP163M's ability to restore homeostasis following acute lung injury was tested. LRP1 plays a key role in regulating lung inflammation during injury or infection. LRP1 regulates inflammatory signaling pathways (i.e. NFκB, JNK) to control the cytokine output, and contributes to effective migration and phagocytosis.[22,26,51] In neutrophils, LRP1-dependent mechanisms lead to enhanced cell adhesion, chemotaxis, and antibacterial effects of these cells, thereby resisting immunosuppression[25]. During acute infection or injury, LRP1 also promotes inflammatory resolution through scavenging PAMPS and DAMPS (pathogen and damage associated molecular patterns) (from dying or injured tissue), to prevent tissue injury[25]. LRP1 was also shown to mediate autophagy during infection, an important metabolic process recently shown to play an important protective role in infectious lung disease.[47] LRP1 also controls many signaling pathways important for appropriate tissue repair, particularly important in preventing lung fibrosis.[49,50] Therefore, because of its multifunctional ability to regulate lung inflammation, targeting LRP1 has substantial potential to mitigate several aspects of the dysregulated immune response that contributes to acute respiratory distress syndrome (ARDS) progression.

SP163M was tested in an acute septic model of *Klebsiella pneumonia* (KP) infection, to determine whether SP163M is a viable treatment option for patients with severe lung infection. To assess the bioavailability of SP163M in the lung and tissues, C57BL/6 mice were treated with two doses of Cy5.5-SP163M (12 mg/kg) 24 hours apart. Plasma, liver, kidney and lung were collected and analyzed for SP163M (Fluorescence) at 1 hour after 1 dose (1 dose peak), 23 hours after 1 dose (1 dose trough) and 1 hour after second dose (2 dose peak). FIG. 16A demonstrates detection of SP163M in the plasma, liver, kidney, and lung, indicating 1-23 hours post-KP exposure as an appropriate time-frame for SP163M treatment. Next, survival and weight loss were assessed in the KP septic model. C57BL/6 mice (n=15) were treated with SP163M (12 mg/kg) or vehicle control starting 1 hour after intranasal exposure of 600 CFU KP (LD100). Survival was assessed over 14 days. Daily SP163M treatment (13 doses total) resulted in a significant benefit in survival of 40% (p<0.02) vs. vehicle control (FIG. 16B). A decrease in weight loss was also observed with SP163M treatment (FIG. 16C).

Example 10: Effects of SERPIN Peptides on COVID Infection

Figure 21:
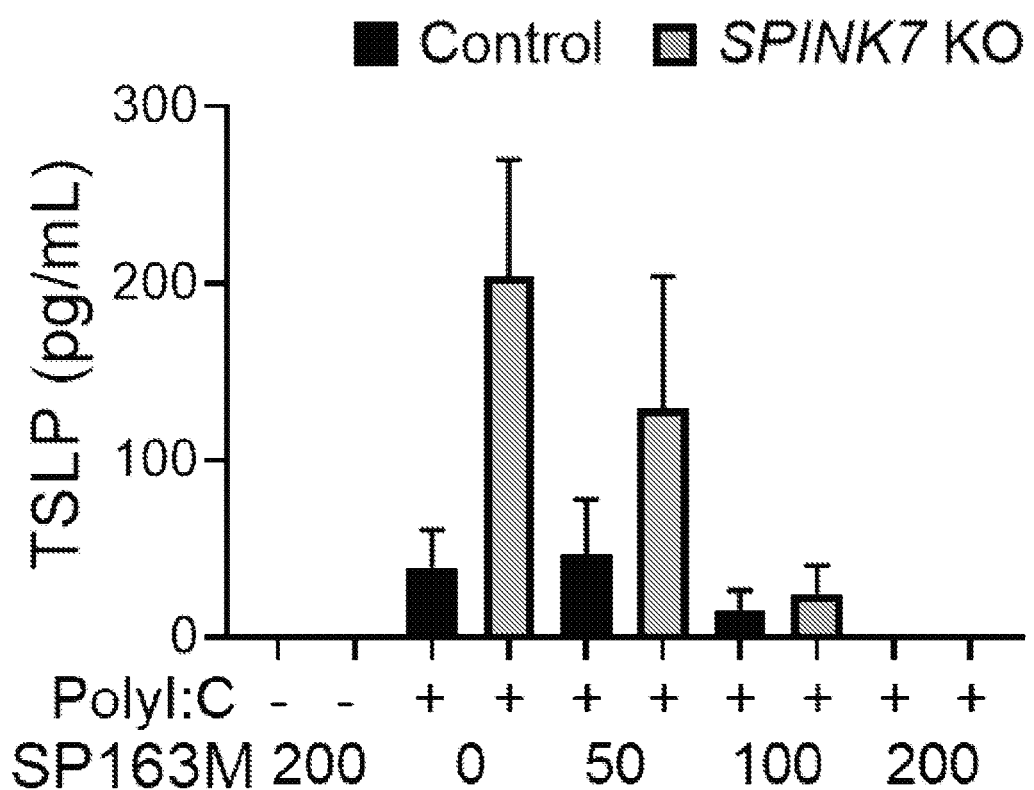
FIG. 21 shows that SP163M inhibited the cytokine TSLP production in SPINK7 knockout cells in a dose-dependent manner.

Due to the profound effects of LRP1 in mitigating lung injury and regulating host mediated responses during viral infection, SP163M's anti-viral effects in SARS-CoV-2 infected cells were tested. Surprisingly, SP163M was able to significantly reduce viral replication. Vero cells were pre-treated for one hour with SP163M or vehicle control, medium removed, infected with SARS-CoV-2 (USA-WA1/2020 Strain) (MOI 0.1), inoculum removed, and post-treated with peptide. Virus in supernatant was measured by RT-qPCR at 48 hours infection. The dose response curve shows that at a dose of 100 μg/ml, SP163M inhibits SARS-CoV-2 RNA significantly (FIG. 17A). The viability of the Vero cells treated with increasing concentrations of SP163M were tested and rather than showing any toxic effects to the cells, SP163M increased the viability as tested by cell-titer-glo assay (FIG. 17B).

Next, the safety and tolerability of SP163M in subjects with pneumonia due to severe acute respiratory syndrome coronavirus 2 (SARS-CoV-2) are to be tested. Reduction or change in plasma levels of inflammatory cytokines including interleukin-1 beta (IL-1β), tumor necrosis factor-alpha (TNF-α), interleukin-6 (IL-6), and interleukin-8 (IL-8) is compared to baseline or placebo treated subject. Additionally, reduction or change of acute phase reactants (c-reactive protein (CRP), α-2 macroglobulin, fibrinogen, and D-dimer) is compared with baseline or placebo treated subject. The number or proportion of subjects requiring invasive and noninvasive mechanical ventilation over a 2-week period, the number or proportion of subjects showing improvement in oxygen saturation ($SpO_2$) level as defined by both $SpO_2$>95% and respiratory rate 20/minute after 1 day or 1 dose of treatment, the time (days) on ventilator for subjects requiring invasive or noninvasive mechanical ventilation, the duration (days) of hospitalization, the time to clinical improvement (TTCI), which is defined as a National Early Warning Score 2 (NEWS2) of 2 to be maintained for 24 h (within a 2-week time frame), the number or proportion of subjects experiencing TTCI, which is defined as NEWS2 of 2 to be maintained for 24 h (within a 2-week time frame), all-causes mortality over study days 1-14, and/or change from baseline on Days 6 and 14 in Horowitz index or $SpO_2/FiO_2$ are assessed in SP163M-treated vs. placebo-treated subjects. FIG. 18 illustrates an example of the study design.

FIG. 19A illustrates the mechanism of the SERPIN peptides suppressing COVID-19 replication in cells via protease inhibition. TMPRSS2 processes the S protein on the SARS-CoV2 envelope in a process called priming. Priming of the S protein is necessary for binding between the S protein and the host receptor ACE2. TMPRSS2 inhibitors, such as camostat mesylate, A1AT, AEBSF, and BHH prevent the priming of the S protein and therefore block virus entry. In addition, inhibition of TMPRSS2 prevents processing of ACE2, which decreases the infectivity of the coronavirus. FIG. 19B shows the inhibitory effect of SP163M against TMPRSS2 at various concentrations. The IC50 of SP163M was 1125 ng/m L.

Example 11: Effects of SERPIN Peptides on Viral Infection

SP163M was also found to inhibit replication in other RNA viruses. Experiments were performed to analyze the impact of SP163M on alphavirus replication. Vero cells or primary astrocytes were pretreated for one hour with SP163M or water control, infected with VEEV TC83 luciferase virus (MOI 0.1), and post-treated with peptide. Luminescence was measured at 16 hours post infection. SP163M treatment reduced VEEV replication in Vero cells (FIG. 20A), primary astrocytes (FIG. 20B), and primary pericytes (data not shown). The EC50 of SP163M was 67.12 ug/ml in astrocytes. Treatment with SP163M was non-toxic to these cells at up to 100 μg/ml (data not shown). SP163M also inhibited EEEV replication as demonstrated through an EEEV luciferase reporter virus with an EC50 of 0.84 ug/mL indicating that SP163M was a more potent inhibitor of EEEV replication (FIG. 20C). Cells were infected with EEEV nano-luciferase reporter virus and treated as in previous experiments with VEEV reporter virus.

Because SP163M targets host responses, it could have broad spectrum utility with other viral agents. To better understand whether SP163M's action is alpha-virus specific, RNA or DNA specific or whether it has broad spectrum effects throughout many different viral families, a viral screen was performed with a panel of both RNA and DNA viruses. Of the viruses screened, only one DNA virus, Epstein Barr virus showed any anti-viral activity. Surprisingly, SP163M showed EC50 in many of the RNA viruses tested, with comparable activity to that of VEEV, among them influenza H1 N1, yellow fever virus and Dengue fever virus (Table 2).

TABLE 2

| EC50 of Peptide | | |
|---|---|---|
| Virus Screened | EC50 (μg/mL) | Cell Type |
| Epstein Bar Virus | 38.7 | Akata |
| Dengue virus 2 | 47 | Huh7 |
| Rift Valley fever virus | 17 | Vero 76 |
| Enterovirus-71 | 47 | Vero 76 |
| Western equine encephalitis virus | 63 | Vero 76 |
| Influenza A H1N1 | 47 | MDCK |
| Measles | 47 | Vero 76 |
| Yellow Fever Virus | 47 | Huh7 |

*Cell Toxicity tested and found to be >150 μg/ml in each cell line (top cone, tested).

Example 12: Effects of SERPIN Peptides on Eosinophilic Esophagitis

In terms of Eosinophilic Esophagitis (EoE), A1AT has been shown to attenuate experimental EoE in a murine model and in vitro. It is unknown if A1AT effects are mediated by inhibition of proteolytic activity or through activating LRP1 signaling. Although patients with eosinophilic asthma have lower LRP1 and in animal models, loss of LRP1 is associated with worsened allergic responses. SP163M does not contain any sequences for antiprotease activity, and is likely working through mediation of LRP1, not through proteolytic activity. Evidence shows that loss of esophageal expression of the serine peptidase inhibitor, kazal type 7 (SPINK7) is an upstream event in EoE pathogenesis. Therefore, the in-vitro effects of SP163M were tested in reducing thymic stromal lymphopoietin (TSLP), a key immune checkpoint cytokine involved in stimulating dendritic cells to polarize the generation of type 2 T cells (Th2), key cells involved in EoE pathogenesis, following loss of SPINK7. FIG. 21 shows that SP163M inhibited polyI:C-induced TSLP production by SPINK7 knockout EPC2 cells (Human esophageal epithelial cells). SPINK7 KO cells and control cells were plated in high calcium and high density, for 48 hours before being treated with SP163M (0, 50, 100 and 200 µg/ml) and Poly I:C (5 µg/ml, or untreated) for 8 hours. TSLP production in the supernatant was measured by ELISA.

Figure 22:
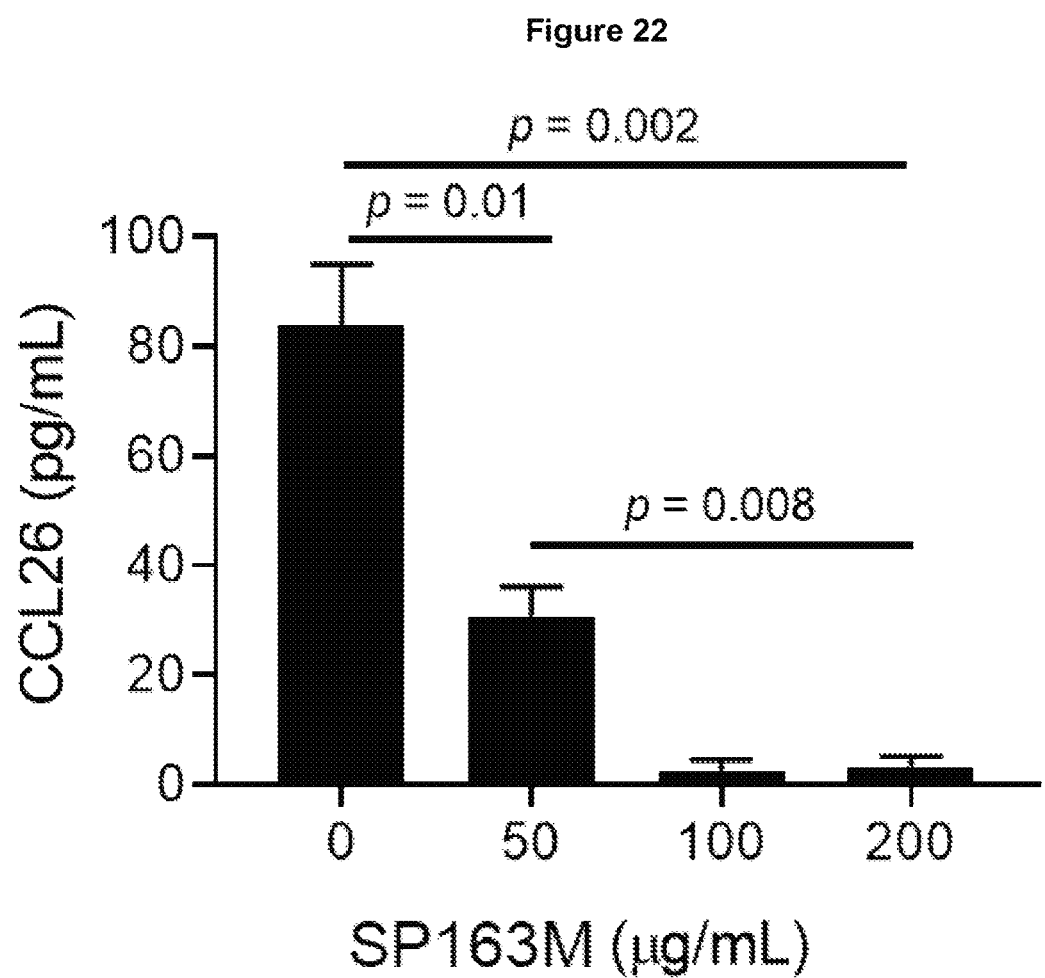
FIG. 22 shows that primary esophageal epithelial cells (EPC2) were treated with SP163M and then stimulated with IL-13, a TH2 response mediated cytokine, to induce CCL26. The figure shows that SP163M significantly reduced CCL26 release dose dependently.
Figure 23:
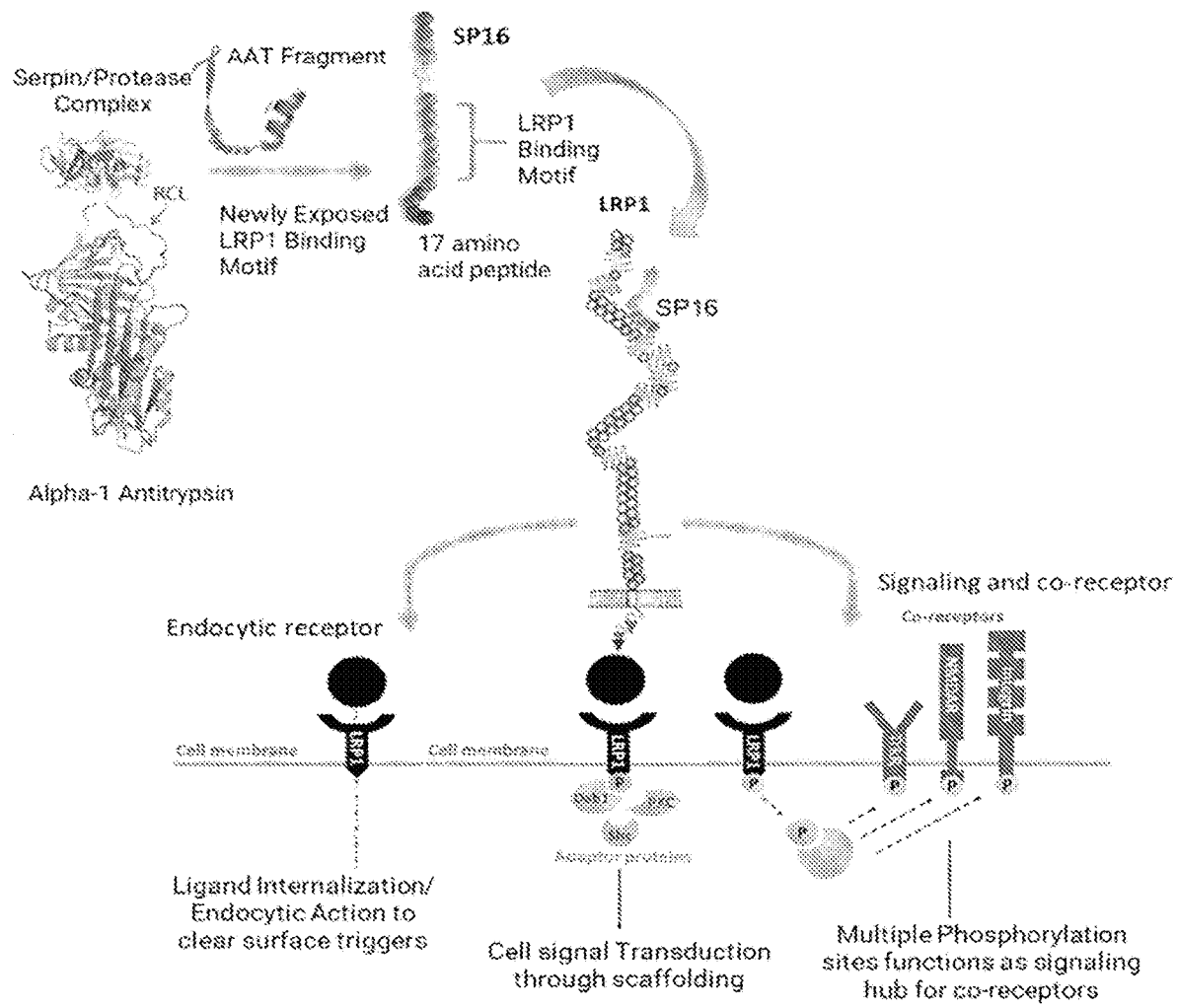
FIG. 23 illustrates the mechanism of action of SP16. SP16 is a derivative of the Serpin, Alpha-1 Antitrypsin (AAT). When AAT interacts with its target protease, a conformational change occurs that exposes a short motif that targets LRP1. From this fragment, a short (17AA) peptide (SP16) was excised and modified to obtain derivatives such as SP163M. The peptide retains the anti-inflammatory properties of AAT without the protease inhibitor function. SP16 binds to LRP1 and activates specific LRP1 mediated functions and cell signaling cascades that contribute to rebalancing immune responses to regain homeostasis and protect cells from injury.

Next, whether SP163M had any effects in mitigating a key chemoattractant for eosinophils, CCL26, was investigated. CCL26 is upregulated in the inflamed esophageal mucosa of EoE patients and the CCL26 gene is highly upregulated in the esophagus, according to genomic research. Molecular studies and animal models have implicated the importance of two key cytokines, IL-5 and IL-13 in the disease, which can stimulate release of CCL26 in EPC2 cells. FIG. 22 shows that SP163M significantly (p<0.002) reduced IL-13 induced CCL26 release in EPC2 cells. EPC2 cells were treated with SP163M (50, 100, and 200 µg/ml) and then stimulated with IL-13 (10 ng/ml) for 18 hours. CCL26 (pg/ml) in the supernatant was measured via ELISA.

Example 13: In Vitro Anti-Inflammatory Effects of SERPIN Peptides

Figure 24A:
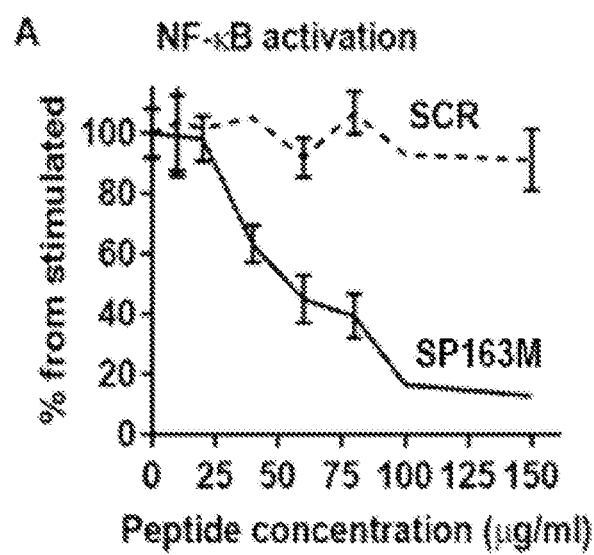
FIGS. 24A-24B demonstrate the anti-inflammatory activity of SP163M.
Figure 24B:
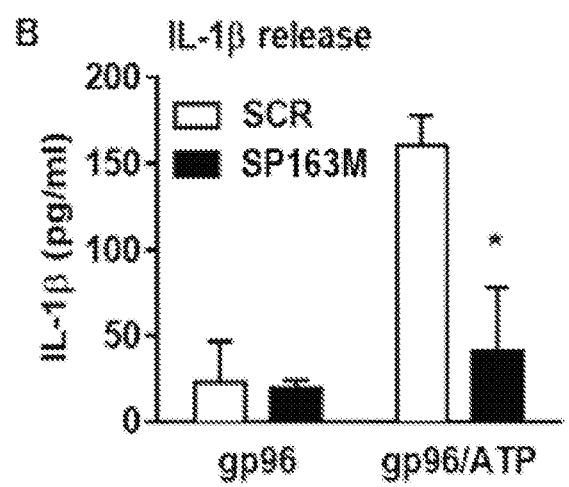
Figure 25A:
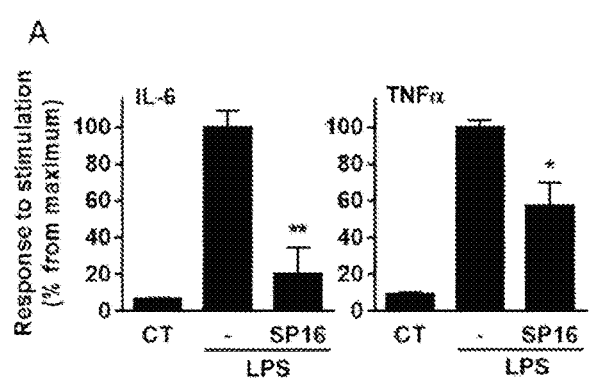
FIGS. 25A-25B show the effect of SP16 on LPS induced cytokine production in murine macrophages.
Figure 25B:
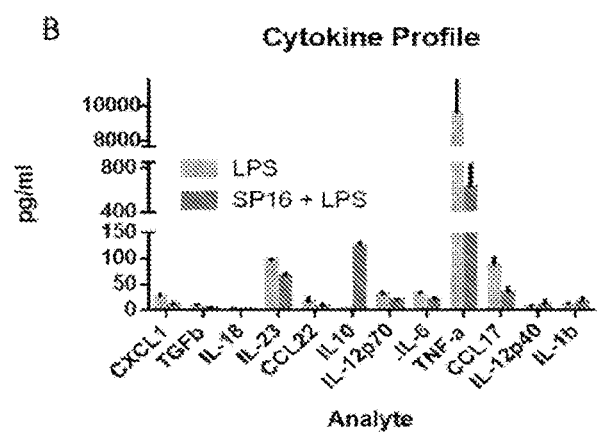

In an NFκB reporter cell line, SP163M caused a concentration-dependent reduction in LPS mediated NFκB activation as compared to a scrambled control peptide (FIG. 24A). GP96 is a heat shock protein and DAMP important in cell injury which activates the inflammasome contributing to IL-1β release. SP163M reduced inflammasome mediated IL-1β release following GP96 and ATP stimulation in macrophages (FIG. 24B). In macrophages, SP16 treatment significantly reduced cytokine TNFα (p<0.05) and IL-6 (p<0.01) following LPS stimulation (FIG. 25A). In microglial cells, SP16 reduced LPS mediated cytokines (largely TNF-alpha, p<0.02), while highly upregulating anti-inflammatory IL-10 (FIG. 25B).

In terms of cell survival and regeneration, studies in primary dorsal root ganglion neurons show that SP163M (100 ng) robustly promoted neuronal survival, axonal growth, and expression of regenerative associated genes, such as ATF3, in ex-vivo cultures (FIG. 26).

Example 14: In Vivo Anti-Inflammatory Effects of SERPIN Peptides

Figure 27A:
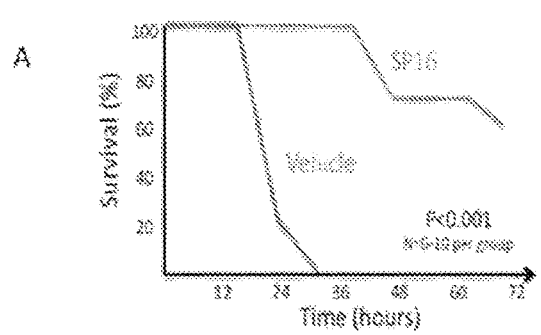
FIGS. 27A-27B demonstrate that SP16 reduced mortality and cytokines in endotoxemia model.
Figure 27B:
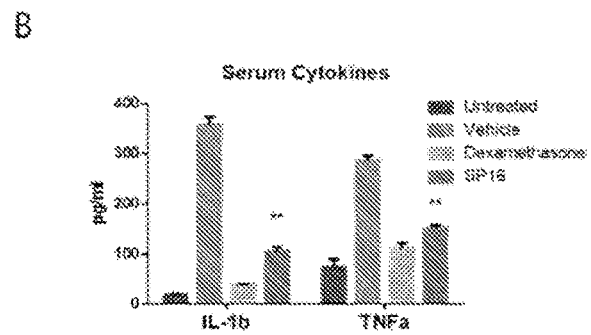

Studies in sepsis models demonstrate the potential therapeutic utility of SP16 to prolong survival and quench the pro-inflammatory cytokine response. Using a mouse model of lethal endotoxemia, in which mice were challenged with LPS (15 mg/kg), resulting in 100% mortality by 36 hours, the assessment brings focus to the potential of SP16 to regulate the cytokine storm underlying sepsis. In this model, all mice treated with SP16 survived (100% survival between 30 and 42 hours), whereas all control mice died (no survivors by 30 hours in the vehicle control group). SP16 treated animals displayed prolonged survival, 60% survival by 72-hrs (p<0.001 vs. vehicle) (FIG. 27A). In addition, significant reduction of IL-1β and TNFα serum levels were observed in challenged mice treated with SP16. This is congruent to the outcomes from high-dose levels of dexamethasone (FIG. 27B). SP16 was consistently shown to reduce TNFα, IL-6, and IL-1β, some of the most prominent and reliable biomarkers for predicting morbidity and mortality in sepsis.

Figure 28:
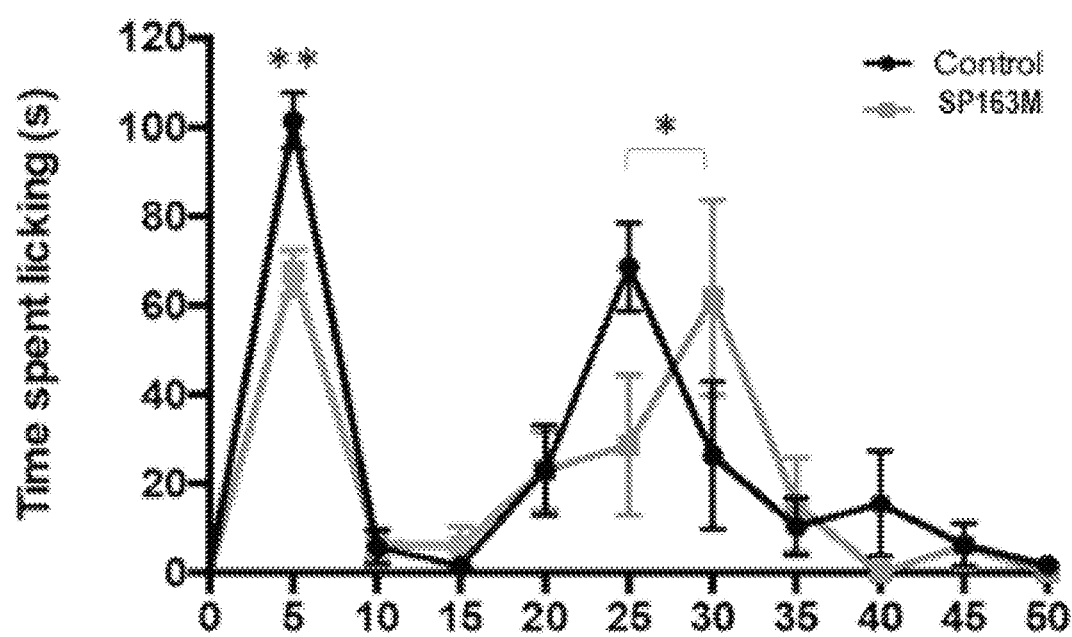
FIG. 28 demonstrate that SP163M has anti-inflammatory and analgesic activity in formalin pain model. SP163M affected both the first acute nociceptive phase and the second inflammatory phase of the formalin test. SP163M significantly reduced the duration of the first phase and significantly delayed the start time of the second phase. (*, $p<0.05$, **, $p<0.01$). N=5-6 mice per group.

The effects of SP163M were evaluated in the formalin test, a pain model that has both neurogenic and inflammatory components. In this model, SP163M given as a single subcutaneous injection (50 µg per mouse) resulted in a reduction of the first phase (sensory nerve activation) indicating that SP163M has analgesic effects on the mice and a delay in the second phase (inflammatory reaction due to tissue injury), showing the anti-inflammatory effects of SP163M (FIG. 28).

Accordingly, SERPIN peptides such as SP16 and SP163M have anti-inflammatory and immune-modulating properties, converging on a favorable environment for tissue regeneration and repair. Based on these mechanisms, SP16 and peptide derivatives thereof mediated LRP1 signaling may have therapeutic potential in the treatment of allergic inflammatory diseases such as atopic dermatitis and EoE.

Figure 29A:
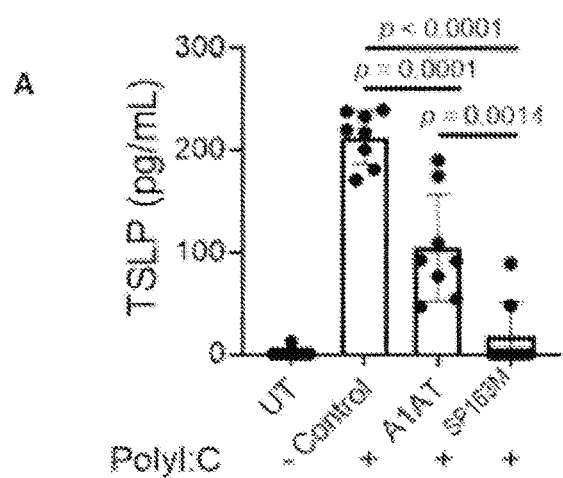
FIGS. 29A-29B demonstrate that SP163M inhibited important mediators of TH2 responses.
Figure 29B:
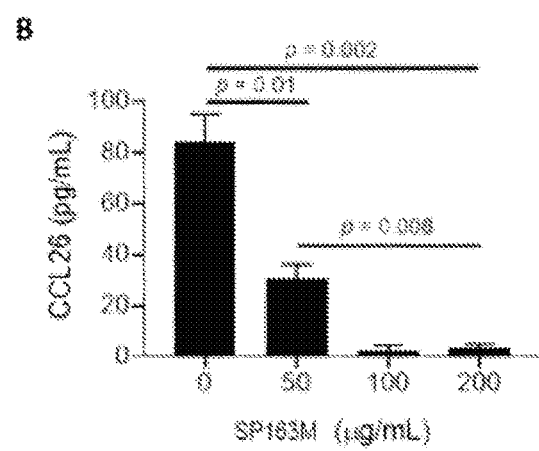

Example 15: In Vitro and In Vivo Effects of SERPIN Peptides in Allergic Inflammatory Diseases Given that loss of SPINK7 is associated with profound cytokine activation, the effects of SP163M and AAT (A1AT) were tested for their ability to reduce thymic stromal lymphopoietin (TSLP), a key immune checkpoint cytokine involved in stimulating TH2 mediated immune responses, in SPINK7 KO cells. FIG. 29A shows that SP163M inhibited TSLP production in SPINK7 knockout esophageal epithelial cells significantly more than A1AT (p=0.0014). In this assay, SP163M was tested at a 20-fold lower concentration compared to AAT, demonstrating its superior potency. In primary epithelial cells, SP163M significantly reduced IL-13 (TH2 mediated cytokine) induced CCL26 (eotaoxin-3) (FIG. 29B), an important marker of inflamed esophageal mucosa in patients with EoE.

Figure 30:
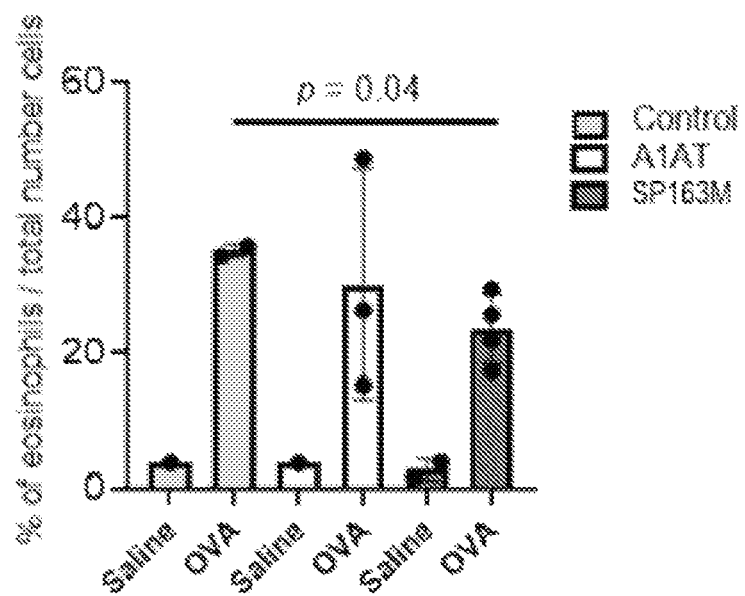
FIG. 30 shows that the mice were subjected to the OVA-induced allergic inflammation model and treated with vehicle, SP163M or A1AT during the challenge phase. The bronchoalveolar lavage fluid (BALF) was collected and analyzed for the percent of eosinophils and compared to saline (non-challenged) mice, vehicle OVA induced mice, or SP163M treated OVA induced mice.

Then the effects of SP163M and AAT were tested in a model of allergic inflammation. In the ovalbumin mouse model of allergic asthma, the mice were sensitized to ovalbumin by two intraperitoneal injections containing the adjuvant alum, a strong inducer of both innate and TH2 mediated immune responses and then challenged with ovalbumin given by intranasal instillation on five separate days, mice were treated with either SP163M (100 µg) or AAT (2 mg) daily during the challenge phase. FIG. 30 shows that SP163M significantly decreased eosinophilic infiltration into the lungs versus vehicle control treated mice, comparable to AAT, but at 20-fold lower dose.

Figure 31:
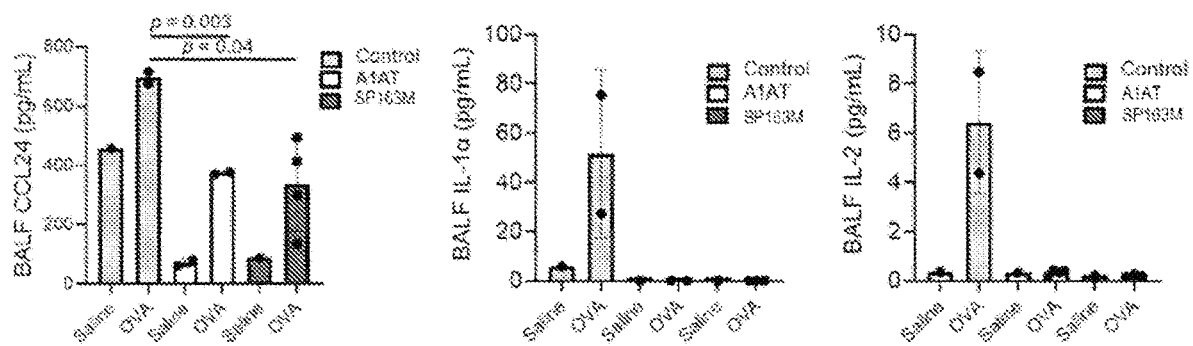
FIG. 31 shows that SP163M inhibited BALF cytokines in ovalbumin asthma model. The mice were subjected to the OVA-challenge allergic inflammation model and treated with vehicle, SP163M or A1AT during the challenge phase. BALF was analyzed for cytokines via ELISA.
Figure 32:
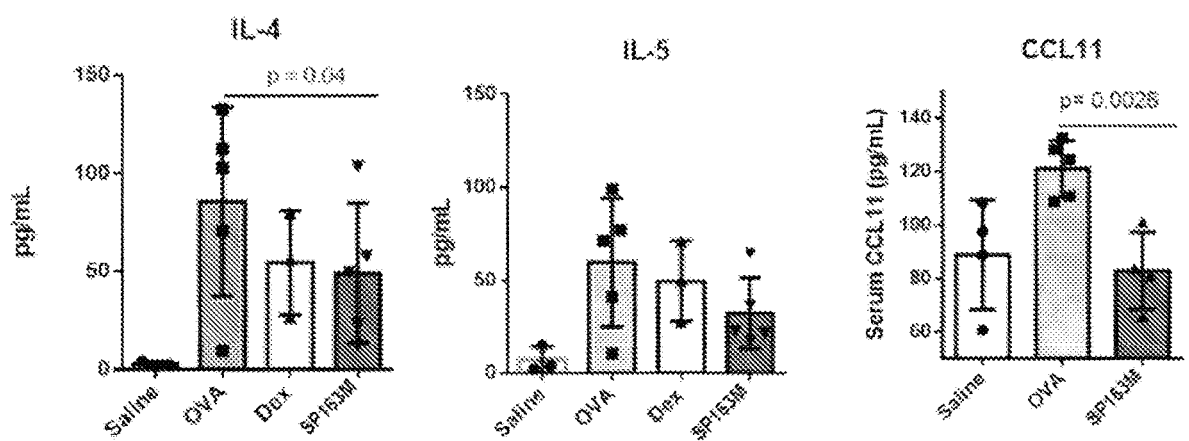
FIG. 32 shows that SP163M inhibited cytokines in ovalbumin asthma model. The mice were subjected to the OVA-challenge allergic inflammation model and treated with vehicle (OVA), SP163M or dexamethasone during the challenge phase. Non-OVA control mice were given saline on the schedule. Lung homogenate (IL-4, IL-5) or serum (CCL11) was analyzed for cytokines via ELISA.

In this model, the bronchoalveolar lavage fluid (BALF) were measured for cytokines/chemokines, CCL24, IL-1α and IL-2 given that these innate immune mediators activate dendritic cells and contribute to T-cell responses. FIG. 31 shows that SP163M treatment resulted in significant decrease in all cytokines. In a separately run study, in which SP163M was dosed every other day, SP163M treatment resulted in lowered TH2 mediated cytokines (IL4, IL-5) in the lung tissue, and at comparable levels to dexamethasone (current standard-of-care treatment) (FIG. 32, left and middle panels). In an OVA-induced inflammation model, it was shown that a single dose of SP163M reduced serum CCL11, a chemokine similar to CCL26 was important in inflammatory cell infiltration (FIG. 32, right panel).

These results suggest that SP163M has ameliorating effects on many of the pathophysiological mechanisms that drive allergic inflammatory diseases.

Example 16: Pharmacokinetics of SERPIN Peptides

Studies conducted in rats were completed to assess the PK parameters of SP163M given systemically by intravenous injection. The half-life of the peptide was determined to be 1.9 hours. The $C_{max}$ ($C_0$ µg/mL) was determined to be 2.5 µg/mL with an $AUC_{last}$ (µg-hr/mL) of 0.9 µg-hr/mL.

Figure 33:
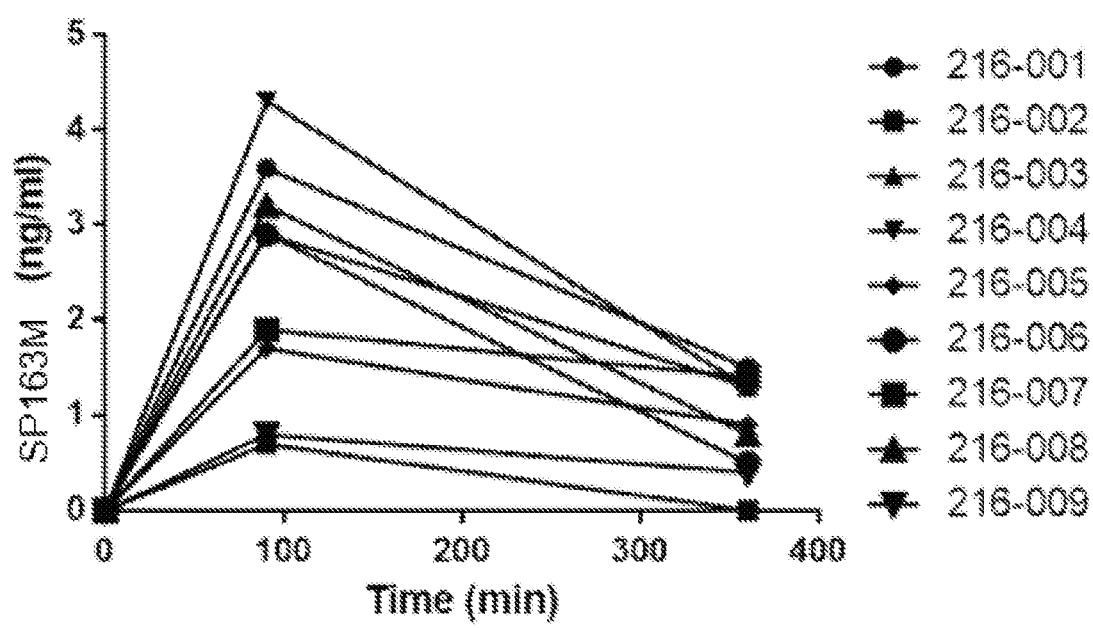
FIG. 33 shows plasma concentration of SP163M in human subjects following a single SC injection (0.2 mg/kg).

A preliminary pharmacokinetic study of patients given a single (0.2 mg/kg) subcutaneous injection of SP163M showed an average of 2.4 ng/mL (SEM±1.24 ng/L) at 90 minutes following injection. Six hours after injection, plasma concentrations of SP163M decreased to an average of 0.9 ng/mL (SEM±0.52 ng/mL) (FIG. 33).

Example 17: Pharmacodynamics of SERPIN Peptides

The 3 µg dose (0.15 mg/kg) of SP163M administered as a single injection to mice is equivalent to 0.012 mg/kg in humans. This is over 16-fold lower than the dose proposed in clinical protocols. Furthermore, the 0.15 mg/kg dose given to mice by subcutaneous injection demonstrated the same effective infarct size reduction as mice given 5 mg/kg (100 µg) by intraperitoneal injection, which is a 2-fold higher equivalent dose than the 0.2 mg/kg dose in humans. This provides evidence that a single subcutaneous administration of SP163M is very potent.

In an acute mouse model of rheumatoid arthritis (CAIA), it was shown that a single administration of SP163M given after paw swelling had started (Day 3) was capable of reducing paw swelling. The dose of 0.6 mg/kg in mice is equivalent to 0.048 mg/kg in humans. Furthermore, PBMCs collected from the arthritic mice treated daily with SP163M following subcutaneous administration (0.6 mg/kg) were exposed to LPS in an ex-vivo assay. This assay shows that cytokines IL-6 and TNF-α were significantly lower vs. vehicle.

In a model of acute lethal septicemia, SP163M was given at 3 doses (4 µg each) at -2, 0, and 0.5 hours of LPS administration. At this cumulative exposure of 0.6 mg/kg (0.048 mg/kg HED), SP163M significantly decreased mortality over a 72-hour period. Further, an acute model of endotoxemia in which TNFα was measured in the serum 1.5 hours following LPS (1 mg/kg) administration. SP163M at 0.2 mg/kg (0.016 mg/kg HED), 1 mg/kg (0.08 mg/kg HED) or 0.2 mg/kg (0.016 mg/kg) reduced this cytokine in the plasma. Given that all the doses exhibited anti-inflammatory effects, a lower dose is likely needed to achieve a dose dependent response.

Example 18: Mechanistic Studies and Tolerance Assays

Finding reliable biomarkers to assess the pharmacodynamic effects of SP163M is an important aspect of clinical trials. The epithelium derived cytokine thymic stromal lymphopoietin (TSLP) and other immune cell derived cytokines/chemokines are important mediators of the allergic reaction which are modified by SP163M in preclinical studies. Furthermore, LRP1 plays a role as a negative regulator of adaptive immune responses mediated by dendritic cells in allergic airway inflammation. Therefore, the ex-vivo effects of SP163M on patient PBMCs induced with IL-13/Poly I:C can be tested. These PBMCs will be analyzed for the cytokine/chemokine expression profile (either by PCR or multiplex). Another assay employs the use of a co-culture model of airway epithelial cells in air liquid interface (ALI) and patient derived dendritic cells and PBMCs to explore the effects of SP163M on TSLP, IL-10 and Tregs. The peptides disclosed herein such as SP16 and SP163M will reduce TSLP mediated effects, and induce favorable dendritic cell mediated T-cell responses, consisting of high IL-10 and Treg cells that are important in the suppression of allergen specific Th2 responses.

Mechanistic studies of tolerance in EoE: Esophageal biopsy specimen is used for scoring for pathological features such as epithelial inflammation and eosinophil infiltration; single cell mRNA, patient reported outcomes (PROs), scoring of esophageal endoscopic features, confocal microscopy analysis of epithelial junctional proteins, and detection of SP163M by Mass Spectrometry or analysis of LRP1 expression. Biomarkers include peripheral blood absolute eosinophil counts (AEC), CRP, TSLP, IL-5, IL-33, IL-6, IL-8, and chemokines such as CCL-26, CCL-11, MCT, CCL27, MIP-3β, and CXCL12. PBMC is used for ex vivo priming of patient cells and cytokine profile. Flow cytometry analysis of biopsies and PBMCs is performed to analyze populations of Th2, Tregs, eosinophils, MCs and ILC2 cells.

Mechanistic studies of tolerance in atopic dermatitis: Skin biopsy is performed to score for pathological features such as epithelial inflammation and eosinophil infiltration. Additional studies include single cell mRNA, patient reported outcomes (PROs), confocal microscopy analysis of epithelial junctional proteins, detection of SP163M by Mass Spectrometry or analysis of LRP1 expression. Biomarkers include peripheral blood absolute eosinophil counts (AEC), CRP, TSLP, IL-5, IL-33, IL-6, IL-8 and chemokines such as CCL-26, CCL-11, MCT, CCL27, MIP-3β, and CXCL12. PBMC is used for ex vivo priming of patient cells and cytokine profile. Flow cytometry analysis of biopsies and PBMCs is performed to analyze populations of Th2, Tregs, eosinophils, MCs and ILC2 cells.

Mechanistic studies of tolerance in asthma: Cells extracted from BAL fluids (lung lavage) are used for scoring for pathological features such immune cells associated with inflammation. Additional studies include single cell mRNA, patient reported outcomes (PROs), confocal microscopy analysis of BAL cells, detection of SP163M by Mass Spectrometry or analysis of LRP1 expression. Biomarkers include peripheral blood absolute eosinophil counts (AEC), CRP, TSLP, IL-5, IL-33, IL-6, IL-8, and chemokines such as CCL-26, CCL-11, MCT, CCL27, MIP-3β, and CXCL12. PBMC is used for ex vivo priming of patient cells and cytokine profile. Flow cytometry analysis of biopsies and PBMCs is performed to analyze populations of Th2, Tregs, eosinophils, MCs and ILC2 cells.

REFERENCES

The references, patents and published patent applications listed below, and all references cited in the specification above are hereby incorporated by reference in their entirety, as if fully set forth herein 1. Berta, T., Y. C. Liu, Z. Z. Xu and R. R. Ji (2013). "Tissue plasminogen activator contributes to morphine tolerance and induces mechanical allodynia via astrocytic IL-1beta and ERK signaling in the spinal cord of mice." *Neuroscience* 247: 376-385.
2. Christia, P., M. Bujak, C. Gonzalez-Quesada, W. Chen, M. Dobaczewski, A. Reddy and N. G. Frangogiannis (2013).

"Systematic characterization of myocardial inflammation, repair, and remodeling in a mouse model of reperfused myocardial infarction." *J Histochem Cytochem* 61(8): 555-570.
3. Cooke, J. P. (2019). "Inflammation and Its Role in Regeneration and Repair." *Circ Res* 124(8): 1166-1168.
4. Feng, Y., B. Liu, X. Zheng, L. Chen, W. Chen and Z. Fang (2019). "The protective role of autophagy in sepsis." *Microb Pathog* 131: 106-111.
5. Franchini, M. and M. Montagnana (2011). "Low-density lipoprotein receptor-related protein 1: new functions for an old molecule." *Clin Chem Lab Med* 49(6): 967-970.
6. Fregnan, F., L. Muratori, A. R. Simoes, M. G. Giacobini-Robecchi and S. Raimondo (2012). "Role of inflammatory cytokines in peripheral nerve injury." *Neural regeneration research* 7(29): 2259-2266.
7. Gali, C. C., E. Fanaee-Danesh, M. Zandl-Lang, N. M. Albrecher, C. Tam-Amersdorfer, A. Stracke, V. Sachdev, F. Reichmann, Y. Sun, A. Avdili, M. Reiter, D. Kratky, P. Holzer, A. Lass, K. K. Kandimalla and U. Panzenboeck (2019). "Amyloid-beta impairs insulin signaling by accelerating autophagy-lysosomal degradation of LRP-1 and IR-β in blood-brain barrier endothelial cells in vitro and in 3XTg-AD mice." *Molecular and Cellular Neuroscience* 99: 103390.
8. Gettins, P. G. W. and S. T. Olson (2016). "Inhibitory serpins. New insights into their folding, polymerization, regulation and clearance." *The Biochemical journal* 473 (15): 2273-2293.
9. Griffin, D., B. Levine, W. Tyor, S. Ubol and P. Despres (1997). "The role of antibody in recovery from alphavirus encephalitis." *Immunol Rev* 159: 155-161.
10. Grosso, R. A., P. V. Subirada Caldarone, M. C. Sanchez, G. A. Chiabrando, M. I. Colombo and C. M. Fader (2018). "Hemin induces autophagy in a leukemic erythroblast cell line through the LRP1 receptor." *Biosci Rep*.
11. Gubler, D. J. (2002). "The global emergence/resurgence of arboviral diseases as public health problems." *Archives of Medical Research* 33(4): 330-342.
12. Hashizume, H., J. A. DeLeo, R. W. Colburn and J. N. Weinstein (2000). "Spinal glial activation and cytokine expression after lumbar root injury in the rat." *Spine* (Phila Pa. 1976) 25(10): 1206-1217.
13. Hemonnot, A.-L., J. Hua, L. Ulmann and H. Hirbec (2019). "Microglia in Alzheimer Disease: Well-Known Targets and New Opportunities." *Frontiers in Aging Neuroscience* 11(233).
14. Herz, J. and D. K. Strickland (2001). "LRP: a multifunctional scavenger and signaling receptor." *J Clin Invest* 108(6): 779-784.
15. Hoffmann, M., H. Kleine-Weber, S. Schroeder, N. Krüger, T. Herrler, S. Erichsen, T. S. Schiergens, G. Herrler, N.-H. Wu, A. Nitsche, M. A. Müller, C. Drosten and S. Pöhlmann (2020). "SARS-CoV-2 Cell Entry Depends on ACE2 and TMPRSS2 and Is Blocked by a Clinically Proven Protease Inhibitor." *Cell*.
16. Hoffmann, M., H. Kleine-Weber, S. Schroeder, N. Krüger, T. Herrler, S. Erichsen, T. S. Schiergens, G. Herrler, N. H. Wu, A. Nitsche, M. A. Müller, C. Drosten and S. Pöhlmann (2020). "SARS-CoV-2 Cell Entry Depends on ACE2 and TMPRSS2 and Is Blocked by a Clinically Proven Protease Inhibitor." *Cell* 181(2): 271-280.e278.
17. Huang, C., Y. Wang, X. Li, L. Ren, J. Zhao, Y. Hu, L. Zhang, G. Fan, J. Xu, X. Gu, Z. Cheng, T. Yu, J. Xia, Y. Wei, W. Wu, X. Xie, W. Yin, H. Li, M. Liu, Y. Xiao, H. Gao, L. Guo, J. Xie, G. Wang, R. Jiang, Z. Gao, Q. Jin, J. Wang and B. Cao (2020). "Clinical features of patients infected with 2019 novel coronavirus in Wuhan, China." *The Lancet* 395(10223): 497-506.
18. Joslin, G., R. J. Fallon, J. Bullock, S. P. Adams and D. H. Perlmutter (1991). "The SEC receptor recognizes a pentapeptide neodomain of alpha 1-antitrypsin-protease complexes." *J Biol Chem* 266(17): 11282-11288.
19. Kawamura, A., D. Baitsch, R. Telgmann, R. Feuerborn, G. Weissen-Plenz, C. Hagedorn, K. Saku, S. M. Brand-Herrmann, A. von Eckardstein, G. Assmann and J. R. Nofer (2007). "Apolipoprotein E interrupts interleukin-1beta signaling in vascular smooth muscle cells." *Arterioscler Thromb Vasc Biol* 27(7): 1610-1617.
20. Kehn-Hall, K., A. Narayanan, L. Lundberg, G. Sampey, C. Pinkham, I. Guendel, R. Van Duyne, S. Senina, K. L. Schultz, E. Stavale, M. J. Aman, C. Bailey and F. Kashanchi (2012). "Modulation of GSK-3beta activity in Venezuelan equine encephalitis virus infection." *PLoS One* 7(4): e34761.
21. Landowski, L. M., M. Pavez, L. S. Brown, R. Gasperini, B. V. Taylor, A. K. West and L. Foa (2016). "Low-density Lipoprotein Receptor-related Proteins in a Novel Mechanism of Axon Guidance and Peripheral Nerve Regeneration." *The Journal of biological chemistry* 291(3): 1092-1102.
22. Lillis, A. P., L. B. Van Duyn, J. E. Murphy-Ullrich and D. K. Strickland (2008). "LDL receptor-related protein 1: unique tissue-specific functions revealed by selective gene knockout studies." *Physiol Rev* 88(3): 887-918.
23. Mantuano, E., M. S. Lam, M. Shibayama, W. M. Campana and S. L. Gonias (2015). "The NMDA receptor functions independently and as an LRP1 co-receptor to promote Schwann cell survival and migration." *Journal of Cell Science* 128(18): 3478-3488.
24. Matsuyama, S., N. Nao, K. Shirato, M. Kawase, S. Saito, I. Takayama, N. Nagata, T. Sekizuka, H. Katoh, F. Kato, M. Sakata, M. Tahara, S. Kutsuna, N. Ohmagari, M. Kuroda, T. Suzuki, T. Kageyama and M. Takeda (2020). "Enhanced isolation of SARS-CoV-2 by TMPRSS2-expressing cells." *Proceedings of the National Academy of Sciences* 117(13): 7001.
25. May, P. (2013). "The low-density lipoprotein receptor-related protein 1 in inflammation." *Curr Opin Lipidol* 24(2): 134-137.
26. May, P., H. H. Bock and J. R. Nofer (2013). "Low density receptor-related protein 1 (LRP1) promotes anti-inflammatory phenotype in murine macrophages." *Cell Tissue Res* 354(3): 887-889.
27. Mehta, P., D. F. McAuley, M. Brown, E. Sanchez, R. S. Tattersall and J. J. Manson (2020). "COVID-19: consider cytokine storm syndromes and immunosuppression." *The Lancet* 395(10229): 1033-1034.
28. Meyer, M. and I. Jaspers (2015). "Respiratory protease/antiprotease balance determines susceptibility to viral infection and can be modified by nutritional antioxidants." *American journal of physiology. Lung cellular and molecular physiology* 308(12): L1189-L1201.
29. Mishra, A., X. Yao, A. Saxena, E. M. Gordon, M. Kaler, R. A. Cuento, A. V. Barochia, P. K. Dagur, J. P. McCoy, K. J. Keeran, K. R. Jeffries, X. Qu, Z.-X. Yu and S. J. Levine (2018). "Low-density lipoprotein receptor–related protein 1 attenuates house dust mite–induced eosinophilic airway inflammation by suppressing dendritic cell–mediated adaptive immune responses." *Journal of Allergy and Clinical Immunology* 142(4): 1066-1079.e1066.

30. Muehlenbein, M. P., F. B. Cogswell, M. A. James, J. Koterski and G. V. Ludwig (2006). "Testosterone correlates with Venezuelan equine encephalitis virus infection in macaques." *Virol J* 3: 19.
31. Olival, K. J. and P. Daszak (2005). "The ecology of emerging neurotropic viruses." *Journal of Neurovirology* 11(5): 441-446.
32. Rauch, J. N., G. Luna, E. Guzman, M. Audouard, C. Challis, Y. E. Sibih, C. Leshuk, I. Hernandez, S. Wegmann, B. T. Hyman, V. Gradinaru, M. Kampmann and K. S. Kosik (2020). "LRP1 is a master regulator of tau uptake and spread." *Nature* 580(7803): 381-385.
33. Ronca, S. E., K. T. Dineley and S. Paessler (2016). "Neurological Sequelae Resulting from Encephalitic Alphavirus Infection." *Front Microbiol* 7: 959.
34. Schoneboom, B. A., K. M. Catlin, A. M. Marty and F. B. Grieder (2000). "Inflammation is a component of neurodegeneration in response to Venezuelan equine encephalitis virus infection in mice." *J Neuroimmunol* 109(2): 132-146.
35. Schoneboom, B. A., J. S. Lee and F. B. Grieder (2000). "Early expression of IFN-alpha/beta and iNOS in the brains of Venezuelan equine encephalitis virus-infected mice." *J Interferon Cytokine Res* 20(2): 205-215.
36. Sharma, A., B. Bhattacharya, R. K. Puri and R. K. Maheshwari (2008). "Venezuelan equine encephalitis virus infection causes modulation of inflammatory and immune response genes in mouse brain." *BMC Genomics* 9: 289.
37. Sharma, A., M. Bhomia, S. P. Honnold and R. K. Maheshwari (2011). "Role of adhesion molecules and inflammation in Venezuelan equine encephalitis virus infected mouse brain." *Virology Journal* 8: 197-197.
38. Shi, Y., E. Mantuano, G. Inoue, W. M. Campana and S. L. Gonias (2009). "Ligand binding to LRP1 transactivates Trk receptors by a Src family kinase-dependent pathway." *Sci Signal* 2(68): ra18.
39. Shi, Y., T. Yamauchi, A. Gaultier, S. Takimoto, W. M. Campana and S. L. Gonias (2011). "Regulation of cytokine expression by Schwann cells in response to alpha2-macroglobulin binding to LRP1." *J Neurosci Res* 89(4): 544-551.
40. Shiga, Y., A. Shiga, P. Mesci, H. Kwon, C. Brifault, J. H. Kim, J. J. Jeziorski, C. Nasamran, S. Ohtori, A. R. Muotri, S. L. Gonias and W. M. Campana (2019). "Tissue-type plasminogen activator-primed human iPSC-derived neural progenitor cells promote motor recovery after severe spinal cord injury." *Scientific Reports* 9(1): 19291.
41. Simon, D., B. Page, M. Vogel, C. Bussmann, C. Blanchard, A. Straumann and H.-U. Simon (2018). "Evidence of an abnormal epithelial barrier in active, untreated and corticosteroid-treated eosinophilic esophagitis." *Allergy* 73(1): 239-247.
42. Steele, K. E. and N. A. Twenhafel (2010). "REVIEW PAPER: pathology of animal models of alphavirus encephalitis." *Vet Pathol* 47(5): 790-805.
43. Strickland, D. K., S. C. Muratoglu and T. M. Antalis (2011). "Serpin-Enzyme Receptors LDL Receptor-Related Protein 1." *Methods Enzymol* 499: 17-31.
44. Subramaniyam, D., P. Glader, K. von Wachenfeldt, J. Burneckiene, T. Stevens and S. Janciauskiene (2006). "C-36 peptide, a degradation product of alpha1-antitrypsin, modulates human monocyte activation through LPS signaling pathways." *Int J Biochem Cell Biol* 38(4): 563-575.
45. Taylor, K. G. and S. Paessler (2013). "Pathogenesis of Venezuelan equine encephalitis." *Vet Microbiol* 167(1-2): 145-150.
46. Toldo, S., D. Austin, A. G. Mauro, E. Mezzaroma, B. W. Van Tassell, C. Marchetti, S. Carbone, S. Mogelsvang, C. Gelber and A. Abbate (2017). "Low-Density Lipoprotein Receptor-Related Protein-1 Is a Therapeutic Target in Acute Myocardial Infarction." *JACC Basic Transl Sci* 2(5): 561-574.
47. Wang, Y., K. Jiang, Q. Zhang, S. Meng and C. Ding (2018). "Autophagy in Negative-Strand RNA Virus Infection." *Frontiers in Microbiology* 9(206).
48. Weaver, S. C., C. Ferro, R. Barrera, J. Boshell and J. C. Navarro (2004). "Venezuelan equine encephalitis." *Annu Rev Entomol* 49: 141-174.
49. Wujak, L., P. Markart and M. Wygrecka (2016). "The low density lipoprotein receptor-related protein (LRP) 1 and its function in lung diseases." *Histol Histopathol* 31(7): 733-745.
50. Wujak, L., J. Schnieder, L. Schaefer and M. Wygrecka (2018). "LRP1: A chameleon receptor of lung inflammation and repair." *Matrix Biology* 68-69: 366-381.
51. Yang, L., C.-C. Liu, H. Zheng, T. Kanekiyo, Y. Atagi, L. Jia, D. Wang, A. N'songo, D. Can, H. Xu, X.-F. Chen and G. Bu (2016). "LRP1 modulates the microglial immune response via regulation of JNK and NF-κB signaling pathways." *Journal of Neuroinflammation* 13(1): 304.
52. Yang, X., Y. Yu, J. Xu, H. Shu, J. a. Xia, H. Liu, Y. Wu, L. Zhang, Z. Yu, M. Fang, T. Yu, Y. Wang, S. Pan, X. Zou, S. Yuan and Y. Shang (2020). "Clinical course and outcomes of critically ill patients with SARS-CoV-2 pneumonia in Wuhan, China: a single-centered, retrospective, observational study." *The Lancet Respiratory Medicine*.
53. Yoon, C., E. A. Van Niekerk, K. Henry, T. Ishikawa, S. Orita, M. H. Tuszynski and W. M. Campana (2013). "Low-density Lipoprotein Receptor-related Protein 1 (LRP1)-dependent Cell Signaling Promotes Axonal Regeneration." *Journal of Biological Chemistry* 288(37): 26557-26568.
54. Zlokovic, B. V., R. Deane, A. P. Sagare, R. D. Bell and E. A. Winkler (2010). "Low-density lipoprotein receptor-related protein-1: a serial clearance homeostatic mechanism controlling Alzheimer's amyloid β-peptide elimination from the brain." *Journal of neurochemistry* 115(5): 1077-1089.
55. Zurhove, K., C. Nakajima, J. Herz, H. H. Bock and P. May (2008). "Gamma-secretase limits the inflammatory response through the processing of LRP1." *Science signaling* 1(47): ra15-ra15.

The invention claimed is:

1. A method of treating a subject that suffers from a disease or condition associated with thymic stromal lymphopoietin (TSLP), comprising administering to the subject an effective amount of a composition comprising a serine protease inhibitor (SERPIN) peptide or a fusion thereof, wherein the SERPIN peptide comprises the amino acid sequence of VKFNKPFVFL(Nle)IEQNTK (SEQ ID NO: 35), wherein the disease or condition associated with TSLP is asthma, atopic dermatitis, allergic rhinoconjunctivitis, eosinophilic esophagitis (EoE), or rheumatoid arthritis.

2. The method of claim 1, wherein the fusion comprises the SERPIN peptide and an epitope tag, a half-life extender, or both.

3. The method of claim 1, wherein the subject is human.

4. The method of claim 1, wherein the administration is by oral administration, parenteral administration, intradermal administration, transdermal administration, topical administration, or intranasal administration.

5. The method of claim 1, wherein the composition is administered as a single dose.

6. The method of claim 1, wherein the composition is administered at a dose of between 0.001 mg/kg and 5 mg/kg.

* * * * *